(12) United States Patent
Lee et al.

(10) Patent No.: US 10,950,807 B2
(45) Date of Patent: Mar. 16, 2021

(54) ORGANOMETALLIC COMPOUND, ORGANIC LIGHT-EMITTING DEVICE INCLUDING THE ORGANOMETALLIC COMPOUND, AND DIAGNOSTIC COMPOSITION INCLUDING THE ORGANOMETALLIC COMPOUND

(71) Applicant: Samsung Electronics Co., Ltd., Suwon-si (KR)

(72) Inventors: Banglin Lee, Suwon-si (KR); Seungyeon Kwak, Suwon-si (KR); Kum Hee Lee, Suwon-si (KR); Shingo Ishihara, Suwon-si (KR); Yongsuk Cho, Hwaseong-si (KR); Hwayoung Cho, Hwaseong-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 334 days.

(21) Appl. No.: 15/957,344

(22) Filed: Apr. 19, 2018

(65) Prior Publication Data

US 2018/0309072 A1 Oct. 25, 2018

(30) Foreign Application Priority Data

Apr. 21, 2017 (KR) .................. 10-2017-0051886

(51) Int. Cl.
*H01L 51/00* (2006.01)
*C07F 15/00* (2006.01)
(Continued)

(52) U.S. Cl.
CPC ........ *H01L 51/0087* (2013.01); *A61K 31/555* (2013.01); *C07F 15/0086* (2013.01);
(Continued)

(58) Field of Classification Search
None
See application file for complete search history.

(56) References Cited

U.S. PATENT DOCUMENTS

2007/0103060 A1\* 5/2007 Itoh ............... C07D 213/30
313/504
2012/0223634 A1\* 9/2012 Xia ............... H01L 51/0094
313/504

(Continued)

FOREIGN PATENT DOCUMENTS

KR 10-2014-0140075 A 12/2014
WO 2014047616 A1 3/2014

OTHER PUBLICATIONS

Extended European Search Report Issued by the European Patent Office dated Sep. 18, 2018, in the examination of the European Patent Application No. 18168055.4-1109.

*Primary Examiner* — Robert S Loewe
(74) *Attorney, Agent, or Firm* — Cantor Colburn LLP

(57) ABSTRACT

An organometallic compound represented by Formula 1:

Formula 1

(Continued)

wherein, in Formula 1, groups and variables are the same as described in the specification.

20 Claims, 2 Drawing Sheets

(51) Int. Cl.
    *A61K 31/555*     (2006.01)
    *C09K 11/06*     (2006.01)
    *H01L 51/50*     (2006.01)

(52) U.S. Cl.
    CPC ...... *C09K 11/06* (2013.01); *C09K 2211/1029* (2013.01); *C09K 2211/185* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | | |
|---|---|---|---|---|
| 2012/0302753 A1* | 11/2012 | Li | ........... | H01L 51/0087 546/4 |
| 2013/0168656 A1* | 7/2013 | Tsai | ........... | H01L 51/0032 257/40 |
| 2013/0341600 A1* | 12/2013 | Lin | ........... | C09K 11/06 257/40 |
| 2014/0364605 A1* | 12/2014 | Li | ........... | H01L 51/0087 544/225 |
| 2015/0008419 A1* | 1/2015 | Li | ........... | H01L 51/5016 257/40 |
| 2015/0207086 A1* | 7/2015 | Li | ........... | C07F 15/006 546/4 |
| 2015/0228914 A1* | 8/2015 | Li | ........... | H01L 51/0087 540/541 |
| 2015/0274762 A1 | 10/2015 | Li et al. | | |
| 2015/0349279 A1 | 12/2015 | Li et al. | | |
| 2016/0181551 A1 | 6/2016 | Che et al. | | |
| 2017/0183368 A1* | 6/2017 | Hara | ........... | H01L 51/0087 |
| 2018/0208615 A1* | 7/2018 | Lin | ........... | C09K 11/06 |

\* cited by examiner

ORGANOMETALLIC COMPOUND, ORGANIC LIGHT-EMITTING DEVICE INCLUDING THE ORGANOMETALLIC COMPOUND, AND DIAGNOSTIC COMPOSITION INCLUDING THE ORGANOMETALLIC COMPOUND

CROSS-REFERENCE TO RELATED APPLICATION

This application claims priority to Korean Patent Application No. 10-2017-0051886, filed on Apr. 21, 2017, in the Korean Intellectual Property Office, and all the benefits accruing therefrom under 35 U.S.C. § 119, the disclosure of which is incorporated herein in its entirety by reference.

BACKGROUND

1. Field

One or more embodiments relate to an organometallic compound, an organic light-emitting device including the organometallic compound, and a diagnostic composition including the organometallic compound.

2. Description of the Related Art

Organic light-emitting devices (OLEDs) are self-emission devices, which have superior characteristics in terms of a viewing angle, a response time, a brightness, a driving voltage, and a response speed, and which produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

Meanwhile, luminescent compounds may be used to monitor, sense, or detect a variety of biological materials including cells and proteins. An example of the luminescent compounds includes a phosphorescent luminescent compound.

Various types of organic light emitting devices are known. However, there still remains a need in OLEDs having low driving voltage, high efficiency, high brightness, and long lifespan.

SUMMARY

Aspects of the present disclosure provide an organometallic compound, an organic light-emitting device including the organometallic compound, and a diagnostic composition including the organometallic compound.

Additional aspects will be set forth in part in the description which follows and, in part, will be apparent from the description, or may be learned by practice of the presented embodiments.

An aspect of the present disclosure provides an organometallic compound represented by Formula 1 below:

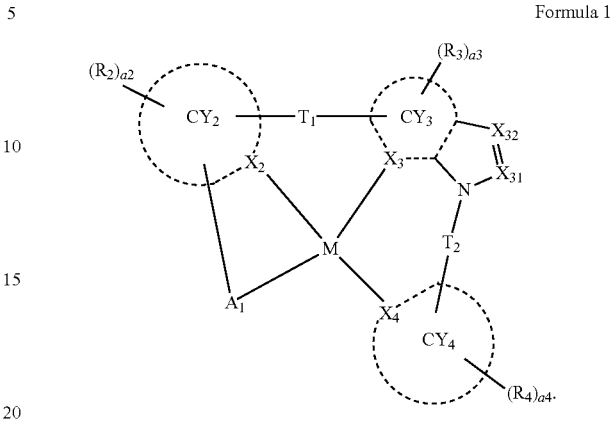

Formula 1

In Formula 1,

M may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), two bonds selected from a bond between $A_1$ and M, a bond between $X_2$ and M, a bond between $X_3$ and M, and a bond between $X_4$ and M may each be a covalent bond, and the others thereof may each be a coordinate bond, $A_1$ may be a first atom linked to M, a non-cyclic moiety including the first atom linked to M, or ring $CY_1$ including $X_1$ linked to M and substituted with groups $R_1$ in the number of a1, the first atom may be B, N, P, C, Si, O, or S, $X_1$ to $X_4$ may each independently be N or C, rings $CY_1$ to $CY_4$ may each independently be selected from a $C_5$-$C_{30}$ carbocyclic group and a $C_1$-$C_{30}$ heterocyclic group, a cyclometalated ring formed by $A_1$, $CY_2$, and M may be a 5-membered ring, $X_{31}$ may be $C(R_{31})$ or N, and $X_{32}$ may be $C(R_{32})$ or N, wherein, when $X_{31}$ is $C(R_{31})$ and $X_{32}$ is $C(R_{32})$, $R_{31}$ and $R_{32}$ may not be linked to each other, $T_1$ and $T_2$ may each independently be selected from a single bond, a double bond, *—$N(R_5)$—*', *—$B(R_5)$—*', *—$P(R_5)$—*', *—$C(R_5)(R_6)$—*', *—$Si(R_5)(R_6)$—*', *—$Ge(R_5)(R_6)$—*', *—S—*', *—Se—*', *—O—*', *—C(=O)—*', *—S(=O)—*', *—S(=O)$_2$—*', *—$C(R_5)$=*', *=$C(R_5)$—*', $C(R_5)$=$C(R_6)$—*', *—C(=S)—*', and *—C≡C—*', and * and *' each indicate a binding site to a neighboring atom, $R_5$ and $R_6$ may optionally be linked via a single bond, a double bond, or a first linking group to form a substituted or unsubstituted $C_5$-$C_{30}$ carbocyclic group or a substituted or unsubstituted $C_1$-$C_{30}$ heterocyclic group, $R_1$ to $R_6$, $R_{31}$, and $R_{32}$ may each independently be selected from hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), a1 to a4 may each independently be an integer from 0 to 20, two of a plurality of neighboring groups $R_1$ may optionally be linked to form a substituted or unsubstituted $C_5$-$C_{30}$ carbocyclic group or a substituted or unsubstituted $C_1$-$C_{30}$ heterocyclic group, two of a plurality of neighboring groups $R_2$ may optionally be linked to form a substituted or unsubstituted $C_5$-$C_{30}$ carbocyclic group or a substituted or unsubstituted $C_1$-$C_{30}$ heterocyclic group, two of a plurality of neighboring groups $R_3$ may optionally be linked to form a substituted or unsubstituted $C_5$-$C_{30}$ carbocyclic group or a substituted or unsubstituted $C_1$-$C_{30}$ heterocyclic group, two of a plurality of neighboring groups $R_4$ may optionally be linked to form a substituted or unsubstituted $C_5$-$C_{30}$ carbocyclic group or a substituted or unsubstituted $C_1$-$C_{30}$ heterocyclic group, two or more neighboring groups selected from $R_1$ to $R_4$ may optionally be linked to form a substituted or unsubstituted $C_5$-$C_{30}$ carbocyclic group or a substituted or unsubstituted $C_1$-$C_{30}$ heterocyclic group, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{16}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one selected from deuterium, a $C_1$-$C_{60}$ alkyl group, and a $C_6$-$C_{60}$ aryl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from deuterium, a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Another aspect of the present disclosure provides an organic light-emitting device including:

a first electrode, a second electrode, and an organic layer disposed between the first electrode and the second electrode, wherein the organic layer includes an emission layer and at least one of the organometallic compound.

The organometallic compounds may act as a dopant in the organic layer.

Another aspect of the present disclosure provides a diagnostic composition including at least one organometallic compound represented by Formula 1.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
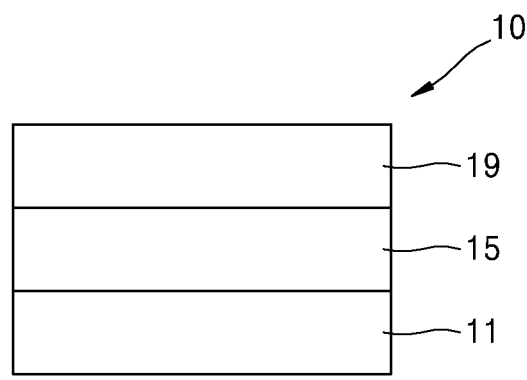
FIG. 1 is a schematic view of an organic light-emitting device according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

In an embodiment, an organometallic compound is provided. The organometallic compound according to an embodiment is represented by Formula 1 below:

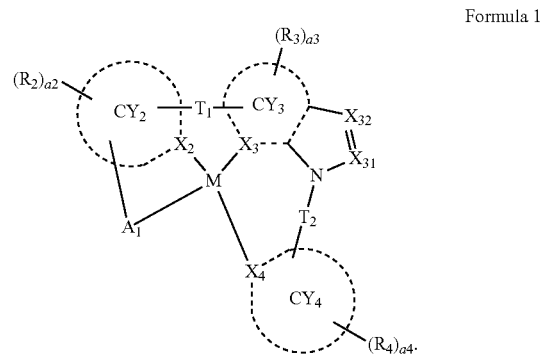

Formula 1

M in Formula 1 may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au).

For example, M may be Pt or Pd.

In an embodiment, M may be Pt, but embodiments of the present disclosure are not limited thereto.

In Formula 1, two bonds selected from a bond between $A_1$ and M, a bond between $X_2$ and M, a bond between $X_3$ and M, and a bond between $X_4$ and M may each be a covalent bond, and the others thereof may each be a coordinate bond. Accordingly, the organometallic compound represented by Formula 1 may be electrically neutral.

In an embodiment, a bond between $A_1$ and M and a bond between $X_4$ and M may each be a coordinate bond, and a bond between $X_2$ and M and a bond between $X_3$ and M may each be a covalent bond, but embodiments of the present disclosure are not limited thereto.

$A_1$ in Formula 1 may be a first atom linked to M, a non-cyclic moiety including the first atom linked to M, or a ring $CY_1$ including $X_1$ linked to M and substituted with groups $R_1$ in the number of a1.

The first atom may be B, N, P, C, Si, O, or S.

For example, the first atom may be N, P, C, Si, or O, but embodiments of the present disclosure are not limited thereto.

In an embodiment, the first atom may be O.

The non-cyclic moiety including the first atom linked to M may be *—C($R_{11}$)—*', *—Si($R_{11}$)—*', *—B($R_{11}$)—*', *—N($R_{11}$)—*', *—P($R_{11}$)—*', *—C($R_{11}$)($R_{12}$)—*', *—Si($R_{11}$)($R_{12}$)—*', *—C($R_{11}$)—C(=O)—*', *—Si($R_{11}$)—C(=O)—*', *—B($R_{11}$)—C(=O)—*', *—N($R_{11}$)—C(=O)—*', *—P($R_{11}$)—C(=O)—*', *—C($R_{11}$)($R_{12}$)—C(=O)—*', or *—Si($R_{11}$)($R_{12}$)—C(=O)—*' (wherein $R_{11}$ and $R_{12}$ are the same as described in connection with $R_1$, * indicates a binding site to M in Formula 1, and *' indicates a binding site to $T_2$ in Formula 1).

$X_1$, a1, $R_1$, and $CY_1$ are the same as described herein.

$X_1$ to $X_4$ may each independently be N or C.

For example, $X_1$ and $X_4$ may each be N, and $X_2$ and $X_3$ may each be C, but embodiments of the present disclosure are not limited thereto.

Rings $CY_1$ to $CY_4$ may each independently be selected from a $C_5$-$C_{30}$ carbocyclic group and a $C_1$-$C_{30}$ heterocyclic group.

For example, rings $CY_1$ to $CY_4$ may each independently be selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzooxadiazole group, a benzothiadiazole group, a 5,6,7,8-tetrahydroisoquinoline group, and a 5,6,7,8-tetrahydroquinoline group.

In an embodiment, at least one of rings $CY_2$ and $CY_4$ may be a condensed ring in which at least one 5-membered ring is condensed with at least one 6-membered ring, wherein the 5-membered ring may be selected from a cyclopentadiene group, a furan group, a thiophene group, a pyrrole group, a silole group, an oxazole group, an isoxazole group, an oxadiazole group, an isoxadiazole group, an oxatriazole group, an isoxatriazole group, a thiazole group, an isothiazole group, a thiadiazole group, an isothiadiazole group, a thiatriazole group, an isothiatriazole group, a pyrazole group, an imidazole group, a triazole group, a tetrazole group, an azasilole group, a diazasilole group, and a triazasilole group, and the 6-membered ring may be selected from a cyclohexane group, a cyclohexene group, a benzene group, a pyridine group, a pyrimidine group, a pyrazine group, and a pyridazine group.

In an embodiment, at least one of rings $CY_2$ and $CY_4$ may be a condensed ring with at least two 6-membered rings, wherein the 6-membered ring may be selected from a cyclohexane group, a cyclohexene group, a benzene group, a pyridine group, a pyrimidine group, a pyrazine group, and a pyridazine group, but embodiments of the present disclosure are not limited thereto.

In an embodiment, when ring $CY_2$ is the condensed ring with the at least one 5-membered ring and the at least one 6-membered ring, the 5-membered ring in the condensed ring may be linked to $A_1$ in Formula 1.

In one or more embodiments, when ring $CY_2$ is the condensed ring with the at least one 5-membered ring and the at least one 6-membered ring, the 5-membered ring in the condensed ring may be linked to $T_1$ in Formula 1.

In one or more embodiments, when ring $CY_4$ is the condensed ring with the at least one 5-membered ring and the at least one 6-membered ring, the 5-membered ring in the condensed ring may be linked to $T_2$ in Formula 1.

In one or more embodiments, when ring $CY_4$ is the condensed ring with the at least one 5-membered ring and the at least one 6-membered ring, the 6-membered ring in the condensed ring may be linked to $T_2$ in Formula 1.

A cyclometalated ring formed by $A_1$, $CY_2$, and M in Formula 1 may be a 5-membered ring.

In Formula 1, $X_{31}$ may be $C(R_{31})$ or N, and $X_{32}$ may be $C(R_{32})$ or N.

For example, $X_{31}$ may be $C(R_{31})$, and $X_{32}$ may be $C(R_{32})$ or N, but embodiments of the present disclosure are not limited thereto.

In Formula 1, when $X_{31}$ is $C(R_{31})$ and $X_{32}$ is $C(R_{32})$, $R_{31}$ and $R_{32}$ may not be linked to each other.

$T_1$ and $T_2$ in Formula 1 may each independently be selected from a single bond, a double bond, *—N($R_5$)—*', *—B($R_5$)—*', *—P($R_5$)—*', *—C($R_5$)($R_6$)—*', *—Si($R_5$)($R_6$)—*', *—Ge($R_5$)($R_6$)—*', *—S—*', *—Se—*', *—O—*', *—C(=O)—*', *—S(=O)—*', *—S(=O)$_2$—*', *—C($R_5$)=*', *=C($R_5$)—*', *—C($R_5$)=C($R_6$)—*', *—C(=S)—*', and *—C≡C—*'. $R_5$ and $R_6$ are the same as described herein, and $R_5$ and $R_6$ may optionally be linked via a single bond, a double bond, or a first linking group to form a substituted or unsubstituted $C_5$-$C_{30}$ carbocyclic group or a substituted or unsubstituted $C_1$-$C_{30}$ heterocyclic group.

The first linking group may be selected from *—N($R_7$)—*', *—B($R_7$)—*', *—P($R_7$)—*', *—C($R_7$)($R_8$)—*', *—Si($R_7$)($R_8$)—*', *—Ge($R_7$)($R_8$)—*', *—S—*', *—Se—*', *—O—*', *—C(=O)—*', *—S(=O)—*', *—S(=O)$_2$—*', *—C($R_7$)=*', *=C($R_7$)—*', *—C($R_7$)=C($R_8$)—*', *—C(=S)—*', and *—C≡C—*', $R_7$ and $R_8$ are the same as described in connection with $R_5$, and * and *' each indicate a binding site to a neighboring atom.

In an embodiment, $T_2$ may be a single bond.

In one or more embodiments, $T_1$ may be selected from a single bond, *—N($R_5$)—*', *—C($R_5$)($R_6$)—*', *—Si($R_5$)($R_6$)—*', *—S—*', *—O—*', and *—C(=O)—*', and $T_2$ may be a single bond, but embodiments of the present disclosure are not limited thereto.

At least one of $R_5$ and $R_6$ may optionally be linked to at least one of $CY_2$ and $CY_3$ in Formula 1 via a single bond, a double bond, or a second linking group to form a substituted or unsubstituted $C_5$-$C_{30}$ carbocyclic group or a substituted or unsubstituted $C_1$-$C_{30}$ heterocyclic group. The second linking group is the same as described in connection with the first linking group.

$R_1$ to $R_6$, $R_{31}$, and $R_{32}$ may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$).

For example, $R_1$ to $R_6$, $R_{31}$, and $R_{32}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, and —Si($Q_{33}$)($Q_{34}$)($Q_{35}$); and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ and $Q_{33}$ to $Q_{35}$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In an embodiment, $R_1$ to $R_6$, $R_{31}$, and $R_{32}$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formula 9-1 to 9-19, groups represented by Formulae 10-1 to 10-161, —$N(Q_1)(Q_2)$, —$Si(Q_3)(Q_4)(Q_5)$, —$B(Q_6)(Q_7)$, and —$P(=O)(Q_8)(Q_9)$ (wherein $Q_1$ to $Q_9$ are the same as described herein), but embodiments of the present disclosure are not limited thereto:

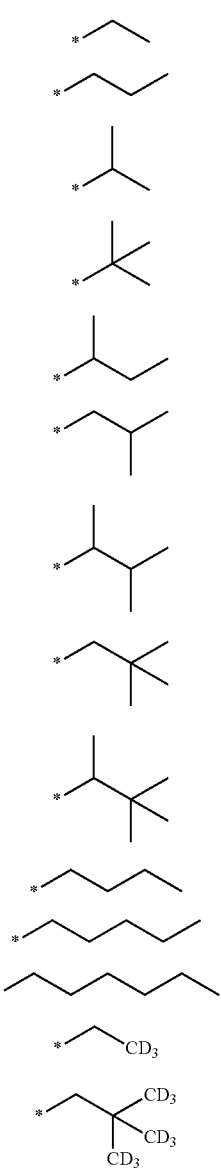

Formula 9-1
Formula 9-2
Formula 9-3
Formula 9-4
Formula 9-5
Formula 9-6
Formula 9-7
Formula 9-8
Formula 9-9
Formula 9-10
Formula 9-11
Formula 9-12
Formula 9-13
Formula 9-14

-continued

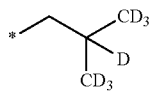

Formula 9-15

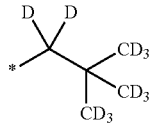

Formula 9-16

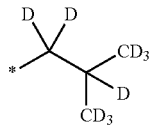

Formula 9-17

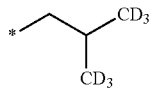

Formula 9-18

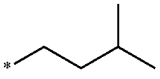

Formula 9-19

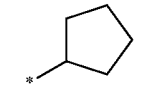

Formula 10-1

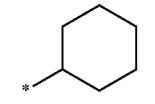

Formula 10-2

Formula 10-3

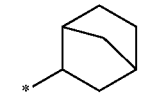

Formula 10-4

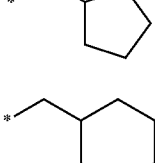

Formula 10-5

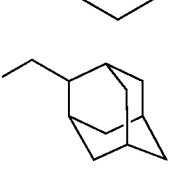

Formula 10-6

Formula 10-7

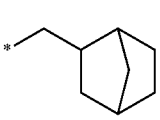

Formula 10-8

-continued
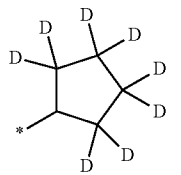
Formula 10-9
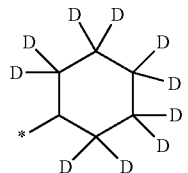
Formula 10-10
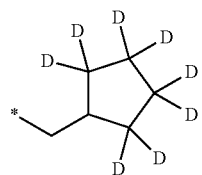
Formula 10-11
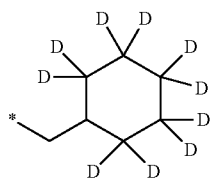
Formula 10-12
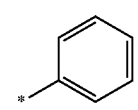
Formula 10-13
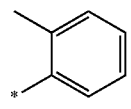
Formula 10-14
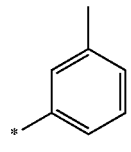
Formula 10-15
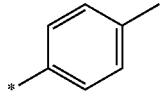
Formula 10-16
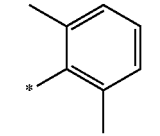
Formula 10-17
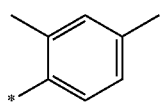
Formula 10-18
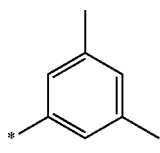
Formula 10-19
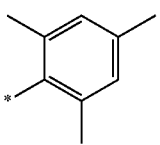
Formula 10-20
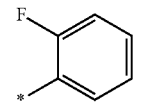
Formula 10-21
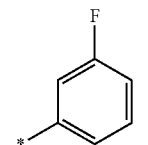
Formula 10-22
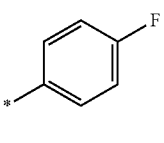
Formula 10-23
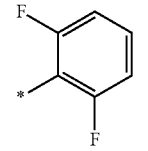
Formula 10-24
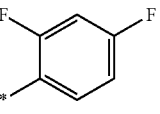
Formula 10-25
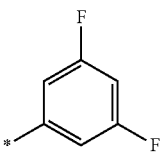
Formula 10-26
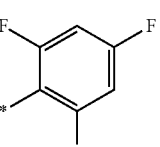
Formula 10-27
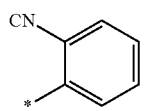
Formula 10-28
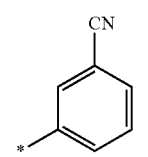
Formula 10-29
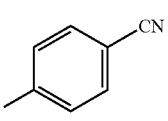
Formula 10-30

-continued
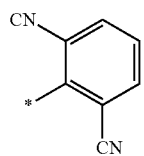
Formula 10-31
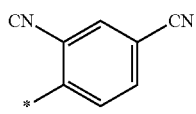
Formula 10-32
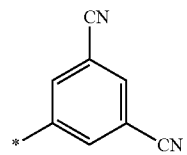
Formula 10-33
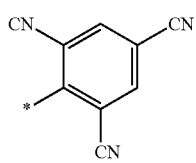
Formula 10-34
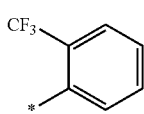
Formula 10-35
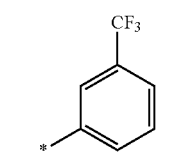
Formula 10-36
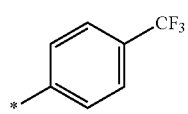
Formula 10-37
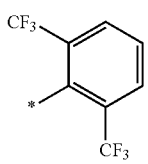
Formula 10-38
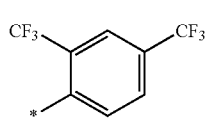
Formula 10-39
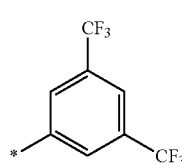
Formula 10-40
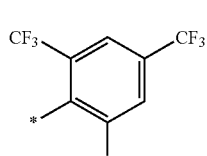
Formula 10-41
-continued
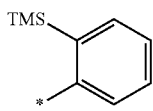
Formula 10-42
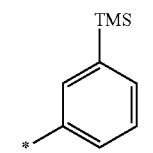
Formula 10-43
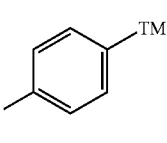
Formula 10-44
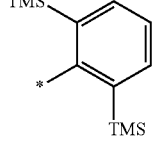
Formula 10-45
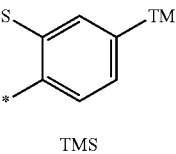
Formula 10-46
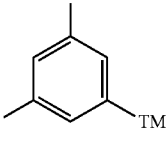
Formula 10-47
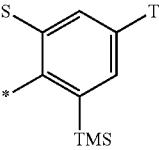
Formula 10-48
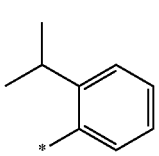
Formula 10-49
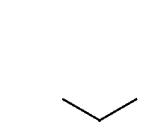
Formula 10-50
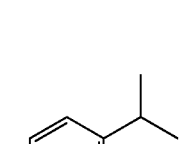
Formula 10-51

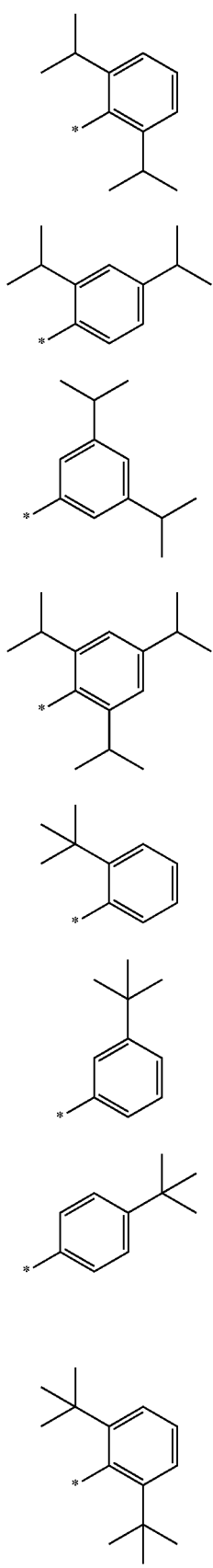
Formula 10-52
Formula 10-53
Formula 10-54
Formula 10-55
Formula 10-56
Formula 10-57
Formula 10-58
Formula 10-59
Formula 10-60
Formula 10-61
Formula 10-62
Formula 10-63
Formula 10-64
Formula 10-65
Formula 10-66
Formula 10-67
Formula 10-68
Formula 10-69

Formula 10-70
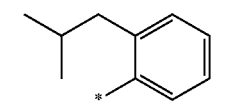
Formula 10-71
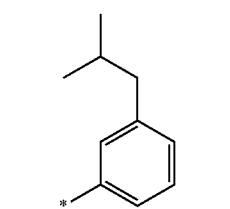
Formula 10-72
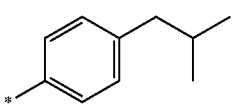
Formula 10-73
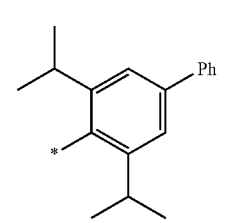
Formula 10-74
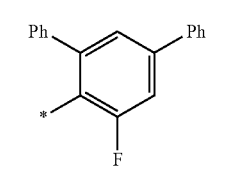
Formula 10-75
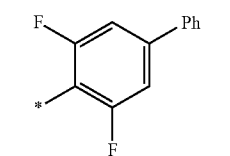
Formula 10-76
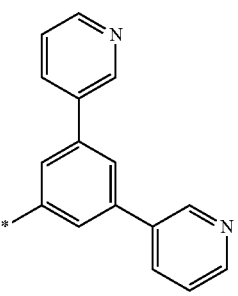
Formula 10-77
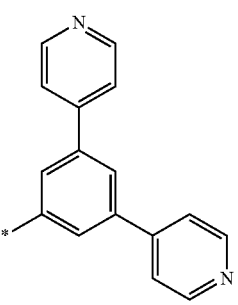
Formula 10-78
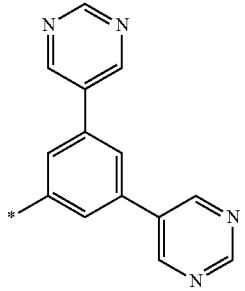
Formula 10-79
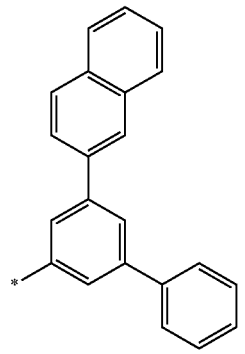
Formula 10-80
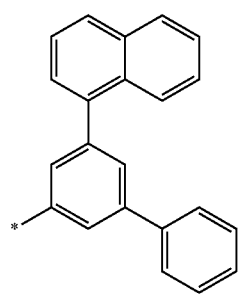
Formula 10-81
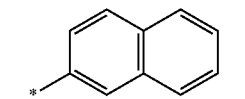
Formula 10-82
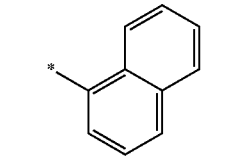
Formula 10-83
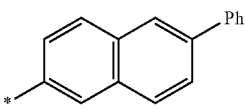
Formula 10-84
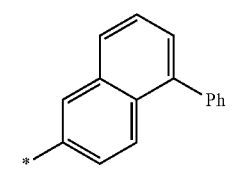

-continued
| | | |
|---|---|---|
| 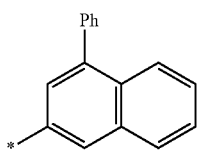 | Formula 10-85 | |
| 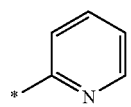 | Formula 10-86 | |
| 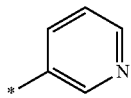 | Formula 10-87 | |
| 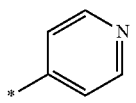 | Formula 10-88 | |
| 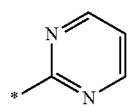 | Formula 10-89 | |
| 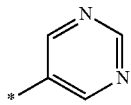 | Formula 10-90 | |
| 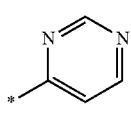 | Formula 10-91 | |
| 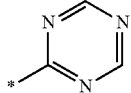 | Formula 10-92 | |
| 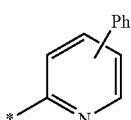 | Formula 10-93 | |
| 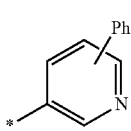 | Formula 10-94 | |
| 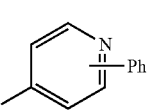 | Formula 10-95 | |
| 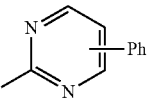 | Formula 10-96 | |
| 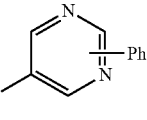 | Formula 10-97 | |
-continued
| | | |
|---|---|---|
| 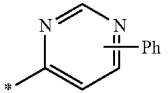 | Formula 10-98 | |
| 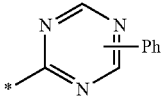 | Formula 10-99 | |
| 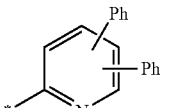 | Formula 10-100 | |
| 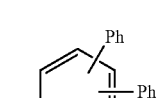 | Formula 10-101 | |
| 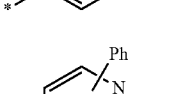 | Formula 10-102 | |
| 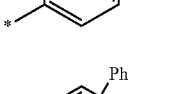 | Formula 10-103 | |
| 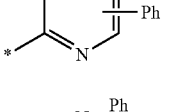 | Formula 10-104 | |
| 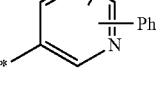 | Formula 10-105 | |
| 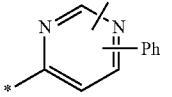 | Formula 10-106 | |
| 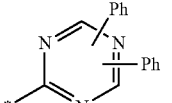 | Formula 10-107 | |
| 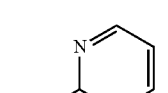 | Formula 10-108 | |

Formula 10-109

Formula 10-110

Formula 10-111

Formula 10-112

Formula 10-113

Formula 10-114

Formula 10-115

Formula 10-116

Formula 10-117

Formula 10-118

Formula 10-119

Formula 10-120

Formula 10-121

Formula 10-122

Formula 10-123

Formula 10-124

-continued
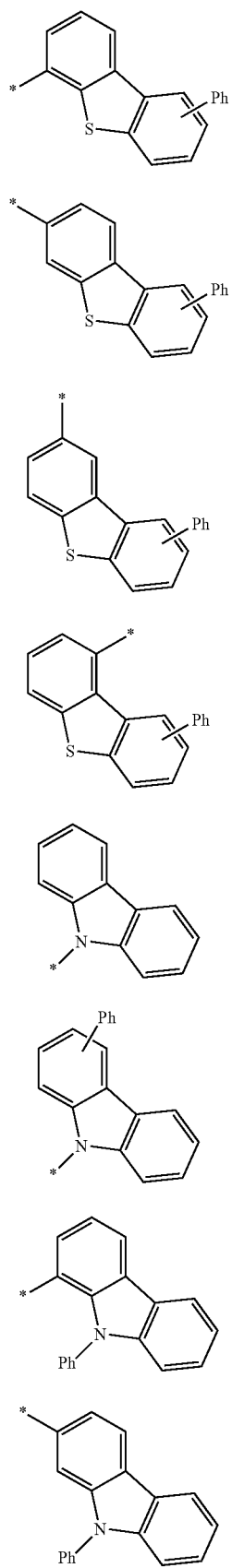
Formula 10-125
Formula 10-126
Formula 10-127
Formula 10-128
Formula 10-129
Formula 10-130
Formula 10-131
Formula 10-132
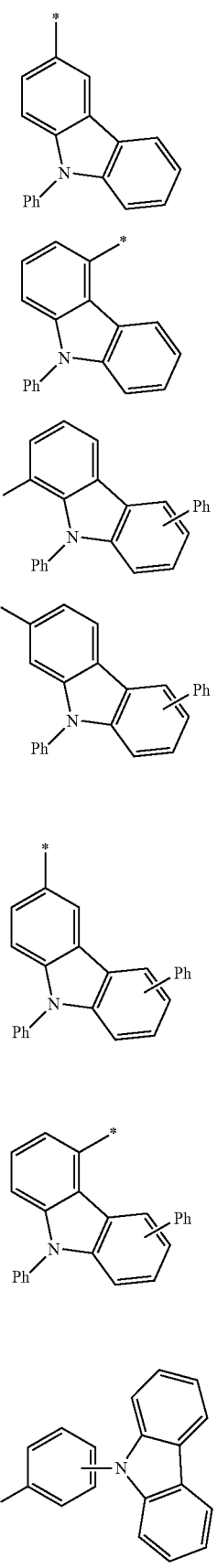
Formula 10-133
Formula 10-134
Formula 10-135
Formula 10-136
Formula 10-137
Formula 10-138
Formula 10-139

-continued
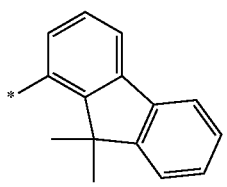
Formula 10-140
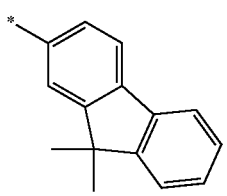
Formula 10-141
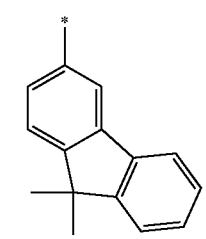
Formula 10-142
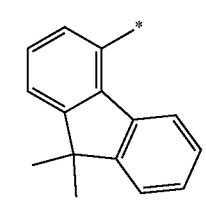
Formula 10-143
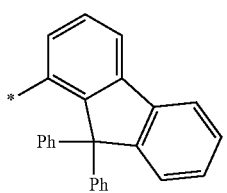
Formula 10-144
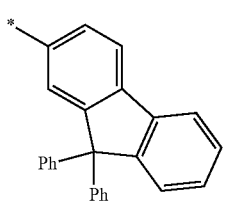
Formula 10-145
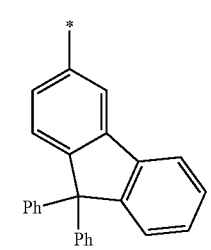
Formula 10-146
-continued
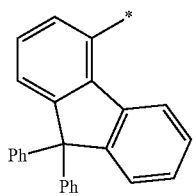
Formula 10-147
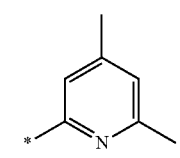
Formula 10-148
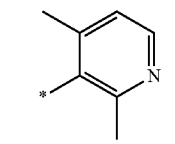
Formula 10-149
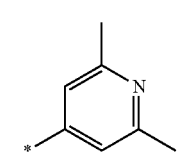
Formula 10-150
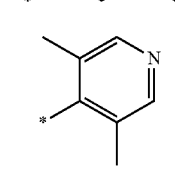
Formula 10-151
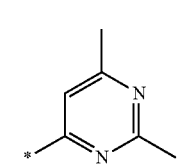
Formula 10-152
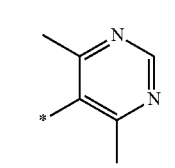
Formula 10-153
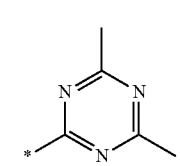
Formula 10-154
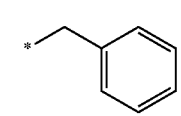
Formula 10-155
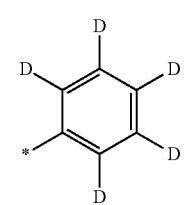
Formula 10-156

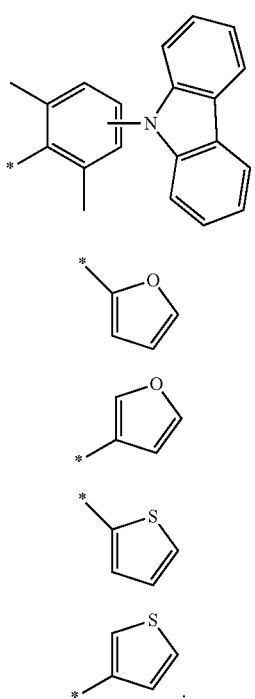

Formula 10-157

Formula 10-158

Formula 10-159

Formula 10-160

Formula 10-161

In Formulae 9-1 to 9-19 and 10-1 to 10-161, "Ph" indicates a phenyl group, "TMS" indicates a trimethylsilyl group, and * indicates a binding site to a neighboring atom.

In an embodiment, in Formula 1, $X_{31}$ may be $C(R_{31})$, $X_{32}$ may be $C(R_{32})$, and at least one of $R_{31}$ and $R_{32}$ may not be hydrogen.

In one or more embodiments, in Formula 1, $X_{31}$ may be $C(R_{31})$, $X_{32}$ may be $C(R_{32})$, and $R_{31}$ and $R_{32}$ may be identical to each other.

In one or more embodiments, in Formula 1, $X_{31}$ may be $C(R_{31})$, $X_{32}$ may be $C(R_{32})$, and at least one of $R_{31}$ and $R_{32}$ (for example, i) $R_{31}$ or ii) $R_{31}$ and $R_{32}$) may be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-B(Q_6)(Q_7)$, and $-P(=O)(Q_8)(Q_9)$ (for example, at least one of $R_{31}$ and $R_{32}$ may be selected from $-CH_3$, $-CD_3$, $-CD_2H$, $-CDH_2$, $-CF_3$, $-CF_2H$, $-CFH_2$, groups represented by Formulae 9-1 to 9-19, groups represented by Formulae 10-1 to 10-161, $-N(Q_1)(Q_2)$, $-Si(Q_3)(Q_4)(Q_5)$, $-B(Q_6)(Q_7)$, and $-P(=O)(Q_8)(Q_9)$).

In one or more embodiments, in Formula 1, $X_{31}$ may be $C(R_{31})$, $X_{32}$ may be $C(R_{32})$, and at least one of $R_{31}$ and $R_{32}$ (for example, i) $R_{31}$ or ii) $R_{31}$ and $R_{32}$) may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group (for example, at least one of $R_{31}$ and $R_{32}$ may be selected from groups represented by Formulae 10-1 to 10-161).

In one or more embodiments, in Formula 1, $X_{31}$ may be $C(R_{31})$, and $R_{31}$ may be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_6)$, $-B(Q_6)(Q_7)$, and $-P(=O)(Q_8)(Q_9)$ (for example, $R_{31}$ may be selected from $-CH_3$, $-CD_3$, $-CD_2H$, $-CDH_2$, $-CF_3$, $-CF_2H$, $-CFH_2$, groups represented by Formulae 9-1 to 9-19, groups represented by Formulae 10-1 to 10-161, $-N(Q_1)(Q_2)$, $-Si(Q_3)(Q_4)(Q_5)$, $-B(Q_6)(Q_7)$, and $-P(=O)(Q_8)(Q_9)$).

a1, a2, a3, and a4 respectively indicate the number of groups $R_1$, the number of groups $R_2$, the number of groups $R_3$, and the number of groups $R_4$, and may each independently be an integer from 0 to 20 (for example, an integer from 0 to 4). When a1 is two or more, two or more groups $R_1$ may be identical to or different from each other, when a2 is two or more, two or more groups $R_2$ may be identical to or different from each other, when a3 is two or more, two or more groups $R_3$ may be identical to or different from each other, and when a4 is two or more, two or more groups $R_4$ may be identical to or different from each other.

In an embodiment, $A_1$ in Formula 1 may be selected from moieties represented by Formulae CY1-1 to CY1-44 and A1-1 to A1-4:

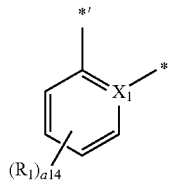

Formula CY1-1

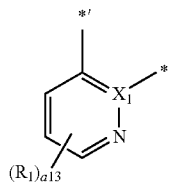

Formula CY1-2

Formula CY1-3

Formula CY1-4

Formula CY1-5

Formula CY1-6

Formula CY1-7

Formula CY1-8

Formula CY1-9

Formula CY1-10

Formula CY1-11

Formula CY1-12

Formula CY1-13

Formula CY1-14

Formula CY1-15

Formula CY1-16
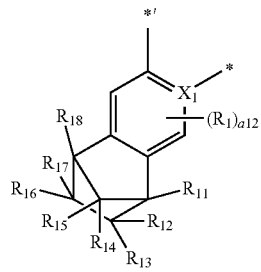
Formula CY1-17
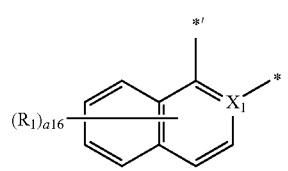
Formula CY1-18
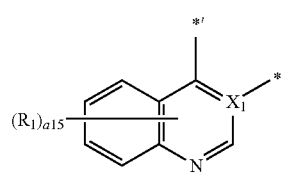
Formula CY1-19
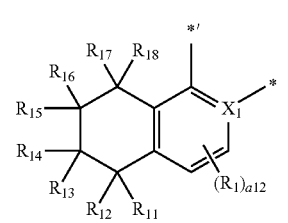
Formula CY1-20
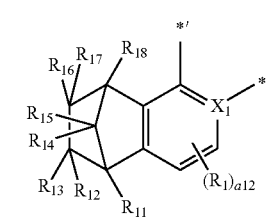
Formula CY1-21
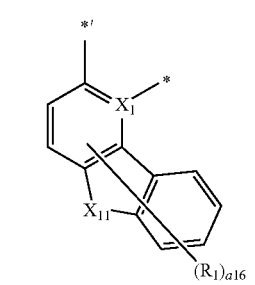
Formula CY1-22
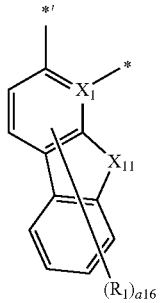
Formula CY1-23
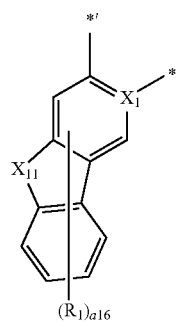
Formula CY1-24
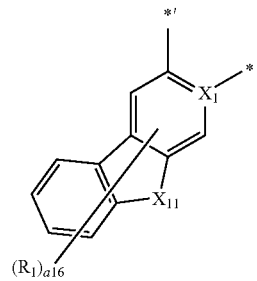
Formula CY1-25
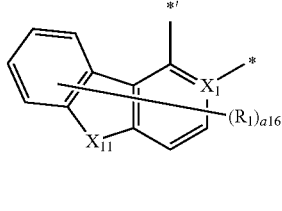
Formula CY1-26
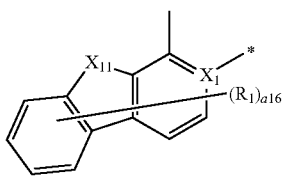
Formula CY1-27

Formula CY1-28
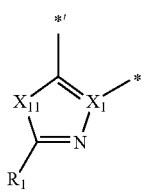
Formula CY1-29
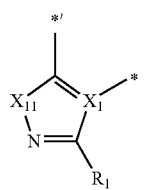
Formula CY1-30
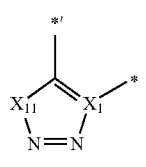
Formula CY1-31
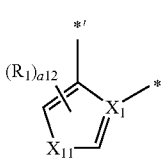
Formula CY1-32
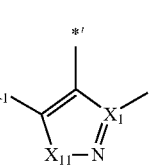
Formula CY1-33
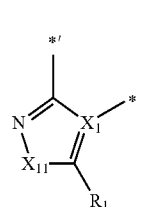
Formula CY1-34
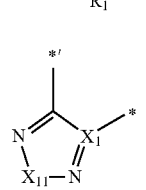
Formula CY1-35
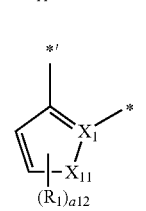
Formula CY1-36
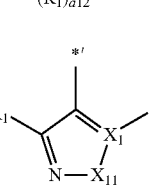
Formula CY1-37
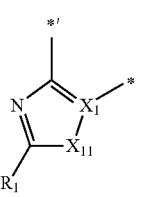
Formula CY1-38
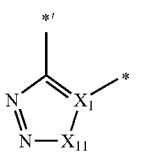
Formula CY1-39
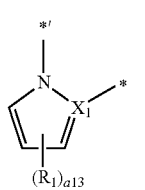
Formula CY1-40
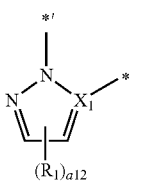
Formula CY1-41
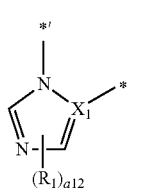
Formula CY1-42
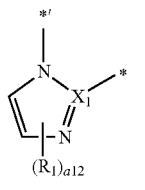
Formula CY1-43
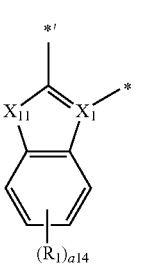

Formula CY1-44

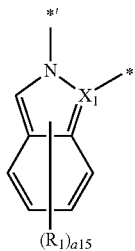

Formula A1-1

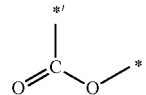

Formula A1-2

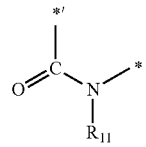

Formula A1-3

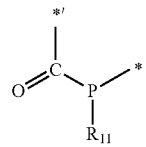

Formula A1-4

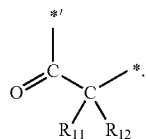

In Formulae CY1-1 to CY1-44 and A1-1 to A1-4,
$X_1$ and $R_1$ are the same as described herein,
$X_{11}$ may be O, S, N($R_{11}$), C($R_{11}$)($R_{12}$), or Si($R_{11}$)($R_{12}$),
$R_{11}$ to $R_{18}$ are the same as described in connection with $R_1$,
a16 may be an integer from 0 to 6,
a15 may be an integer from 0 to 5,
a14 may be an integer from 0 to 4,
a13 may be an integer from 0 to 3,
a12 may be an integer from 0 to 2,
* indicates a binding site to M in Formula 1, and
*' indicates a binding site to ring $CY_2$ in Formula 1.

In one or more embodiments, a moiety represented by

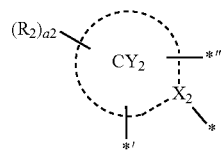

in Formula 1 may be represented by one of Formulae CY2-1 to CY2-45:

Formula CY2-1

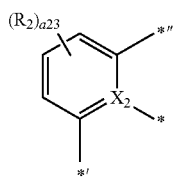

Formula CY2-2

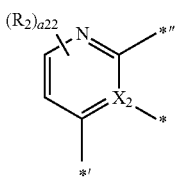

Formula CY2-3

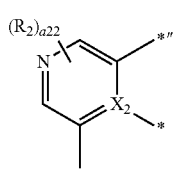

Formula CY2-4

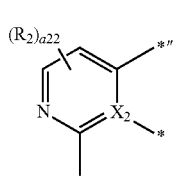

Formula CY2-5

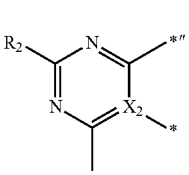

Formula CY2-6

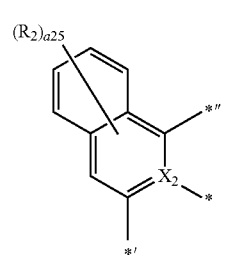

Formula CY2-7

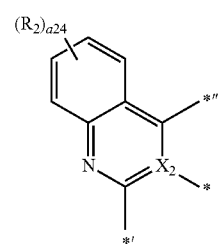

Formula CY2-8
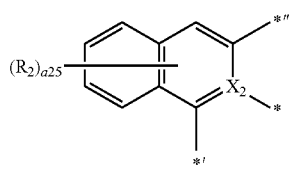
Formula CY2-9
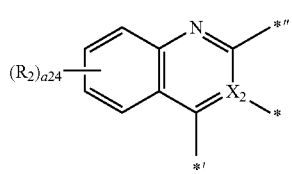
Formula CY2-10
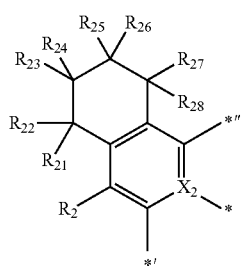
Formula CY2-11
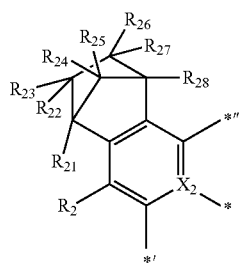
Formula CY2-12
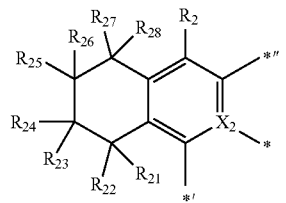
Formula CY2-13
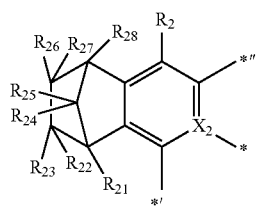
Formula CY2-14
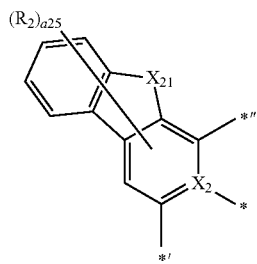
Formula CY2-15
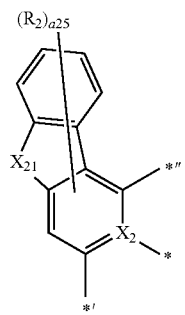
Formula CY2-16
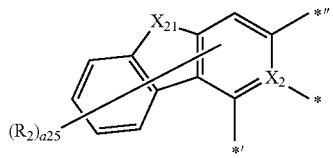
Formula CY2-17
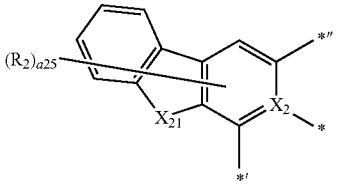
Formula CY2-18
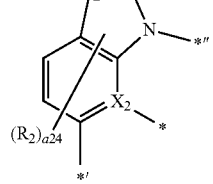
Formula CY2-19
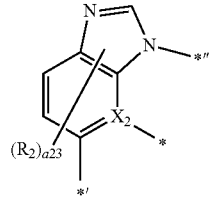
Formula CY2-20
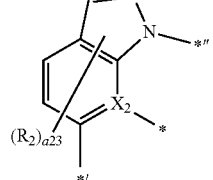
Formula CY2-21
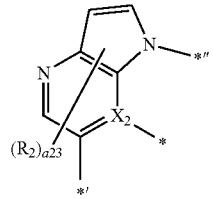

-continued

Formula CY2-22

Formula CY2-23

Formula CY2-24

Formula CY2-25

Formula CY2-26

-continued

Formula CY2-27

Formula CY2-28

Formula CY2-29

Formula CY2-30

Formula CY2-31

Formula CY2-32

Formula CY2-33
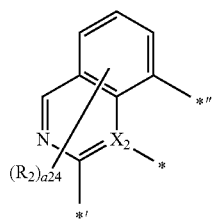

Formula CY2-34
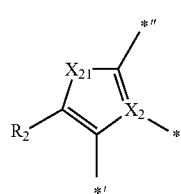

Formula CY2-35
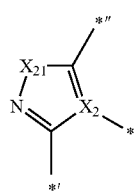

Formula CY2-36
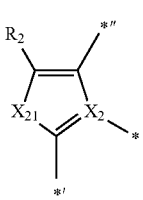

Formula CY2-37
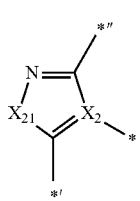

Formula CY2-38
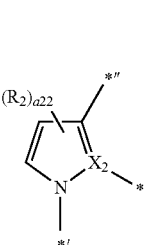

Formula CY2-39
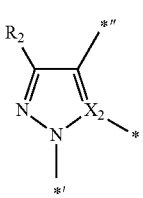

Formula CY2-40
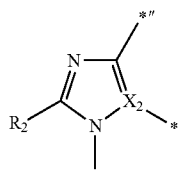

Formula CY2-41
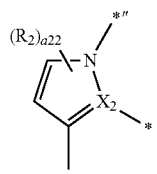

Formula CY2-42
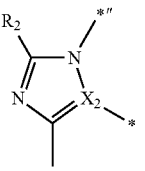

Formula CY2-43
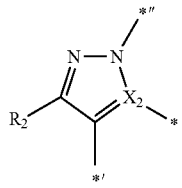

Formula CY2-44
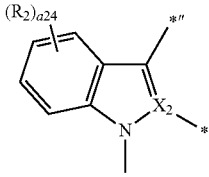

Formula CY2-45
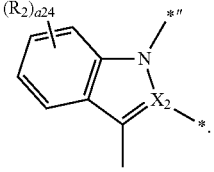

In Formulae CY2-1 to CY2-45, $X_2$ and $R_2$ are the same as described herein, $X_{21}$ may be O, S, $N(R_{21})$, $C(R_{21})(R_{22})$, or $Si(R_{21})(R_{22})$, $R_{21}$ to $R_{28}$ are the same as described in connection with $R_2$, a26 may be an integer from 0 to 6, a25 may be an integer from 0 to 5, a24 may be an integer from 0 to 4, a23 may be an integer from 0 to 3, a22 may be an integer from 0 to 2, \* indicates a binding site to M in Formula 1, \*' indicates a binding site to $A_1$ in Formula 1, and \*" indicates a binding site to $T_1$ in Formula 1.

In one or more embodiments, a moiety represented by

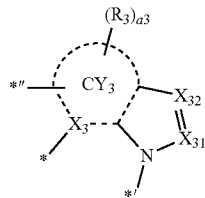

in Formula 1 may be represented by one of Formulae CY3-1 to CY3-10:

Formula CY3-1
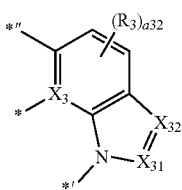

Formula CY3-2
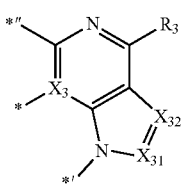

Formula CY3-3
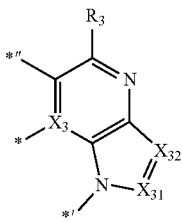

Formula CY3-4
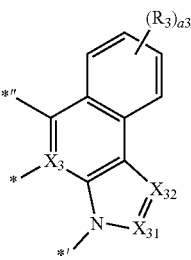

Formula CY3-5
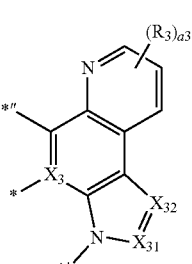

Formula CY3-6
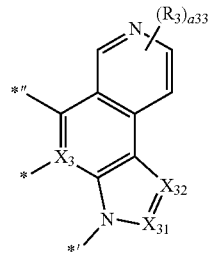

Formula CY3-7
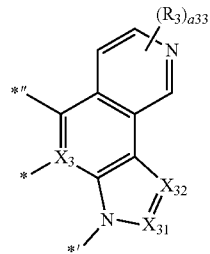

Formula CY3-8
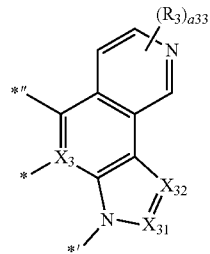

Formula CY3-9
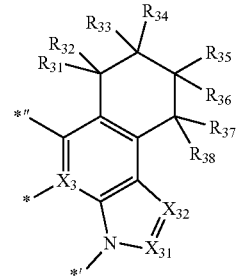

Formula CY3-10
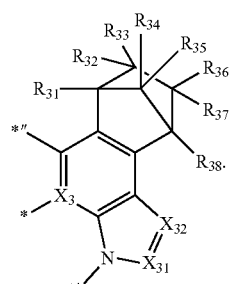

In Formulae CY3-1 to CY3-10, $X_3$, $R_3$, $X_{31}$, and $X_{32}$ are the same as described herein, $R_{31}$ to $R_{38}$ are the same as described in connection with $R_3$, a34 may be an integer from 0 to 4, a33 may be an integer from 0 to 3, a32 may be an integer from 0 to 2,

* indicates a binding site to M in Formula 1,

*″ indicates a binding site to $T_1$ in Formula 1, and

*′ indicates a binding site to $T_2$ in Formula 1.

In one or more embodiments, a moiety represented by
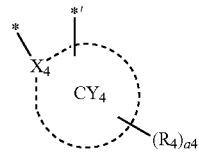
in Formula 1 may be represented by one of Formulae CY4-1 to CY4-44:
Formula CY4-1
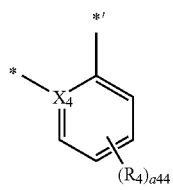
Formula CY4-2
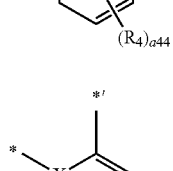
Formula CY4-3
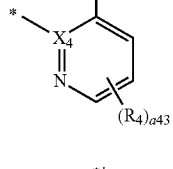
Formula CY4-4
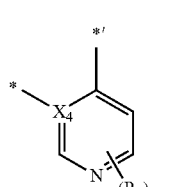
Formula CY4-5
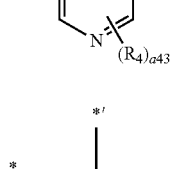
Formula CY4-6
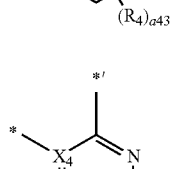
Formula CY4-7
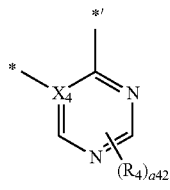
Formula CY4-8
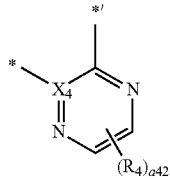
Formula CY4-9
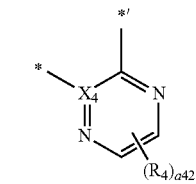
Formula CY4-10
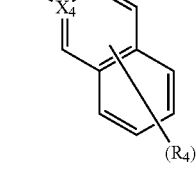
Formula CY4-11
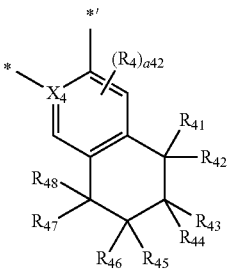
Formula CY4-12
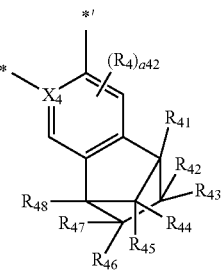

Formula CY4-13
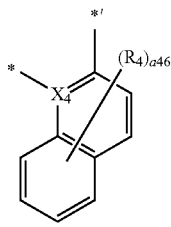
Formula CY4-14
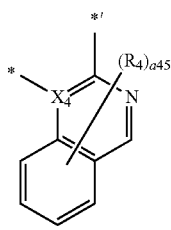
Formula CY4-15
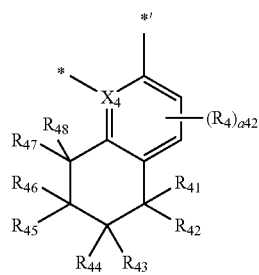
Formula CY4-16
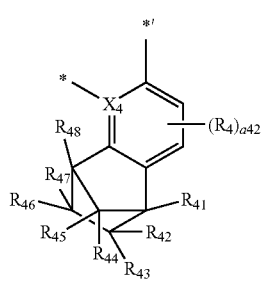
Formula CY4-17
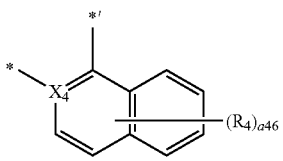
Formula CY4-18
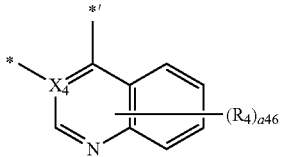
Formula CY4-19
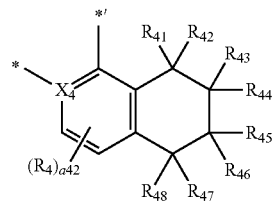
Formula CY4-20
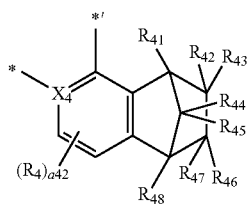
Formula CY4-21
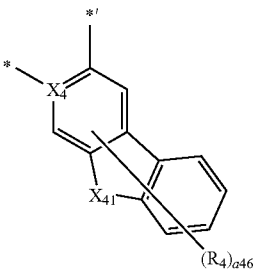
Formula CY4-22
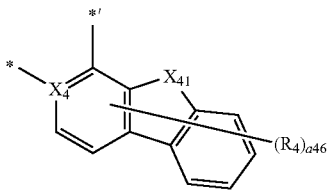
Formula CY4-23
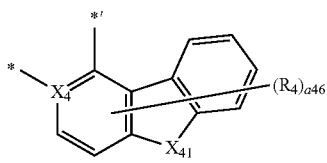
Formula CY4-24
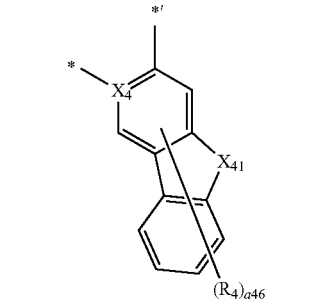
Formula CY4-25

-continued
Formula CY4-26
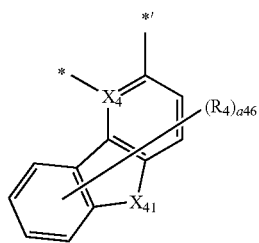
Formula CY4-27
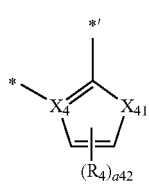
Formula CY4-28
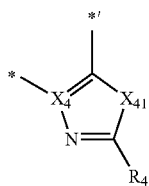
Formula CY4-29
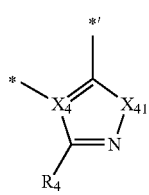
Formula CY4-30
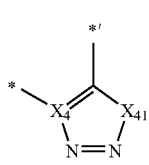
Formula CY4-31
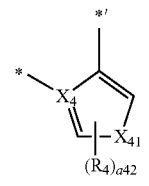
Formula CY4-32
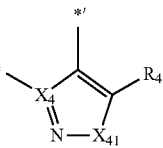
Formula CY4-33
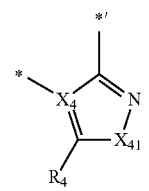
Formula CY4-34
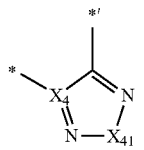
Formula CY4-35
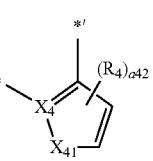
Formula CY4-36
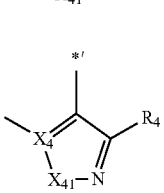
Formula CY4-37
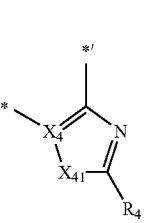
Formula CY4-38
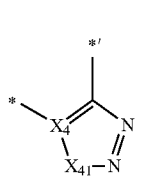
Formula CY4-39
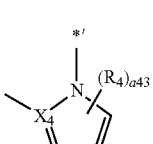
Formula CY4-40
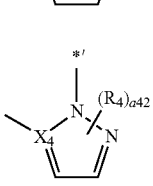
Formula CY4-41
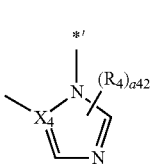
Formula CY4-42
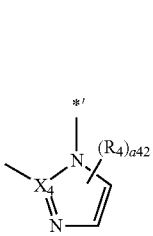

Formula CY4-43

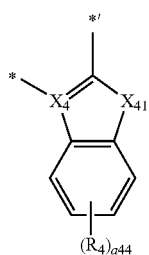

Formula CY4-44

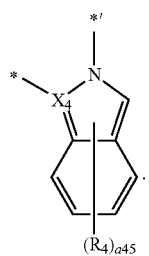

In Formulae CY4-1 to CY4-44, $X_4$ and $R_4$ are the same as described herein, $X_{41}$ may be O, S, $N(R_{41})$, $C(R_{41})(R_{42})$, or $Si(R_{41})(R_{42})$, $R_{41}$ to $R_{48}$ are the same as described in connection with $R_4$, a46 may be an integer from 0 to 6, a45 may be an integer from 0 to 5, a44 may be an integer from 0 to 4, a43 may be an integer from 0 to 3, a42 may be an integer from 0 to 2, \* indicates a binding site to M in Formula 1, and \*' indicates a binding site to $T_2$ in Formula 1.

In one or more embodiments, in Formula 1, $A_1$ may be selected from moieties represented by Formulae CY1(1) to CY1(19), and/or the moiety represented by

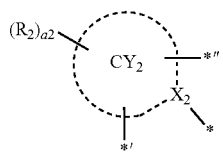

may be represented by one of Formulae CY2(1) to CY2(13), and/or the moiety represented by

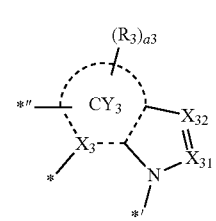

may be represented by one of Formulae CY3(1) to CY3(18), and/or the moiety represented by

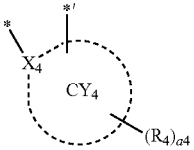

may be represented by one of Formulae CY4(1) to CY4(11):

Formula CY1(1)

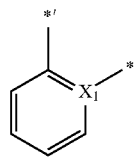

Formula CY1(2)

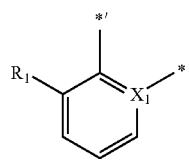

Formula CY1(3)

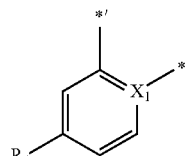

Formula CY1(4)

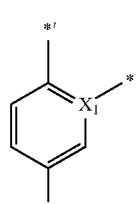

Formula CY1(5)

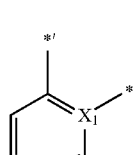

Formula CY1(6)

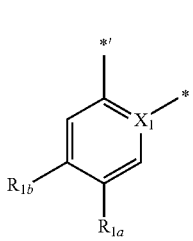

-continued
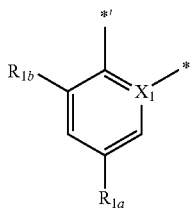
Formula CY1(7)
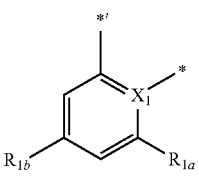
Formula CY1(8)
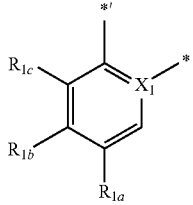
Formula CY1(9)
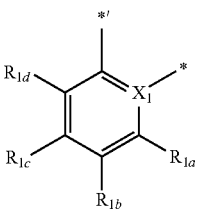
Formula CY1(10)
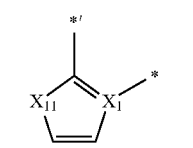
Formula CY1(11)
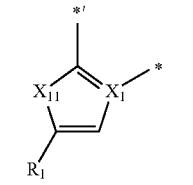
Formula CY1(12)
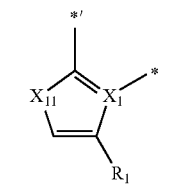
Formula CY1(13)
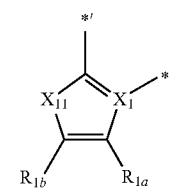
Formula CY1(14)
-continued
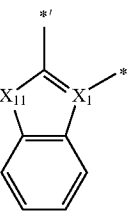
Formula CY1(15)
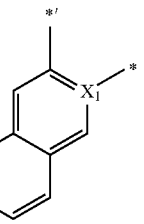
Formula CY1(16)
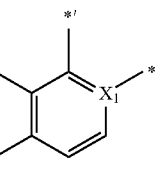
Formula CY1(17)
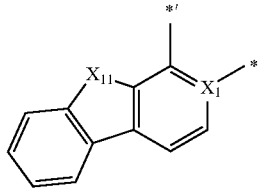
Formula CY1(18)
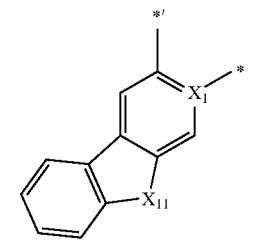
Formula CY1(19)
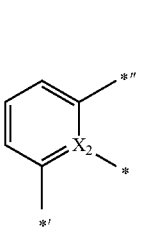
Formula CY2(1)
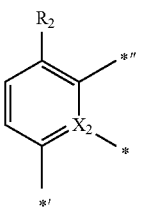
Formula CY2(2)

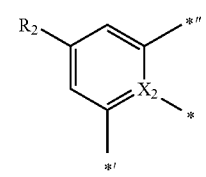
Formula CY2(3)
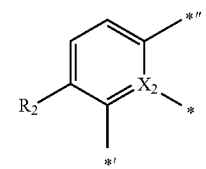
Formula CY2(4)
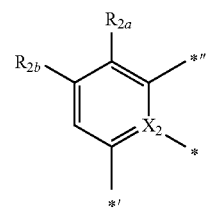
Formula CY2(5)
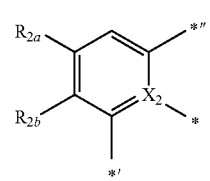
Formula CY2(6)
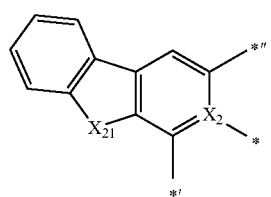
Formula CY2(7)
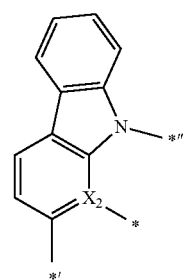
Formula CY2(8)
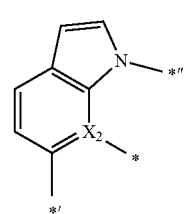
Formula CY2(9)
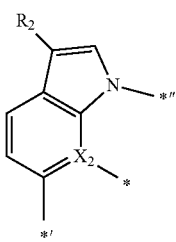
Formula CY2(10)
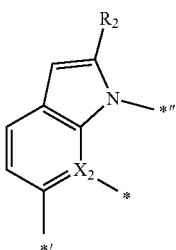
Formula CY2(11)
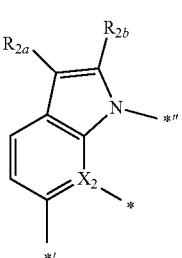
Formula CY2(12)
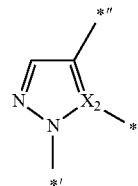
Formula CY2(13)
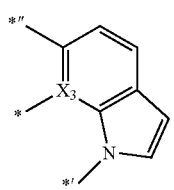
Formula CY3(1)
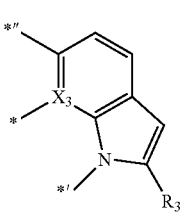
Formula CY3(2)
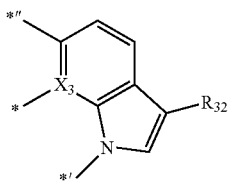
Formula CY3(3)

-continued
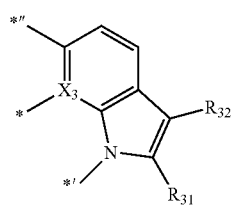
Formula CY3(4)
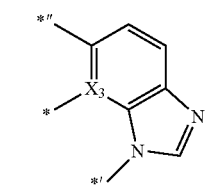
Formula CY3(5)
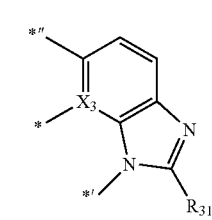
Formula CY3(6)
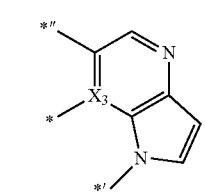
Formula CY3(7)
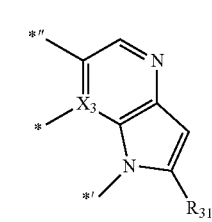
Formula CY3(8)
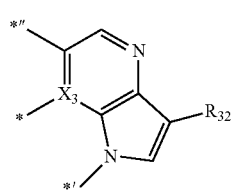
Formula CY3(9)
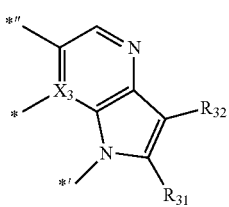
Formula CY3(10)
-continued
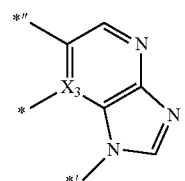
Formula CY3(11)
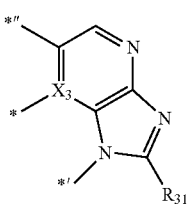
Formula CY3(12)
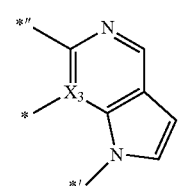
Formula CY3(13)
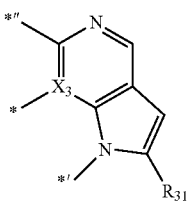
Formula CY3(14)
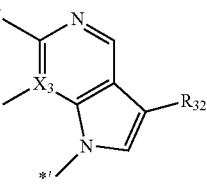
Formula CY3(15)
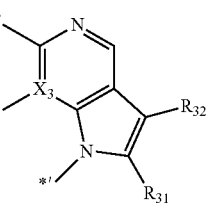
Formula CY3(16)
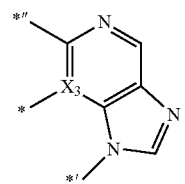
Formula CY3(17)

Formula CY3(18)
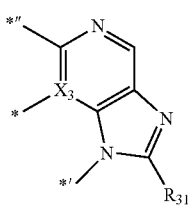

Formula CY4(1)
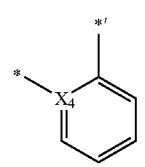

Formula CY4(2)
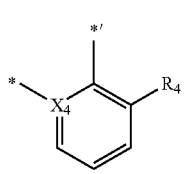

Formula CY4(3)
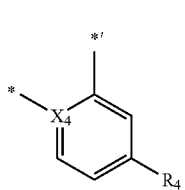

Formula CY4(4)
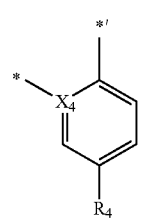

Formula CY4(5)
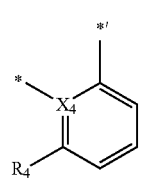

Formula CY4(6)
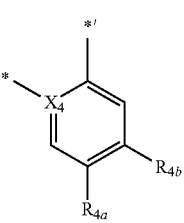

Formula CY4(7)
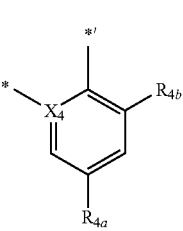

Formula CY4(8)
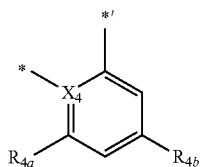

Formula CY4(9)
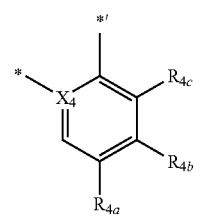

Formula CY4(10)
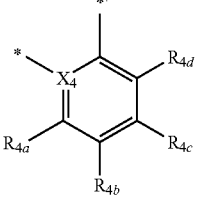

Formula CY4(11)
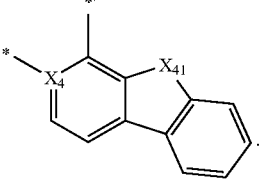

In Formulae CY1 (1) to CY1 (19), CY2(1) to CY2(13), CY3(1) to CY3(18), and CY4(1) to CY4(11), $X_1$ to $X_4$, $R_1$ to $R_4$, $R_{31}$, and $R_{32}$ are the same as described herein, $X_{11}$ may be O, S, N($R_{11}$), C($R_{11}$)($R_{12}$), or Si($R_{11}$)($R_{12}$), $X_{21}$ may be O, S, N($R_{21}$), C($R_{21}$)($R_{22}$), or Si($R_{21}$)($R_{22}$), $X_{41}$ may be O, S, N($R_{41}$), C($R_{41}$)($R_{42}$), or Si($R_{41}$)($R_{42}$), $R_{1a}$ to $R_{1d}$, $R_{11}$, and $R_{12}$ are the same as described in connection with $R_1$, $R_{2a}$, $R_{2b}$, $R_{21}$, and $R_{22}$ are the same as described in connection with $R_2$, $R_{4a}$ to $R_{4d}$, $R_{41}$, and $R_{42}$ are the same as described in connection with $R_4$, \* in Formulae CY1(1) to CY1(19), CY2(1) to CY2(13), CY3(1) to CY3(18), and CY4(1) to CY4(11) indicates a binding site to M in Formula 1, \*' in Formulae CY1(1) to CY1(19) indicates a binding site to ring CY2 in Formula \*' in Formulae CY2(1) to CY2(13) indicates a binding site to $A_1$ in Formula 1, \*" in Formulae CY2(1) to CY2(13) indicates a binding site to $T_1$ in Formula 1, \*" in Formulae CY3(1) to CY3(18) indicates a binding site to $T_1$ in Formula 1, \*' in Formulae CY3(1) to CY3(18) indicates a binding site to $T_2$ in Formula 1, and \*' in Formulae CY4(1) to CY4(11) indicates a binding site to $T_2$ in Formula 1.

In one or more embodiments, the organometallic compound represented by Formula 1 may be represented by Formula 1-1:

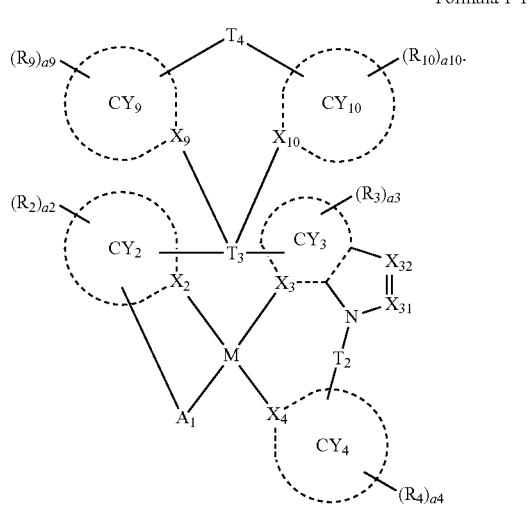

Formula 1-1

In Formula 1-1,

M, $A_1$, $X_2$ to $X_4$, $CY_2$ to $CY_4$, $X_{31}$, $X_{32}$, $T_2$, $R_2$ to $R_4$, and a2 to a4 are the same as described herein, $X_9$ and $X_{10}$ may each independently be C or N, $CY_9$ and $CY_{10}$ may each independently be selected from a $C_5$-$C_{30}$ carbocyclic group and a $C_1$-$C_{60}$ heterocyclic group (for example, $CY_9$ and $CY_{10}$ are the same as described in connection with $CY_1$), $R_9$ and $R_{10}$ are the same as described in connection with $R_1$, a9 and a10 are the same as described in connection with a1, $T_3$ may be C, Si, or Ge, $T_4$ may be selected from a single bond, a double bond, *—N($R_7$)—*', *—B($R_7$)—*', *—P($R_7$)—*', *—C($R_7$)($R_9$)—*', *—Si($R_7$)($R_9$)—*', *—Ge($R_7$)($R_9$)—*', *—S—*', *—Se—*', *—O—*', *—C(=O)—*', *—S(=O)—*', *—S(=O)$_2$—*', *—C($R_7$)=*', *=C($R_7$)—*', *—C($R_7$)=C($R_9$)—*', *—C(=S)—*', and *—C≡C—*', and * and *' each indicate a binding site to a neighboring atom, $R_7$ and $R_8$ are the same as described in connection with $R_5$, and

* and *' each indicate a binding site to a neighboring atom.

In Formula 1, i) two of a plurality of neighboring groups $R_1$ may optionally be linked to form a substituted or unsubstituted $C_5$-$C_{30}$ carbocyclic group or a substituted or unsubstituted $C_1$-$C_{30}$ heterocyclic group, ii) two of a plurality of neighboring groups $R_2$ may optionally be linked to form a substituted or unsubstituted $C_5$-$C_{30}$ carbocyclic group or a substituted or unsubstituted $C_1$-$C_{30}$ heterocyclic group, iii) two of a plurality of neighboring groups $R_3$ may optionally be linked to form a substituted or unsubstituted $C_5$-$C_{30}$ carbocyclic group or a substituted or unsubstituted $C_1$-$C_{30}$ heterocyclic group, iv) two of a plurality of neighboring groups $R_4$ may optionally be linked to form a substituted or unsubstituted $C_5$-$C_{30}$ carbocyclic group or a substituted or unsubstituted $C_1$-$C_{30}$ heterocyclic group, and v) two or more neighboring groups selected from $R_1$ to $R_4$ may optionally be linked to form a substituted or unsubstituted $C_5$-$C_{30}$ carbocyclic group or a substituted or unsubstituted $C_1$-$C_{30}$ heterocyclic group.

For example, i) a substituted or unsubstituted $C_5$-$C_{30}$ carbocyclic group or a substituted or unsubstituted $C_1$-$C_{30}$ heterocyclic group, formed by linking two of a plurality of neighboring groups $R_1$, ii) a substituted or unsubstituted $C_5$-$C_{30}$ carbocyclic group or a substituted or unsubstituted $C_1$-$C_{30}$ heterocyclic group, formed by linking two of a plurality of neighboring groups $R_2$, iii) a substituted or unsubstituted $C_5$-$C_{30}$ carbocyclic group or a substituted or unsubstituted $C_1$-$C_{30}$ heterocyclic group, formed by linking two of a plurality of neighboring groups $R_3$, iv) a substituted or unsubstituted $C_5$-$C_{30}$ carbocyclic group or a substituted or unsubstituted $C_1$-$C_{30}$ heterocyclic group, formed by linking two of a plurality of neighboring groups $R_4$, and v) a substituted or unsubstituted $C_5$-$C_{30}$ carbocyclic group or a substituted or unsubstituted $C_1$-$C_{30}$ heterocyclic group, formed by two or more neighboring groups selected from $R_1$ to $R_4$ in Formula 1, may each independently be selected from:

a cyclopentadiene group, a cyclohexane group, a cycloheptane group, an adamantane group, a bicycloheptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group; and a cyclopentadiene group, a cyclohexane group, a cycloheptane group, an adamantane group, a bicycloheptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group, each substituted with at least one $R_{10}$, but embodiments of the present disclosure are not limited thereto.

$R_{10}$ is the same as described in connection with $R_1$.

"An azabenzothiophene group, an azabenzofuran group, an azaindene group, an azaindole group, an azabenzosilole group, an azadibenzothiophene group, an azadibenzofuran group, an azafluorene group, an azacarbazole group, and an azadibenzosilole group" used herein mean hetero-rings that respectively have the same backbones as "a benzothiophene group, a benzofuran group, an indene group, an indole group, an benzosilole group, a dibenzothiophene group, a dibenzofuran group, a fluorene group, a carbazole group, and a dibenzosilole group", provided that at least one of carbons forming rings thereof is substituted with nitrogen.

For example, the organometallic compound may be one of Compounds 1 to 105, but embodiments of the present disclosure are not limited thereto:
1
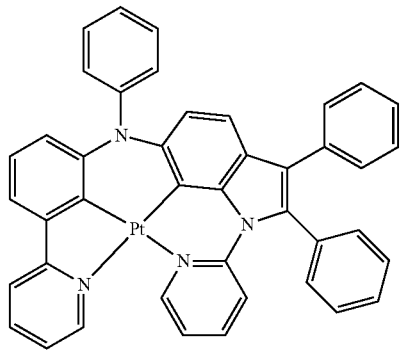
2
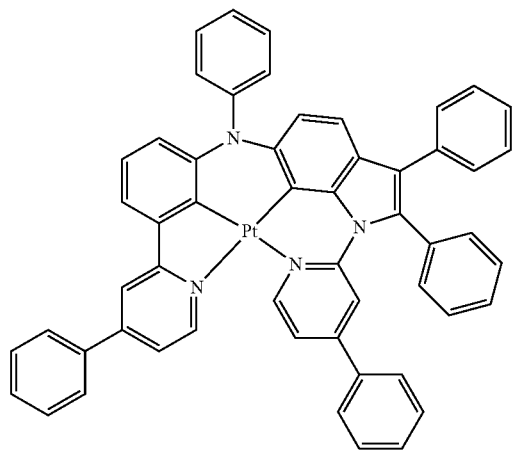
3
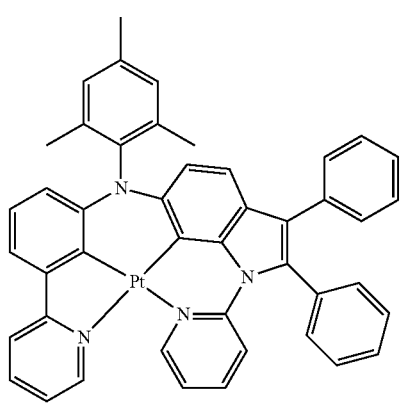
-continued
4
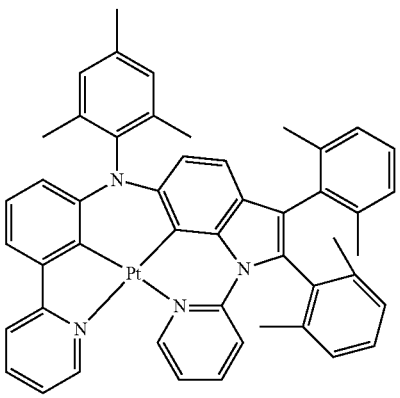
5
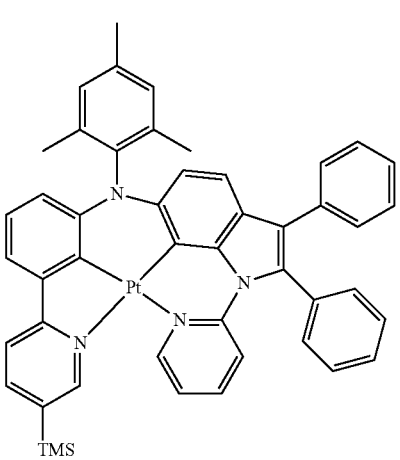
6
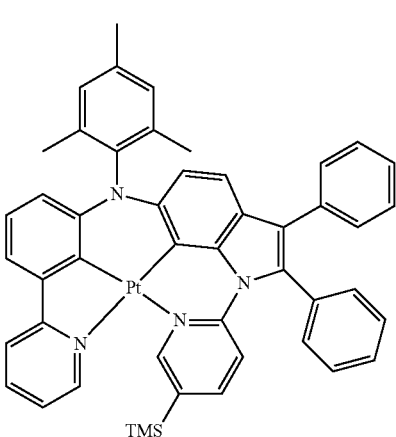

-continued
7
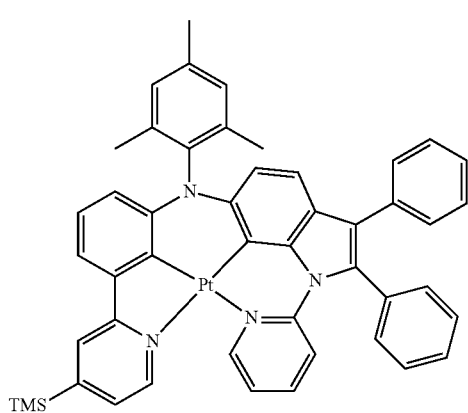
8
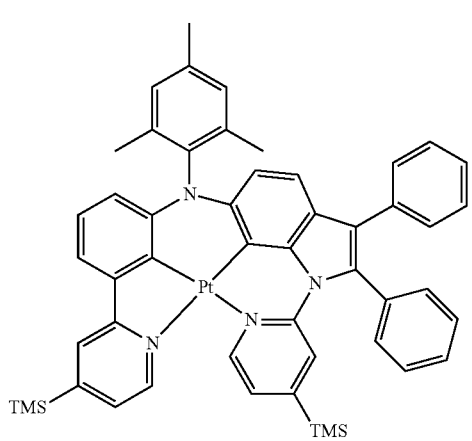
9
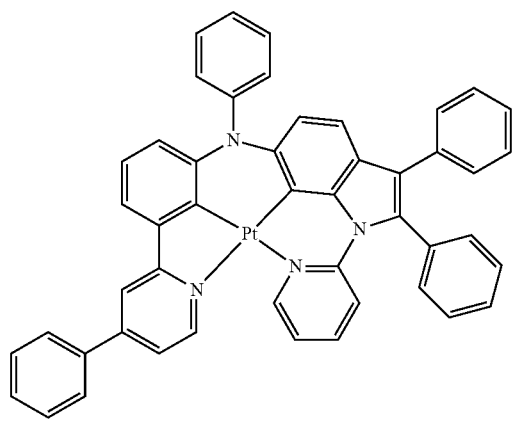
-continued
10
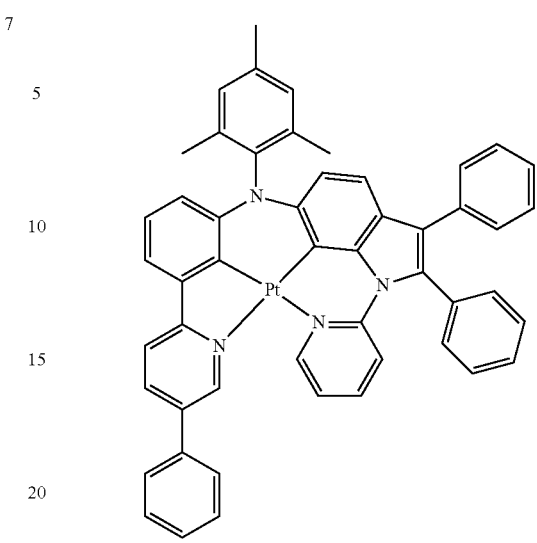
11
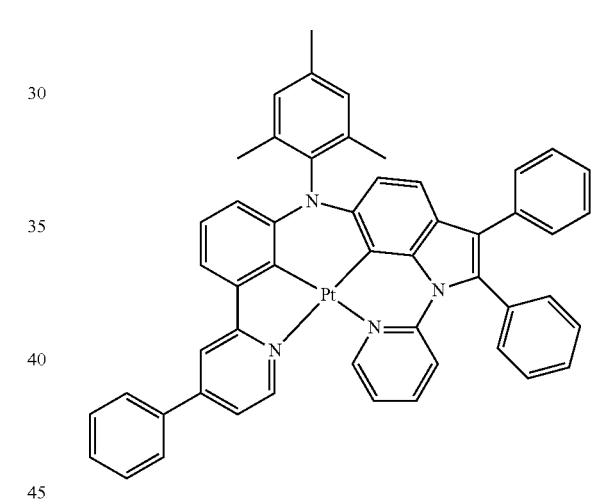
12
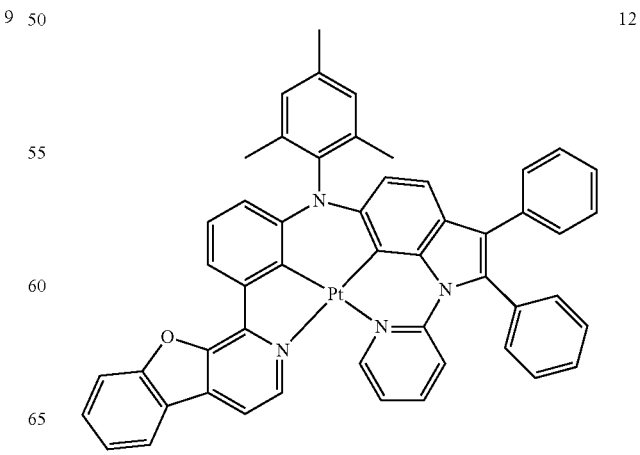

13
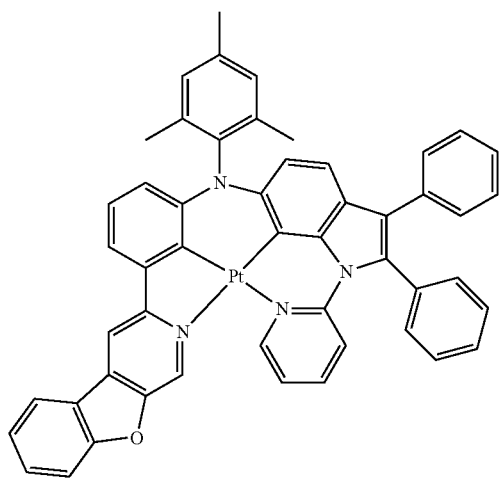
14
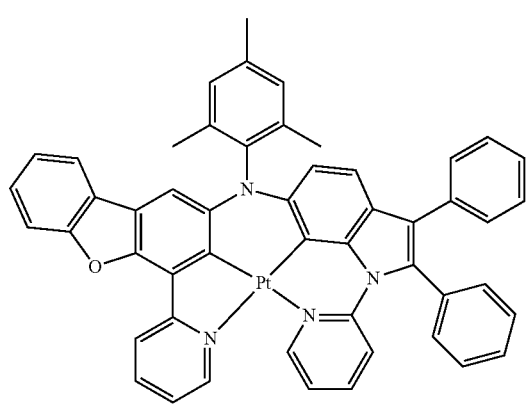
15
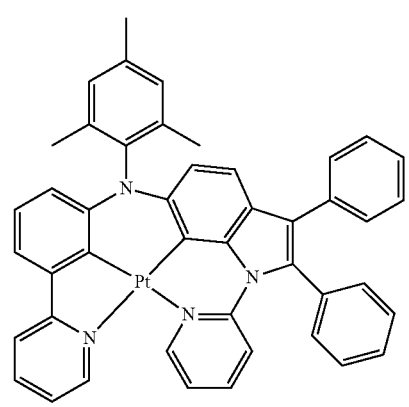
16
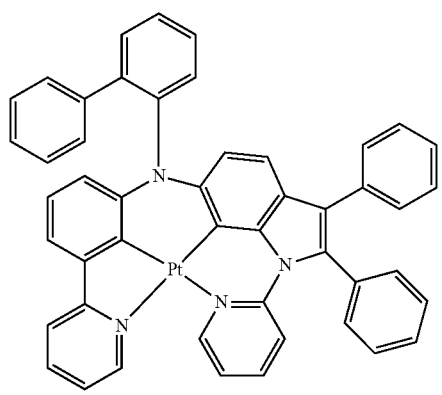
17
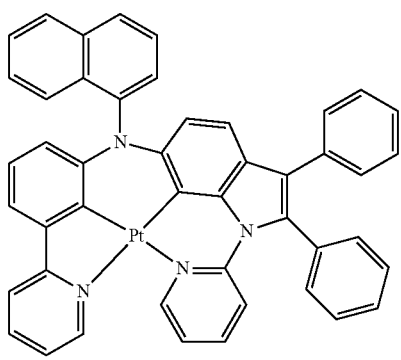
18
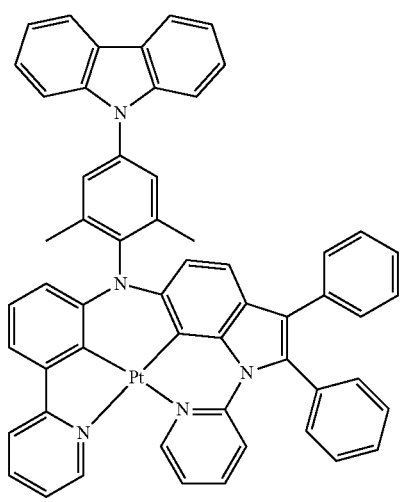

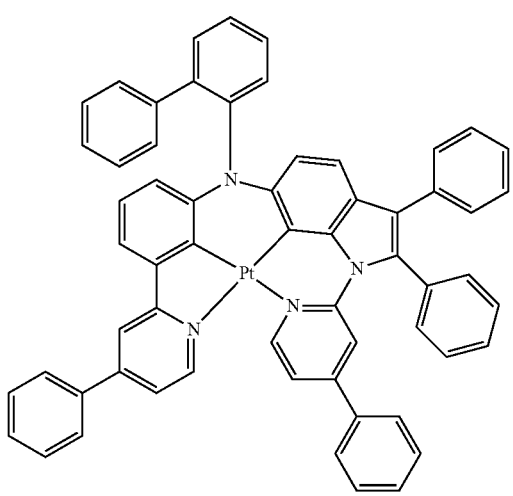
19
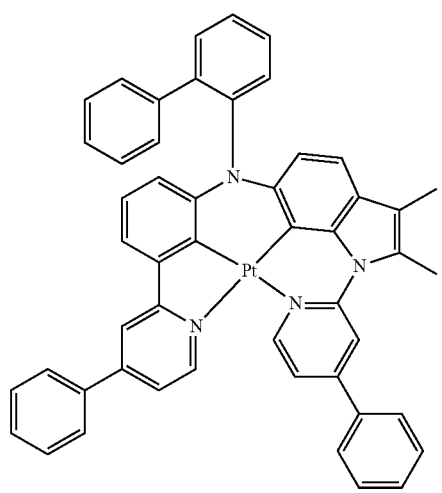
22
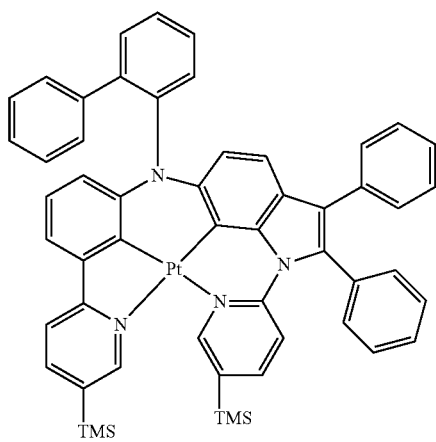
20
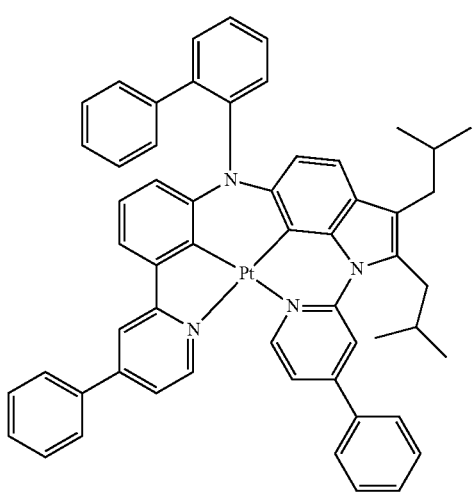
23
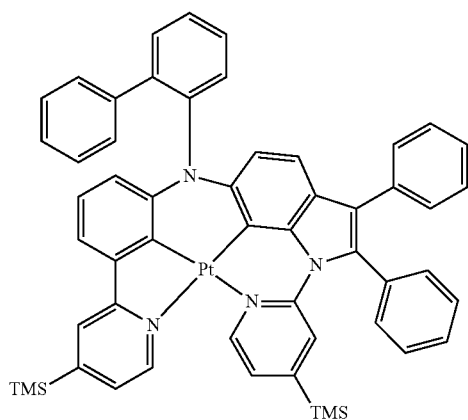
21
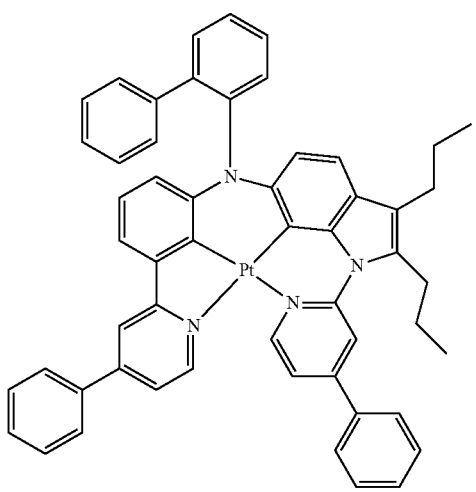
24

73
-continued
25
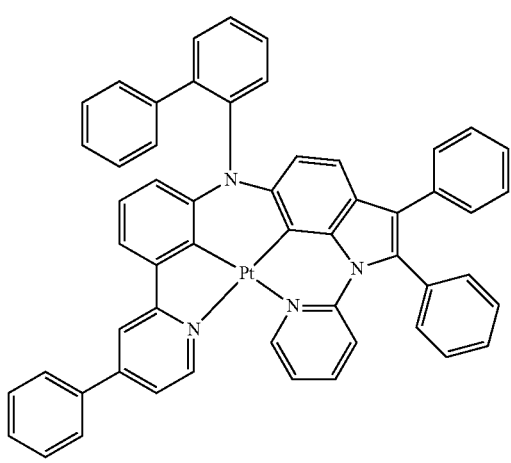
26
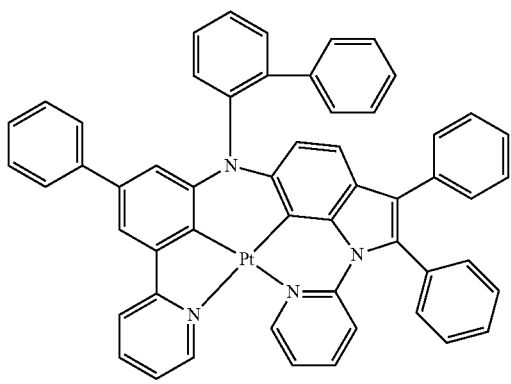
27
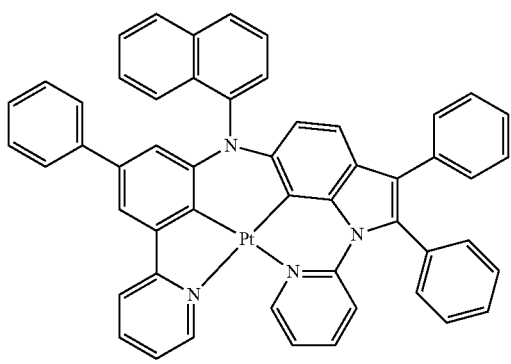
74
-continued
28
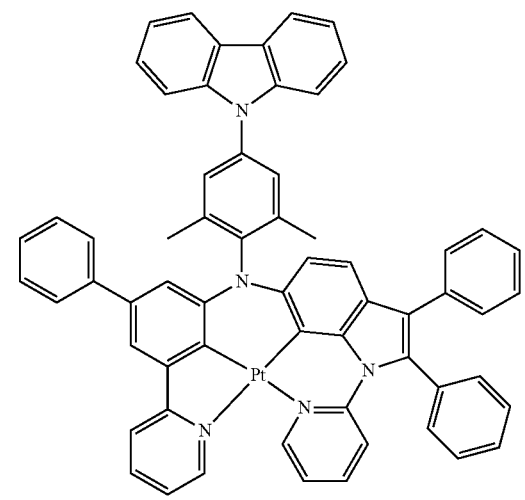
29
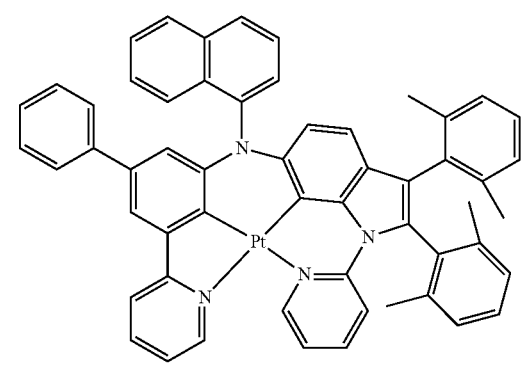
30

31
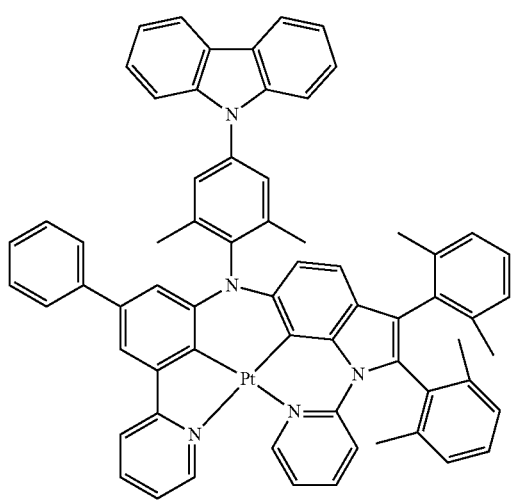
34
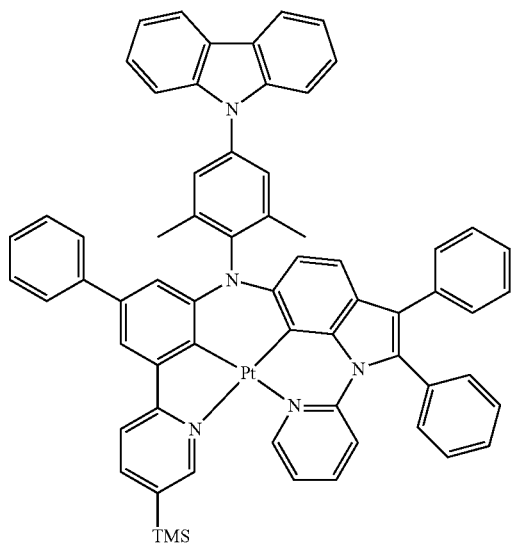
32
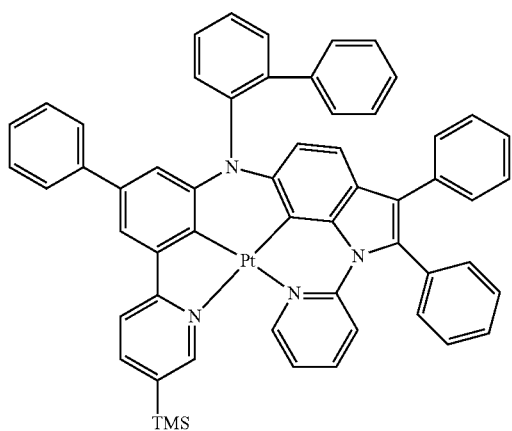
35
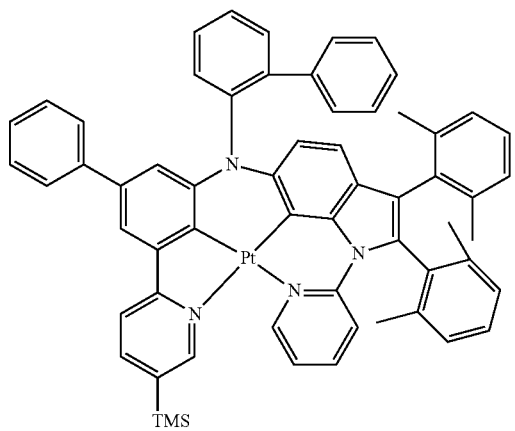
33
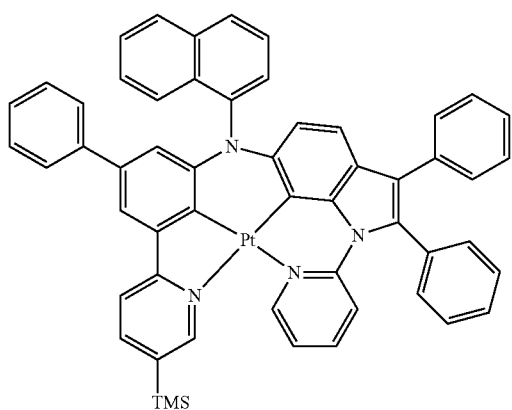
36
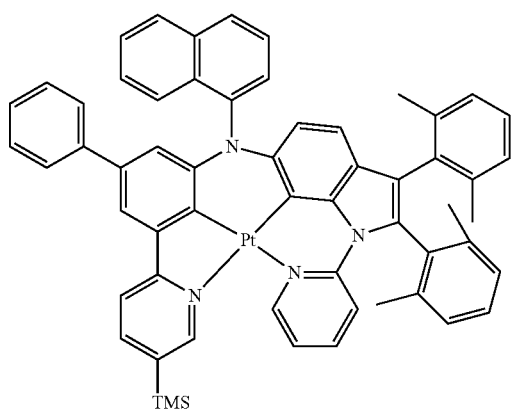

37
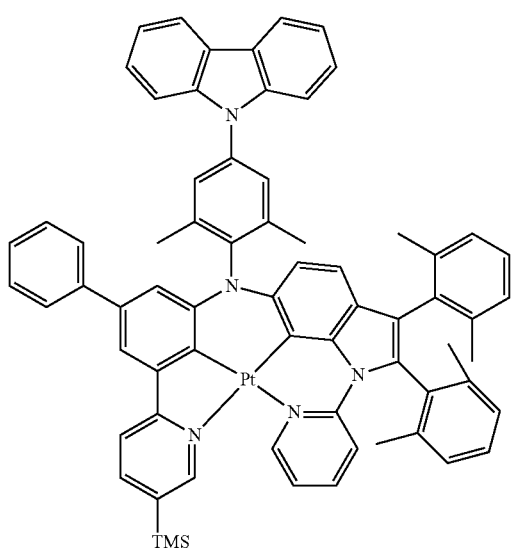
38
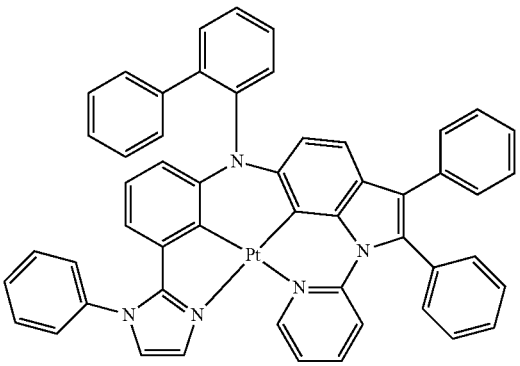
39
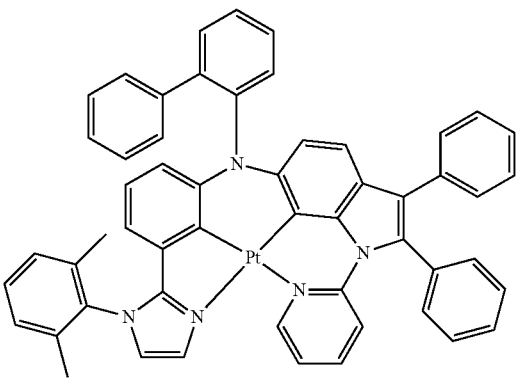
40
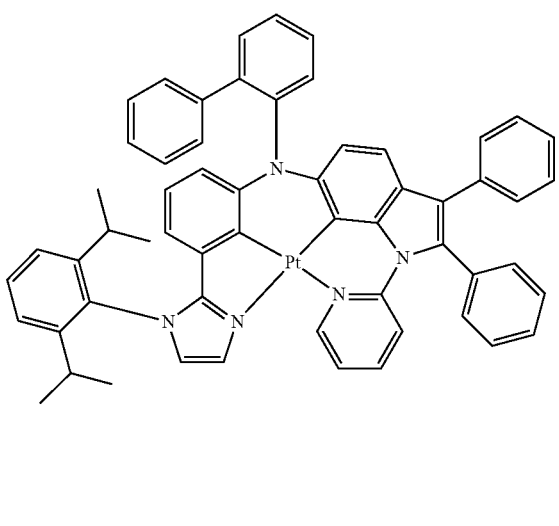
41
42
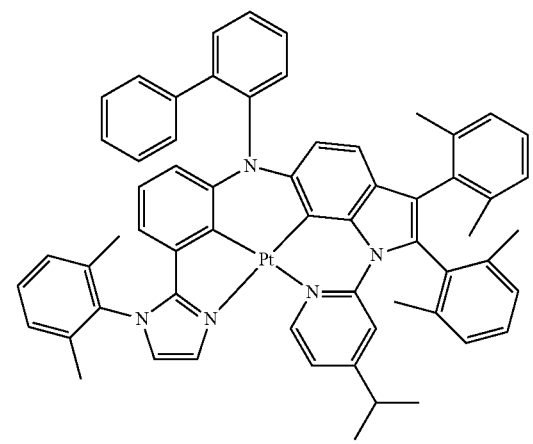

-continued
43
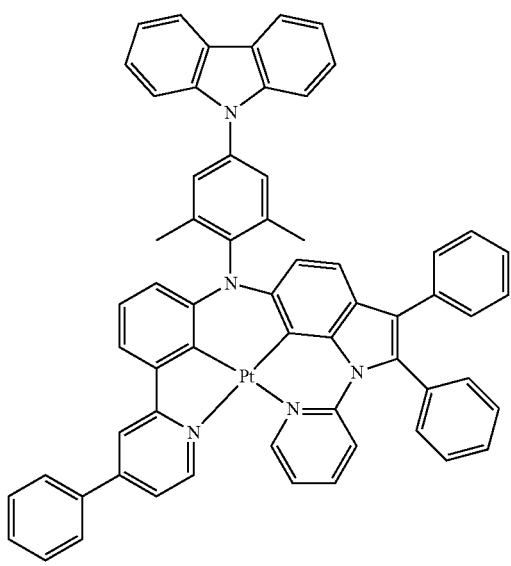
44
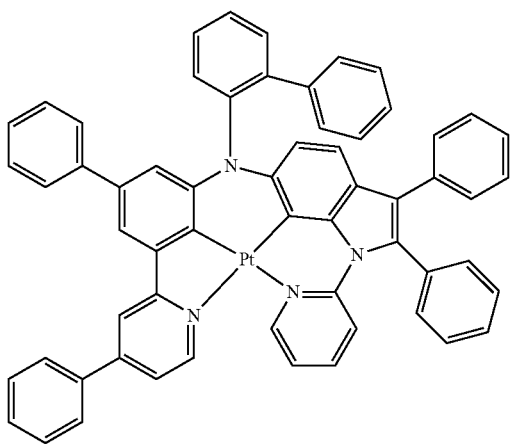
45
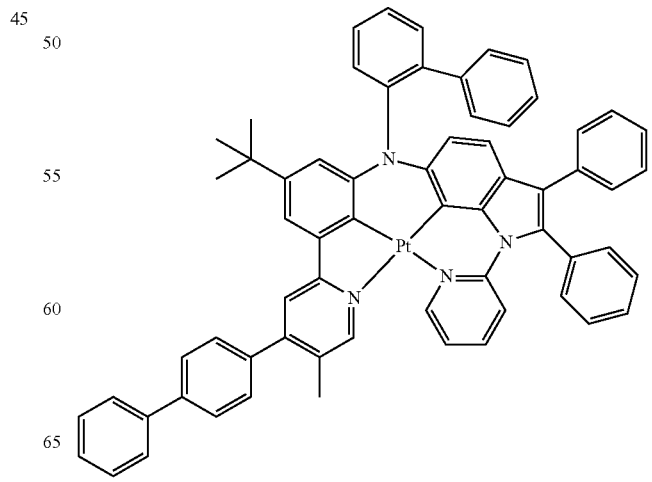
-continued
46
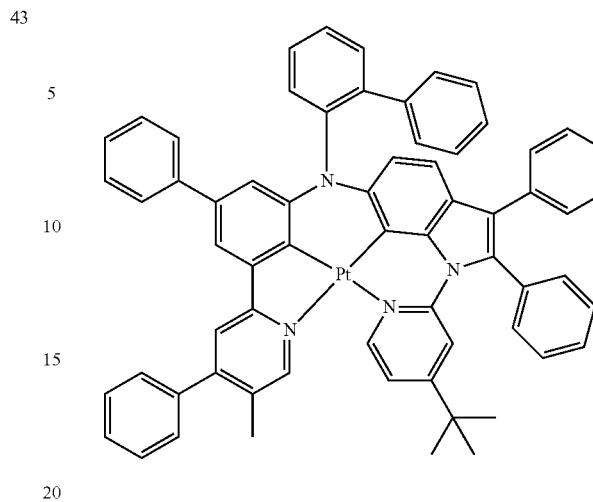
47
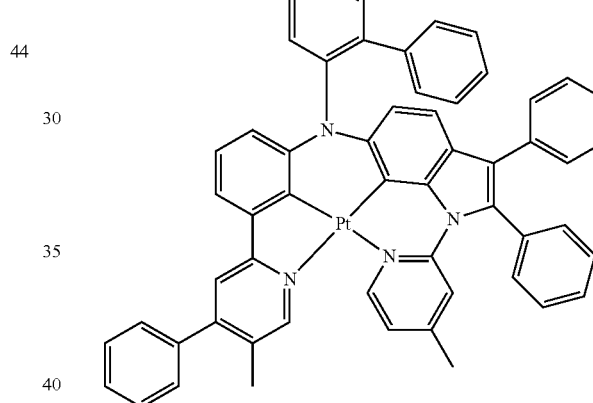
48

81
-continued
49
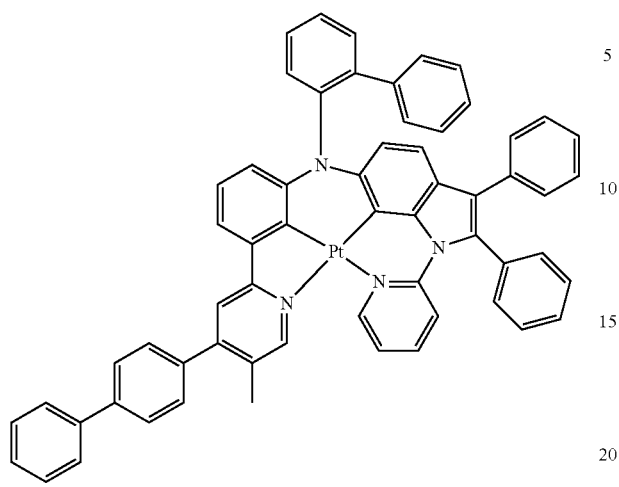
50
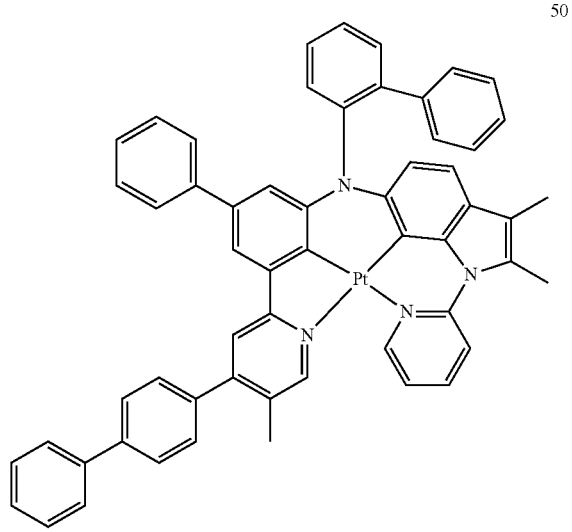
51
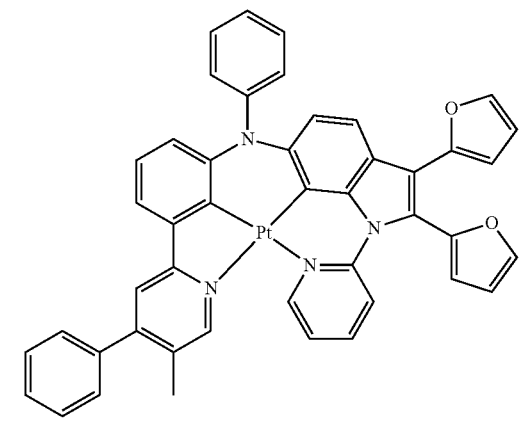
82
-continued
52
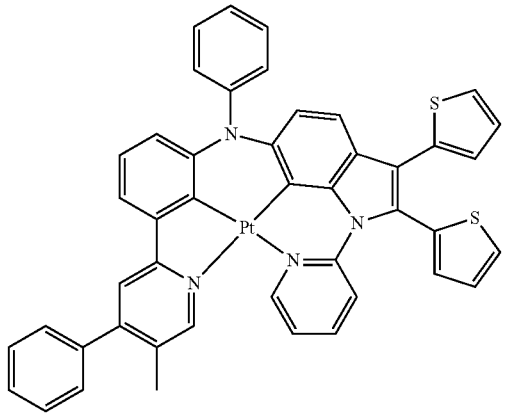
53
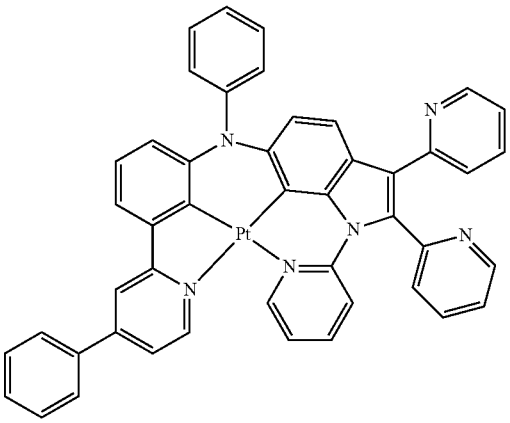
54
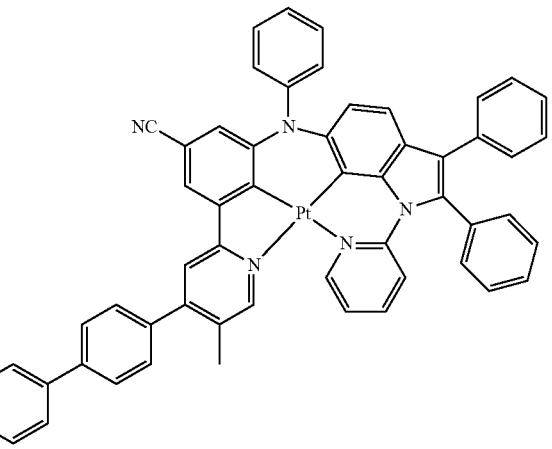

55
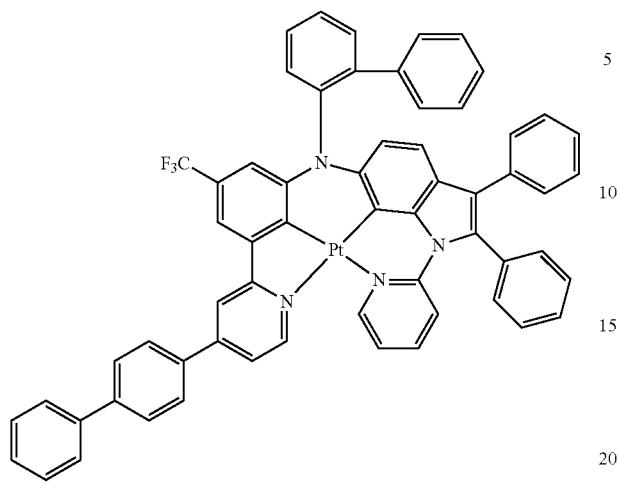
56
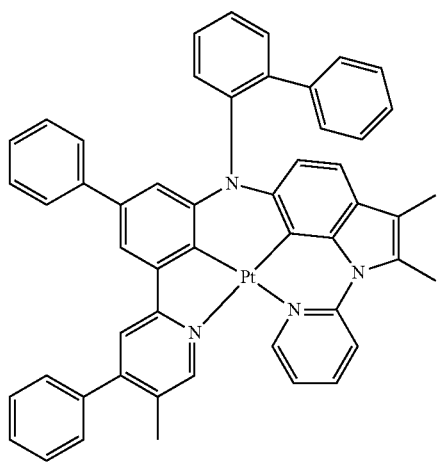
57
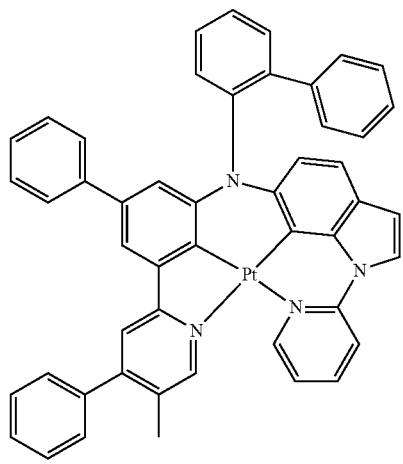
58
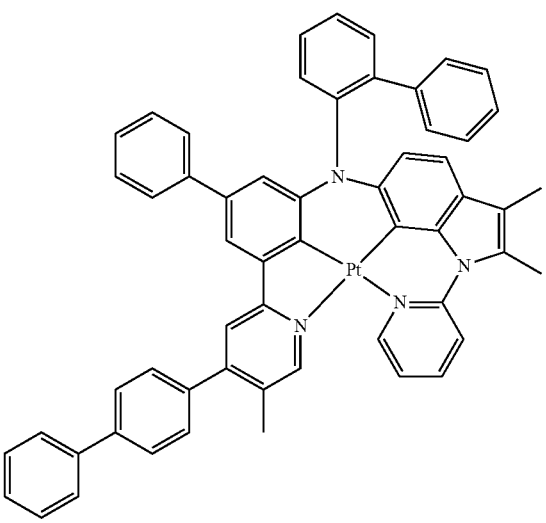
59
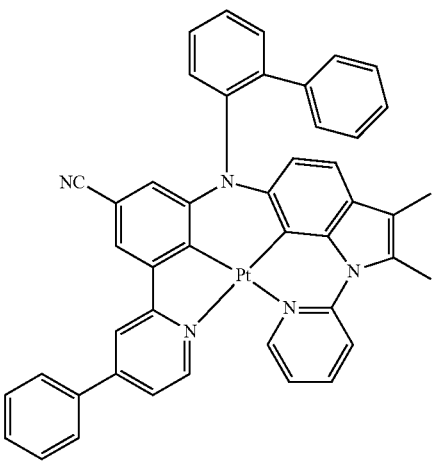
60
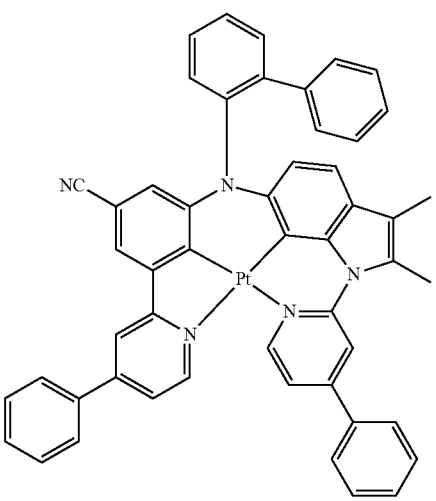

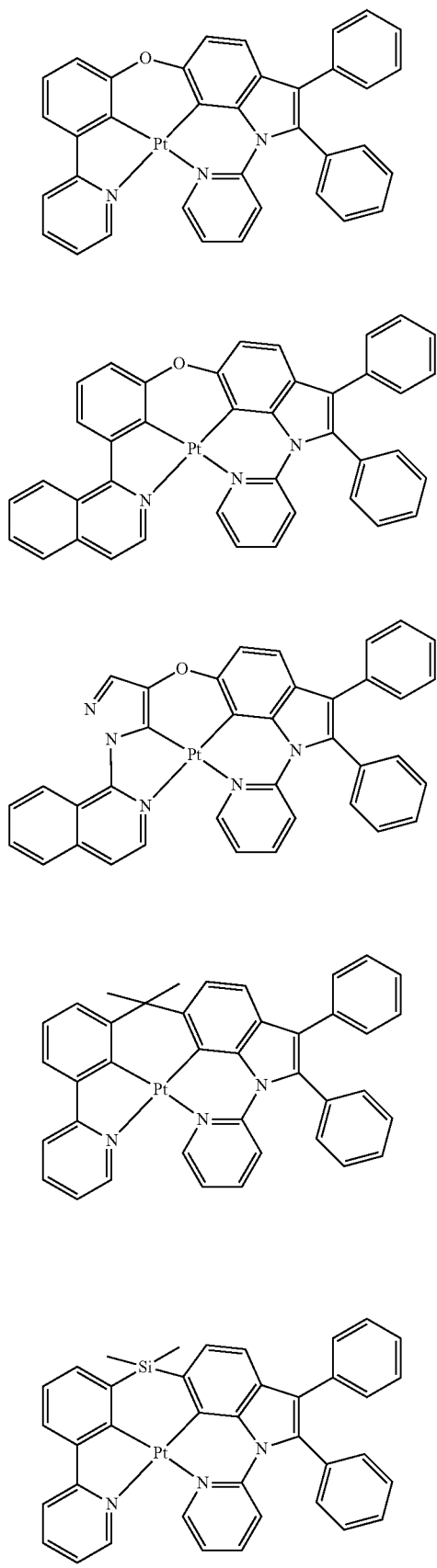
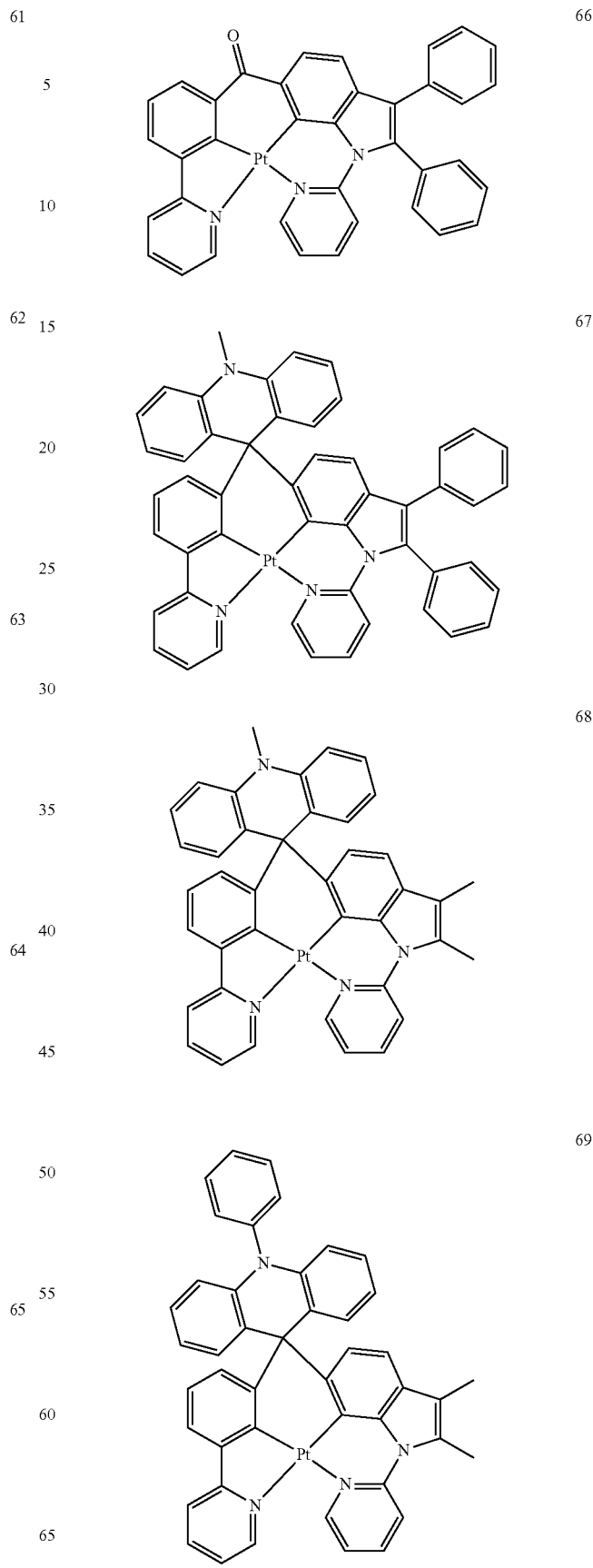

-continued
70 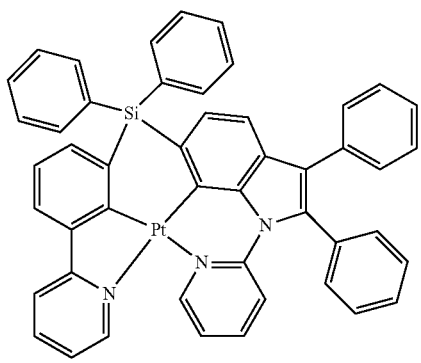
71 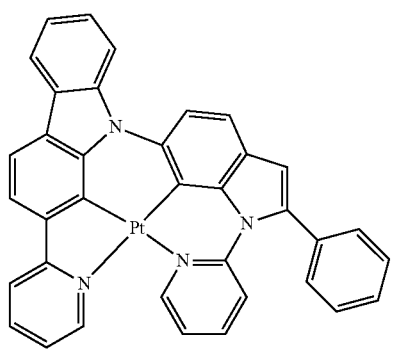
72 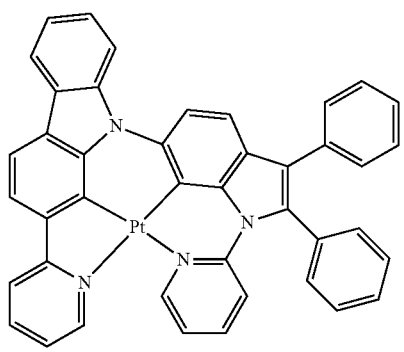
73 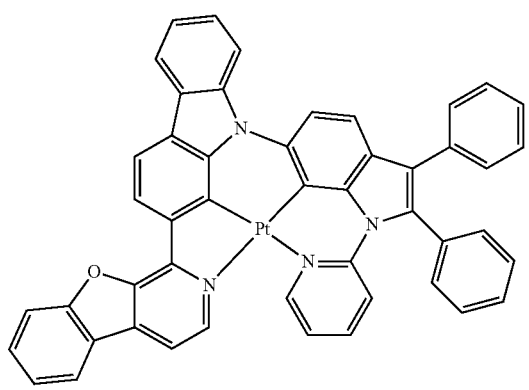
-continued
74 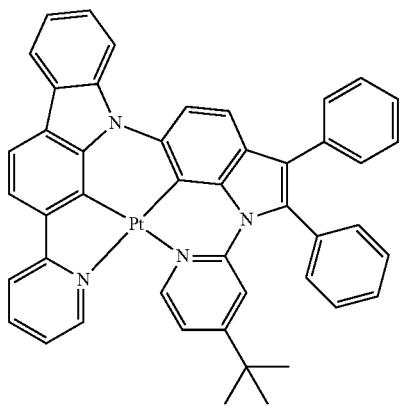
75 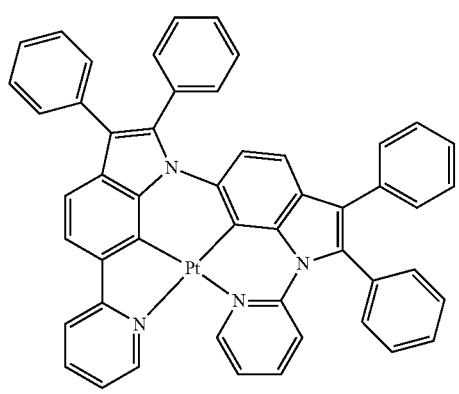
76 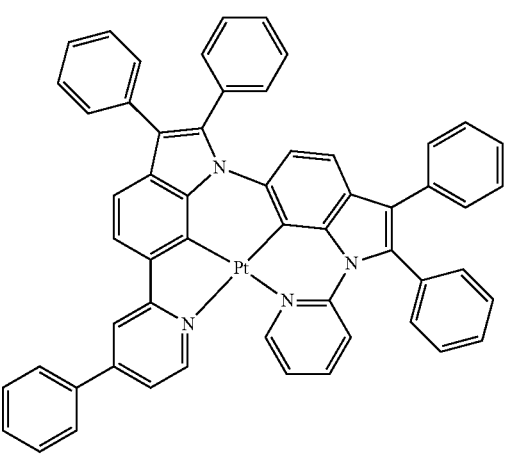
77 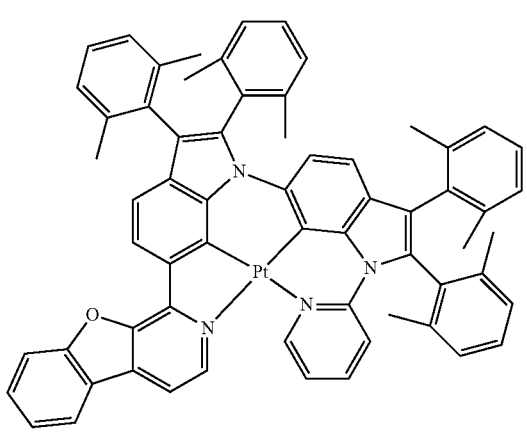

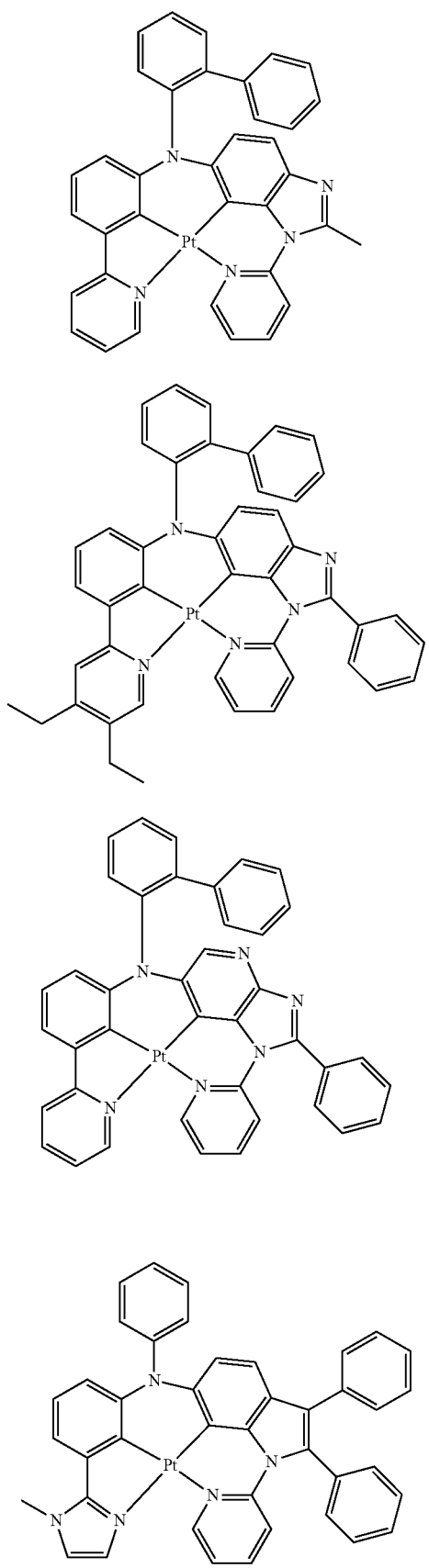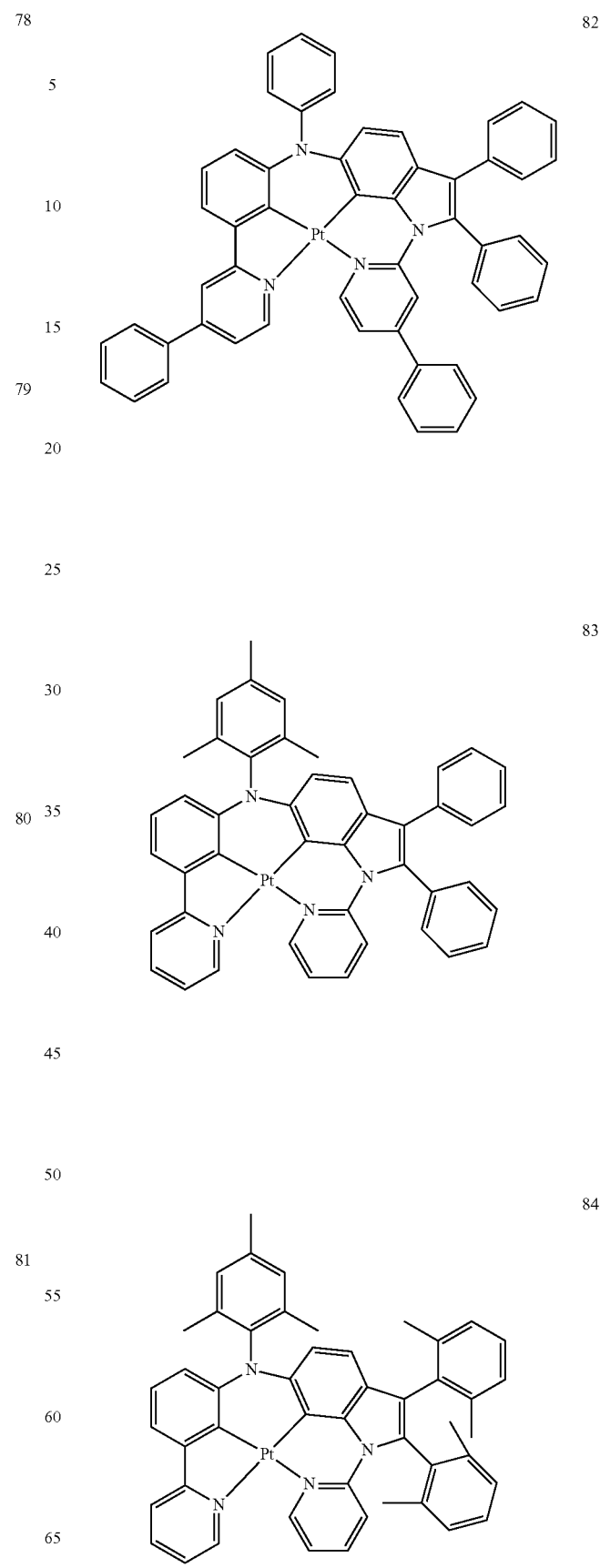

91
-continued
92
-continued
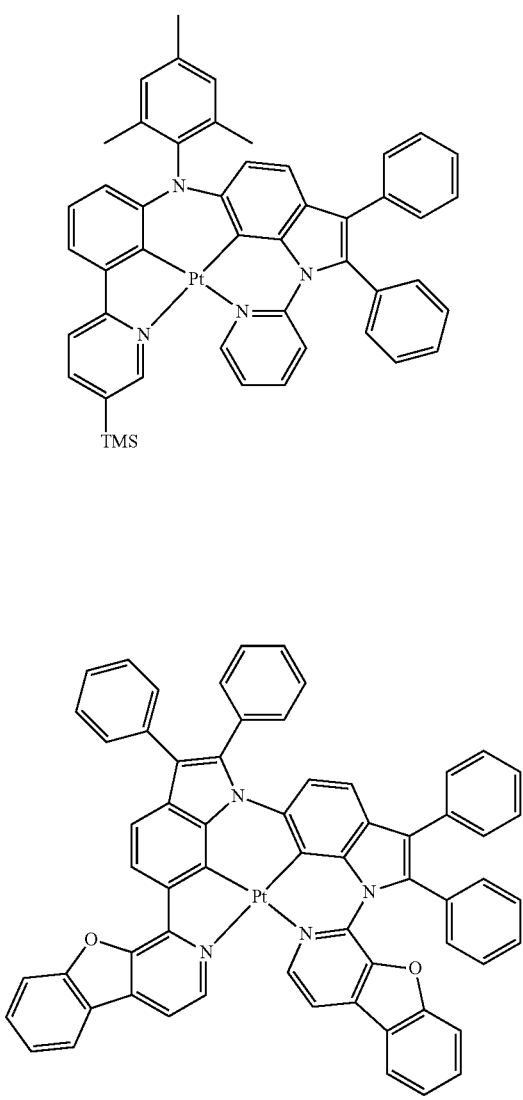
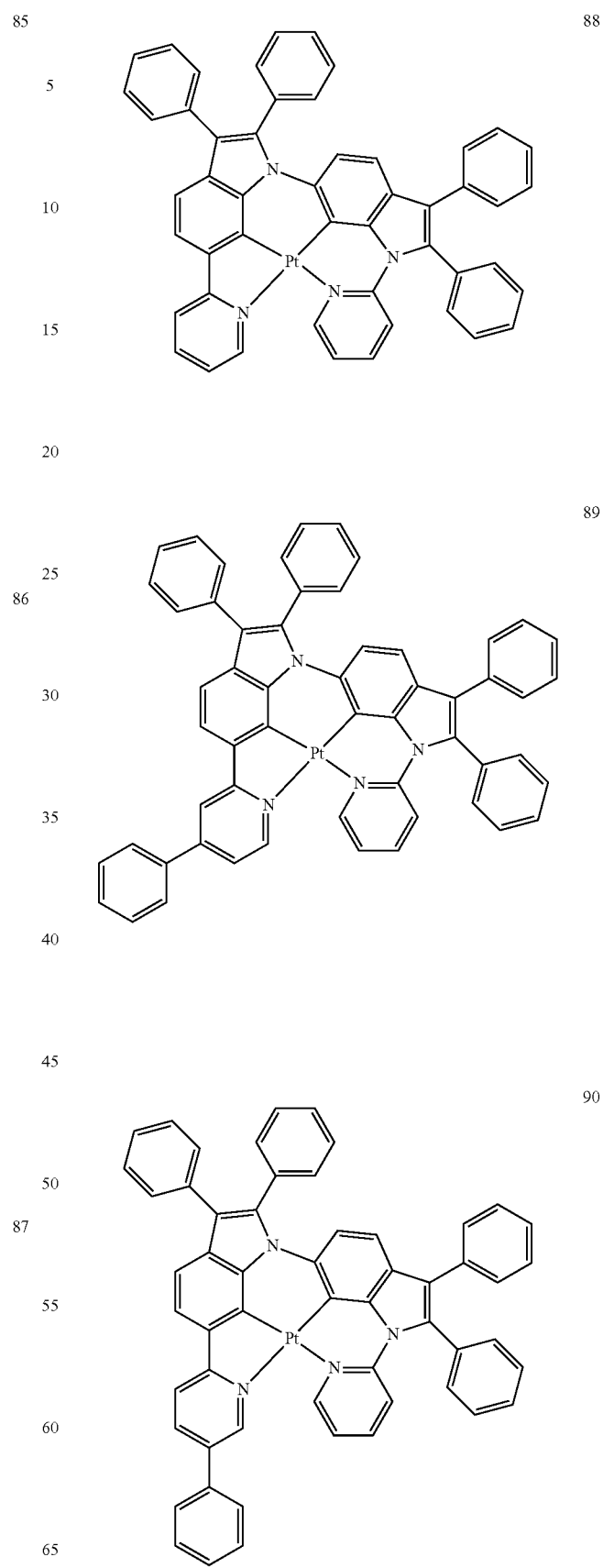

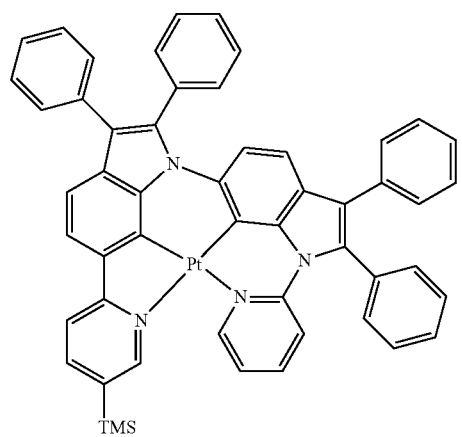
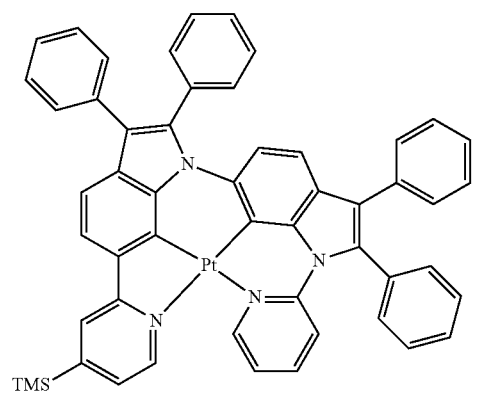
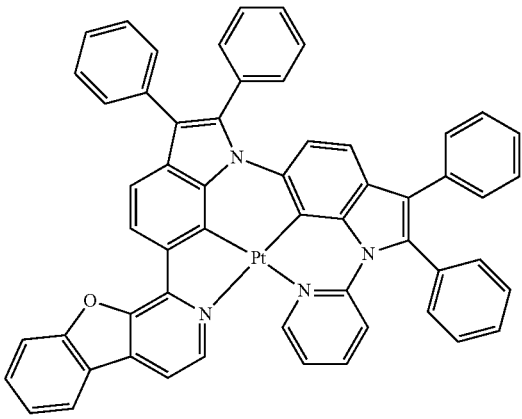
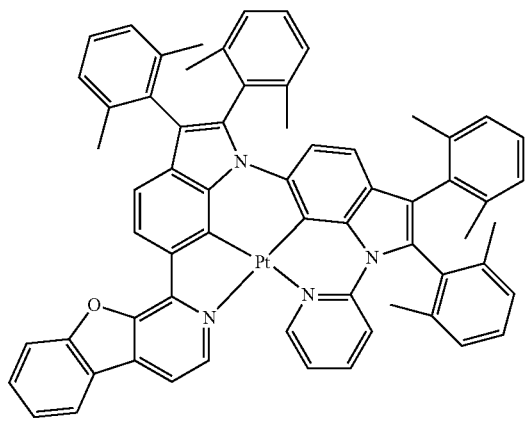
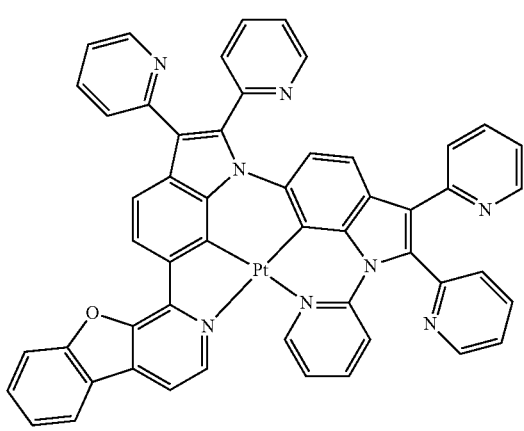
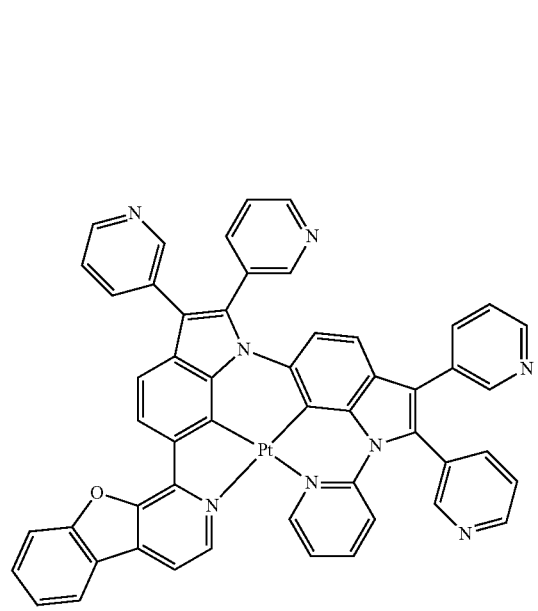
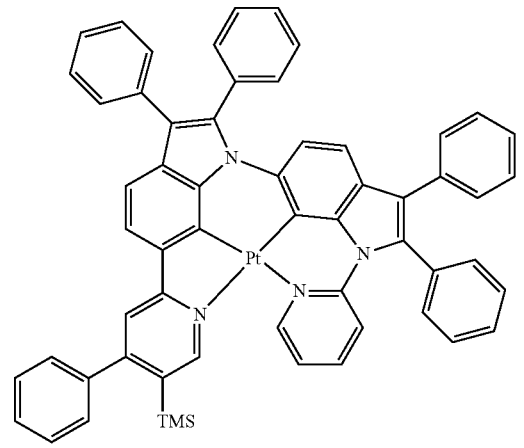

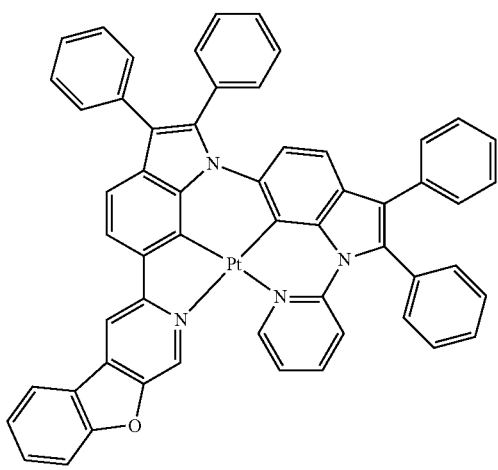
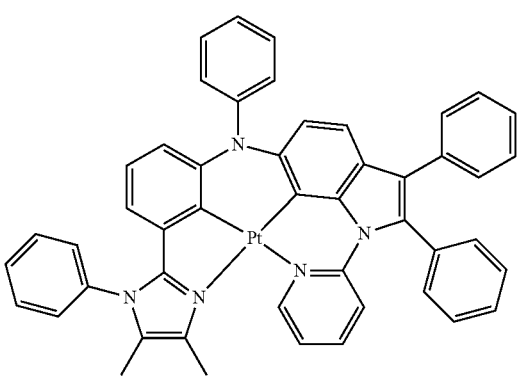
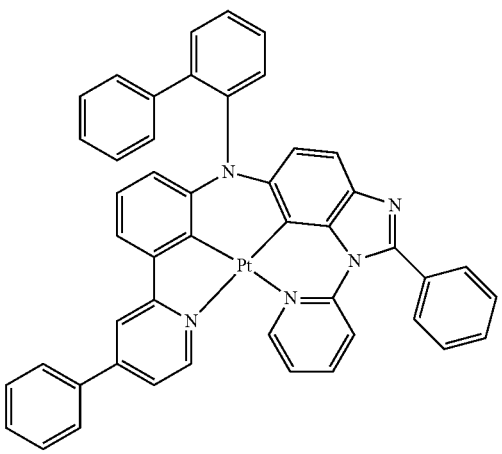
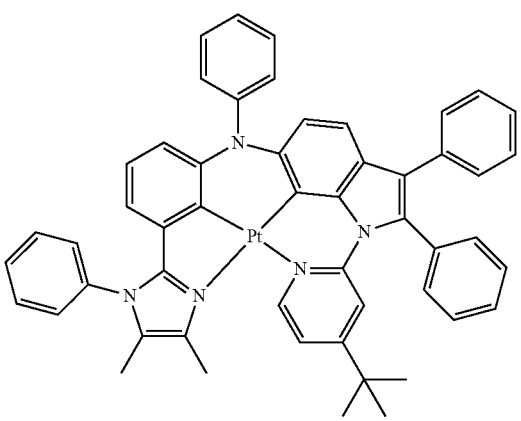
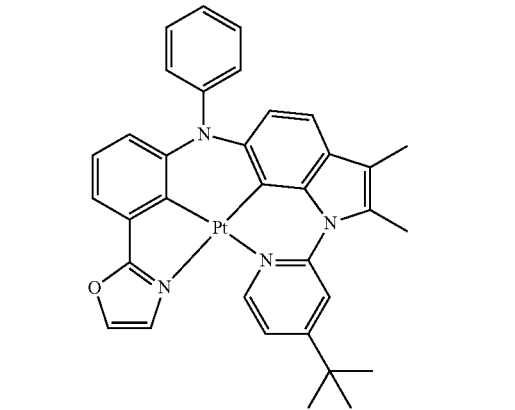
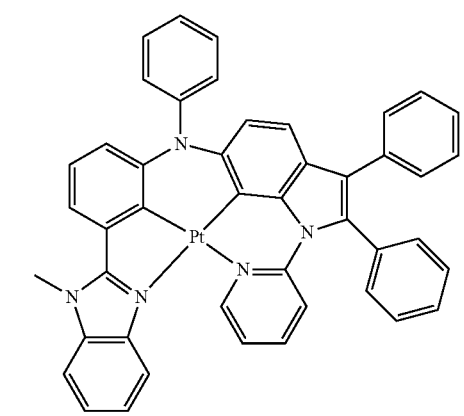
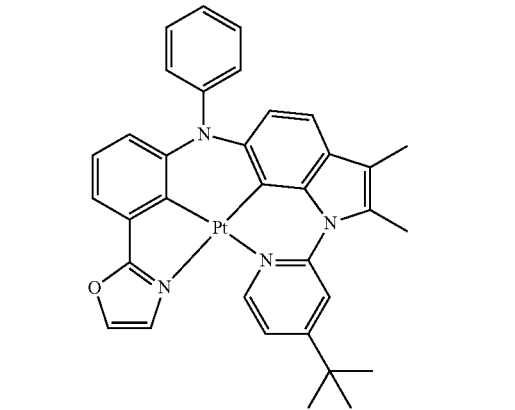

-continued

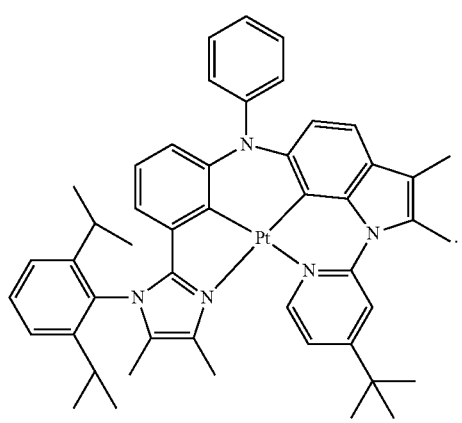

105

A cyclometalated ring formed by $A_1$, $CY_2$, and M in Formula 1 is a 5-membered ring. Accordingly, the molecular stability of the organometallic compound may be improved, and the efficiency (for example, maximum luminescence quantum efficiency or the like) and/or lifespan of an electronic device, for example, an organic light-emitting device, which includes the organometallic compound, may be improved.

Also, in Formula 1, when $X_{31}$ is $C(R_{31})$ and $X_{32}$ is $C(R_{32})$, $R_{31}$ and $R_{32}$ are not linked to each other. Accordingly, aggregation between organometallic compound molecules may be prevented, and the efficiency (for example, maximum luminescence quantum efficiency or the like) and lifespan of an electronic device, for example, an organic light-emitting device, which includes an organometallic compound, may be improved.

For example, a highest occupied molecular orbital (HOMO) energy level, a lowest unoccupied molecular orbital (LUMO) energy level, an energy band gap ($E_g$) energy level, a singlet ($S_1$) energy level, and a triplet ($T_1$) energy level of some Compounds were evaluated by using a density functional theory (DFT) method of a Gaussian program (B3LYP, structurally optimized at a level of 6-31G (d,p)). Evaluation results are shown in Table 1.

TABLE 1

| Compound No. | HOMO (eV) | LUMO (eV) | $E_g$ energy level (eV) | $S_1$ energy level (eV) | $T_1$ energy level (eV) |
|---|---|---|---|---|---|
| 1 | −4.204 | −1.42 | 2.781 | 2.248 | 1.978 |
| 2 | −4.152 | −1.635 | 2.517 | 2.04 | 1.846 |
| 3 | −4.202 | −1.434 | 2.769 | 2.233 | 1.964 |
| 4 | −4.181 | −1.45 | 2.731 | 2.197 | 1.934 |
| 16 | −4.228 | −1.418 | 2.81 | 2.271 | 2 |
| 17 | −4.24 | −1.436 | 2.804 | 2.265 | 1.996 |
| 18 | −4.339 | −1.534 | 2.805 | 2.266 | 1.998 |
| 19 | −4.176 | −1.634 | 2.542 | 2.062 | 1.87 |
| 22 | −4.102 | −1.613 | 2.489 | 2.018 | 1.834 |
| 23 | −4.11 | −1.641 | 2.469 | 2.003 | 1.812 |
| 25 | −4.204 | −1.6 | 2.604 | 2.111 | 1.91 |
| 44 | −4.23 | −1.667 | 2.563 | 2.066 | 1.875 |
| 45 | −4.205 | −1.535 | 2.67 | 2.157 | 1.944 |
| 71 | −4.496 | −1.627 | 2.869 | 2.316 | 2.046 |
| 72 | −4.49 | −1.625 | 2.865 | 2.312 | 2.044 |
| 73 | −4.449 | −1.893 | 2.555 | 2.038 | 1.851 |

TABLE 1-continued

| Compound No. | HOMO (eV) | LUMO (eV) | $E_g$ energy level (eV) | $S_1$ energy level (eV) | $T_1$ energy level (eV) |
|---|---|---|---|---|---|
| 74 | −4.443 | −1.561 | 2.882 | 2.32 | 2.054 |
| A | −4.633 | −1.623 | 3.010 | 2.449 | 2.179 |
| B | −4.390 | −1.594 | 2.796 | 2.312 | 2.277 |

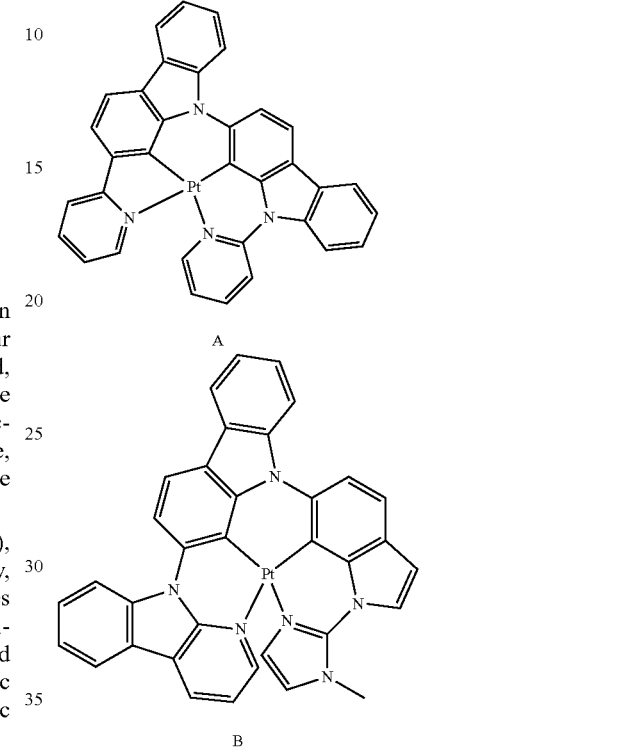

From Table 1, it is confirmed that the organometallic compound represented by Formula 1 has such electrical characteristics that are suitable for use in an electronic device, for example, for use as a dopant for an organic light-emitting device.

Synthesis methods of the organometallic compound represented by Formula 1 may be recognizable by those of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;

a second electrode; and an organic layer that is disposed between the first electrode and the second electrode, wherein the organic layer includes an emission layer and at least one of the organometallic compound represented by Formula 1.

The organic light-emitting device may have, due to the inclusion of an organic layer including the organometallic compound represented by Formula 1, a low driving voltage, high efficiency, high power, high quantum efficiency, a long lifespan, a low roll-off ratio, and excellent color purity.

The organometallic compound of Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression "(an organic layer) includes at least one of organometallic compounds" used herein may include an embodiment in which "(an organic layer) includes identical organometallic compounds represented by Formula 1" and an embodiment in which "(an organic layer) includes two or more different organometallic compounds represented by Formula 1."

For example, the organic layer may include, as the organometallic compound, only Compound 1. In this regard, Compound 1 may be included in an emission layer of the organic light-emitting device. In one or more embodiments, the organic layer may include, as the organometallic compound, Compound 1 and Compound 2. In this embodiment, Compound 1 and Compound 2 may be included in an identical layer (for example, Compound 1 and Compound 2 all may be included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

In an embodiment, in the organic light-emitting device, the first electrode is an anode, and the second electrode is a cathode, and the organic layer further includes a hole transport region disposed between the first electrode and the emission layer and an electron transport region disposed between the emission layer and the second electrode, wherein the hole transport region includes a hole injection layer, a hole transport layer, an electron blocking layer, or any combination thereof, and wherein the electron transport region includes a hole blocking layer, an electron transport layer, an electron injection layer, or any combination thereof.

The term "organic layer" as used herein refers to a single layer and/or a plurality of layers between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a compound that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

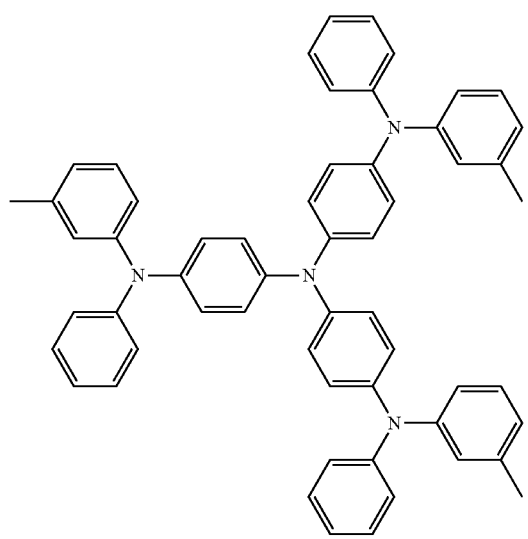

m-MTDATA

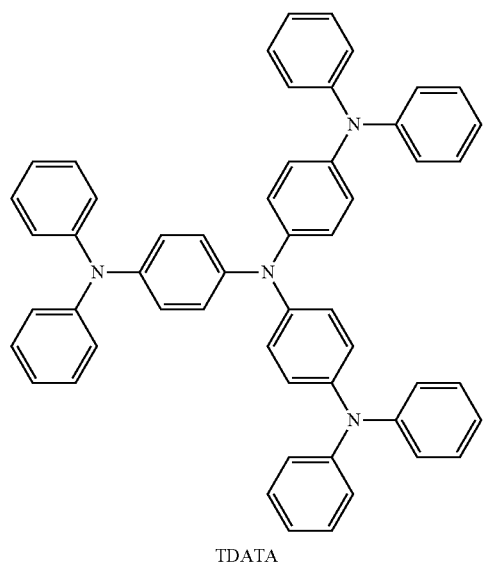

TDATA

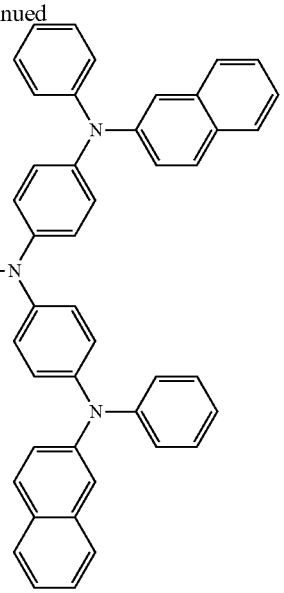

2-TNATA

NPB

β-NPB

TPD

-continued

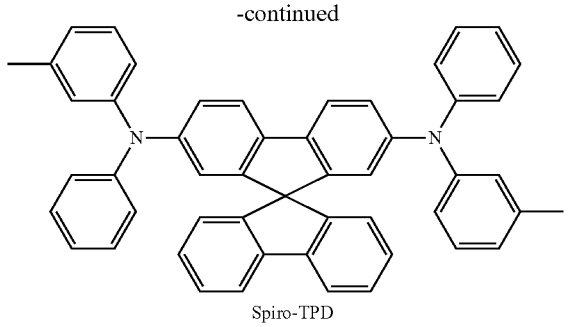

Spiro-TPD

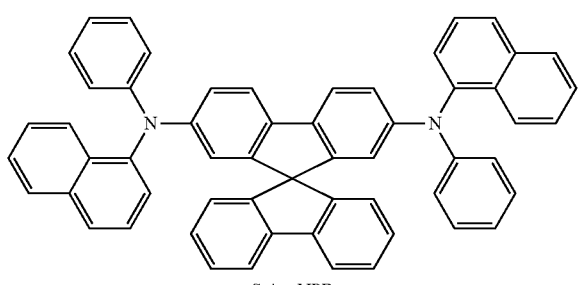

Spiro-NPB

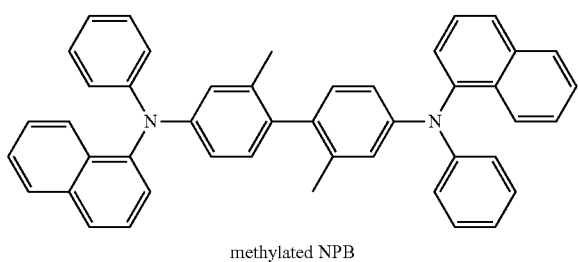

methylated NPB

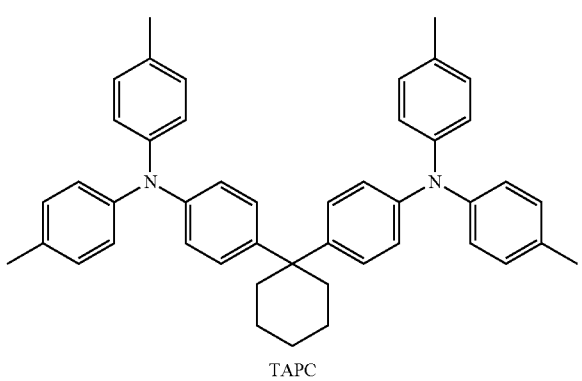

TAPC

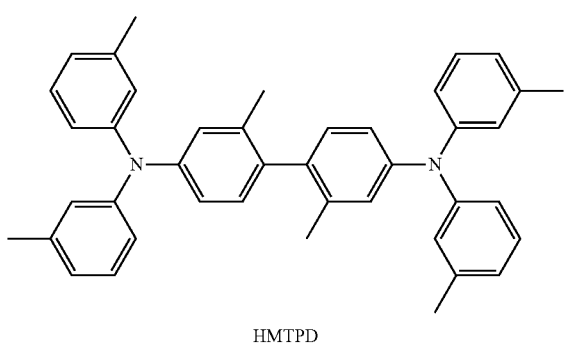

HMTPD

-continued

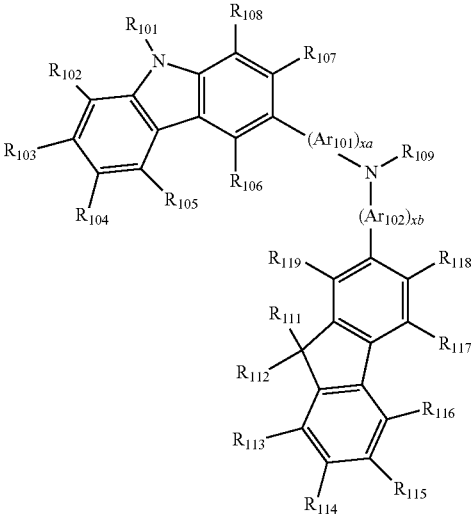

Formula 201

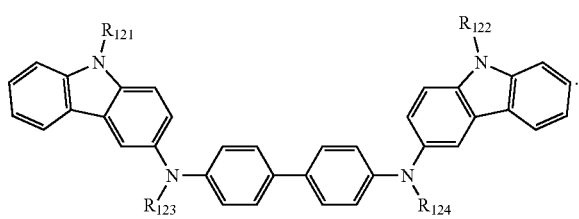

Formula 202

$Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

xa and xb in Formula 201 may each independently be an integer from 0 to 5, or may each independently be 0, 1, or 2. For example, xa may be 1, and xb may be 0, but embodiments of the present disclosure are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkoxy group, a phenyl group, a naphthyl group, an anthracenyl group, and a pyridinyl group.

According to an embodiment, the compound represented by Formula 201 may be represented by Formula 201A, but embodiments of the present disclosure are not limited thereto:

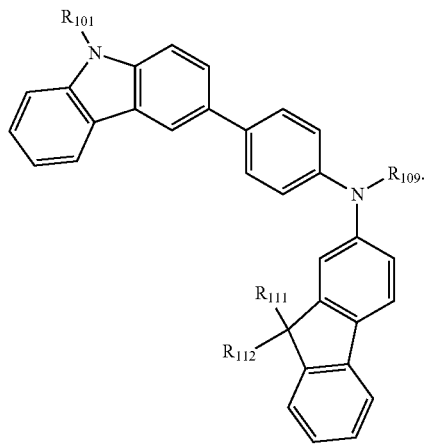

Formula 201A $R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

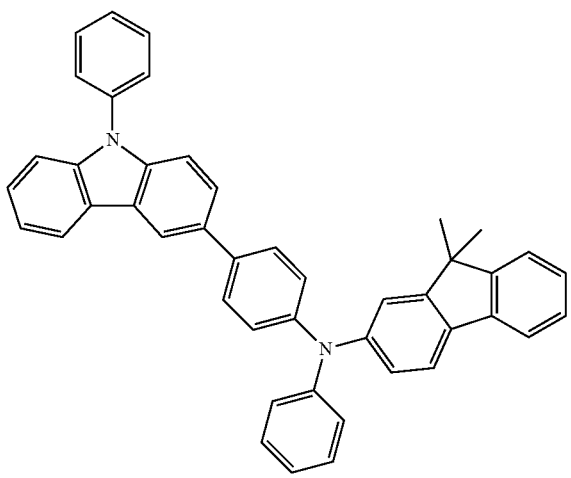

HT1

107
-continued
HT2
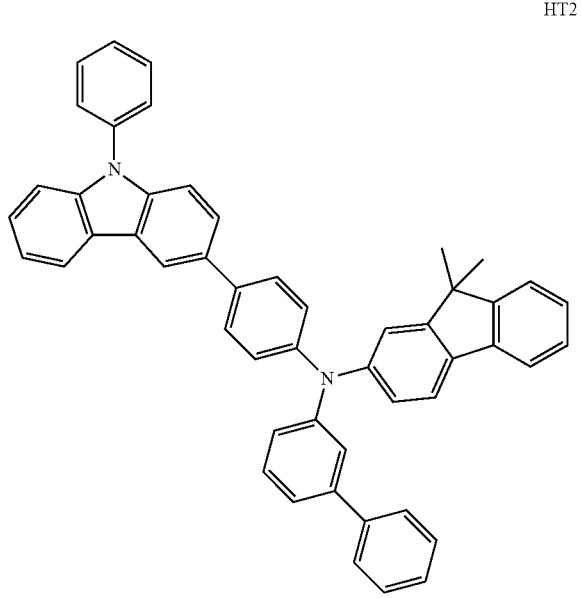
HT3
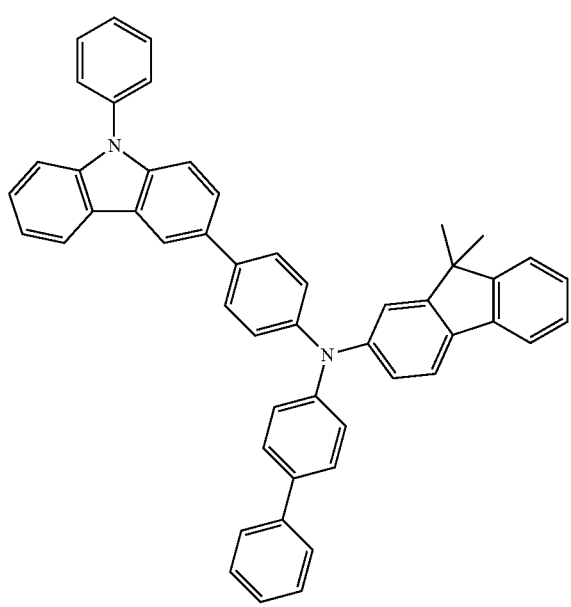
108
-continued
HT4
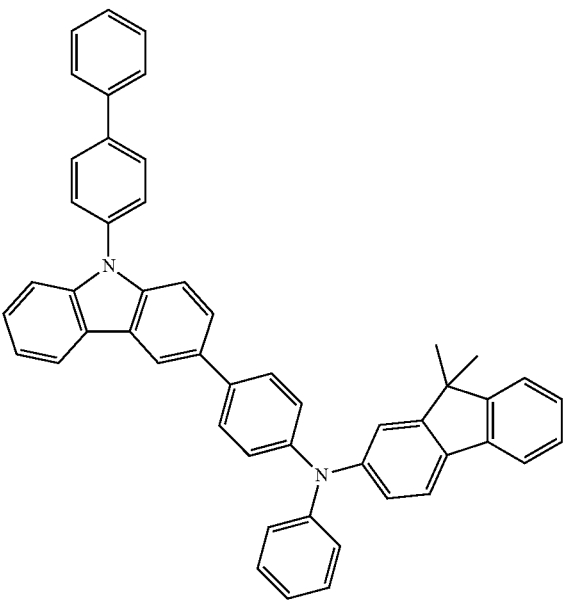
HT5

HT6
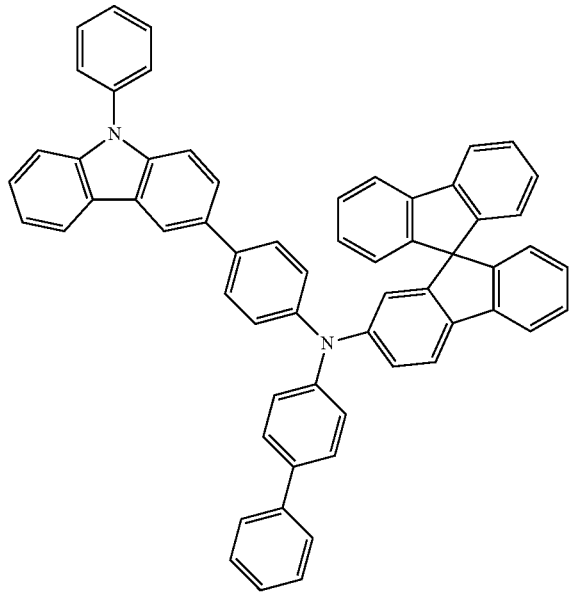
HT7
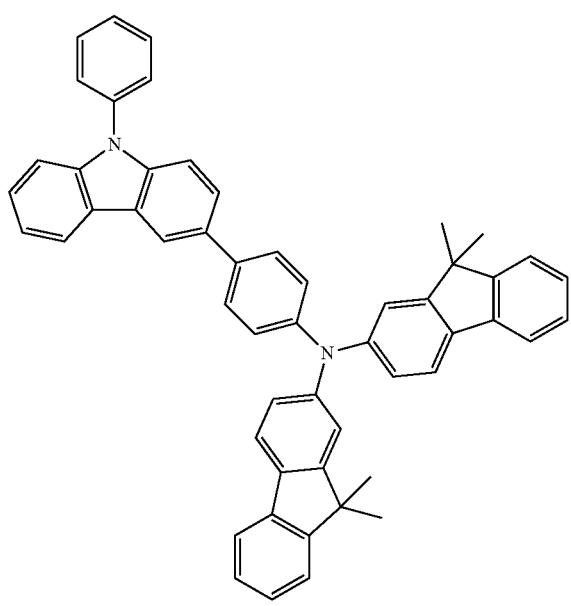
HT8
HT9
HT10
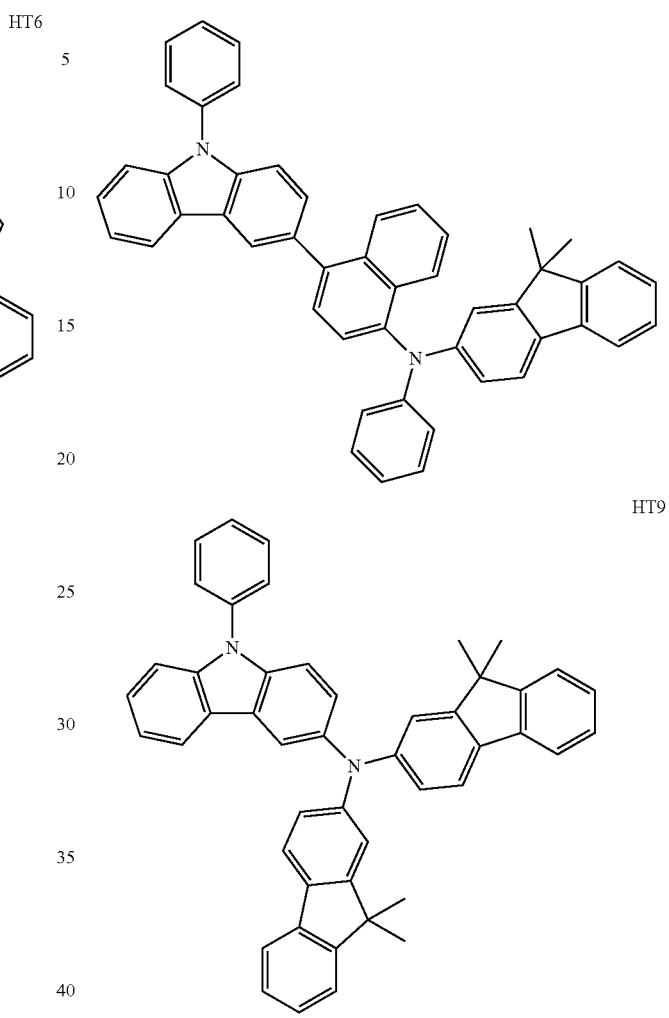

HT11
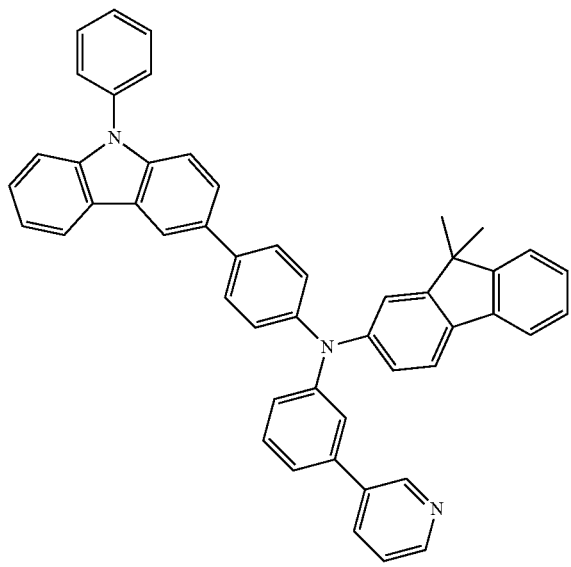
HT12
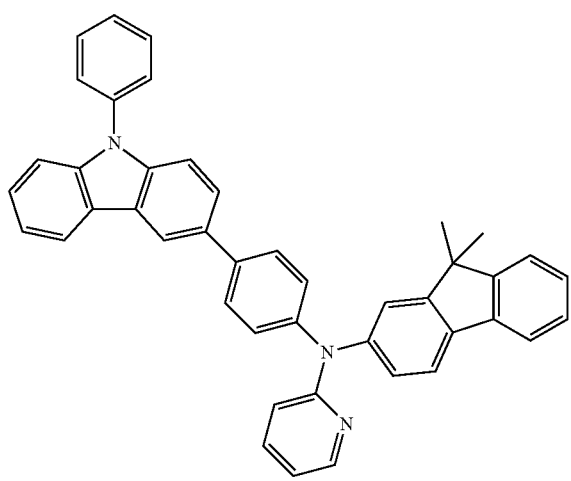
HT13
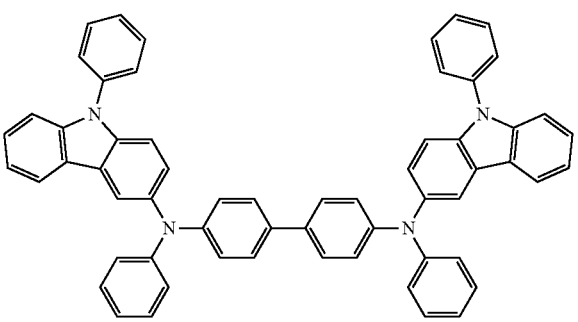
HT14
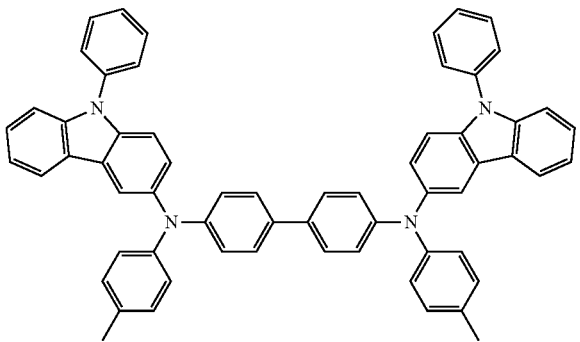
HT15
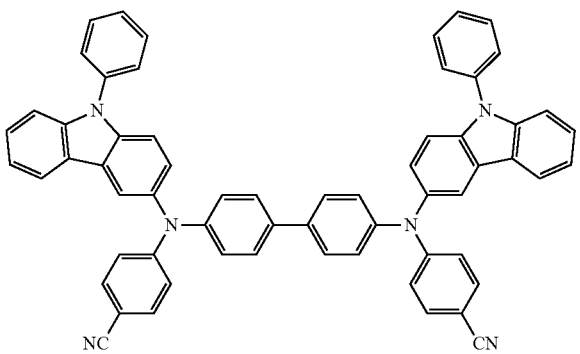
HT16
HT17
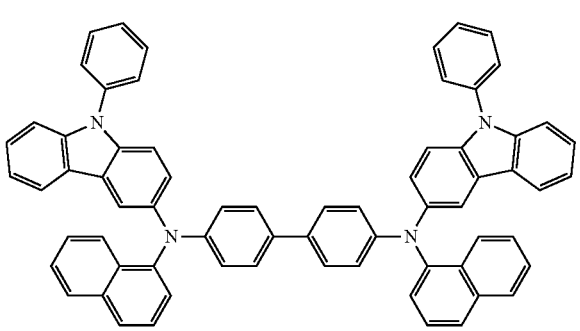

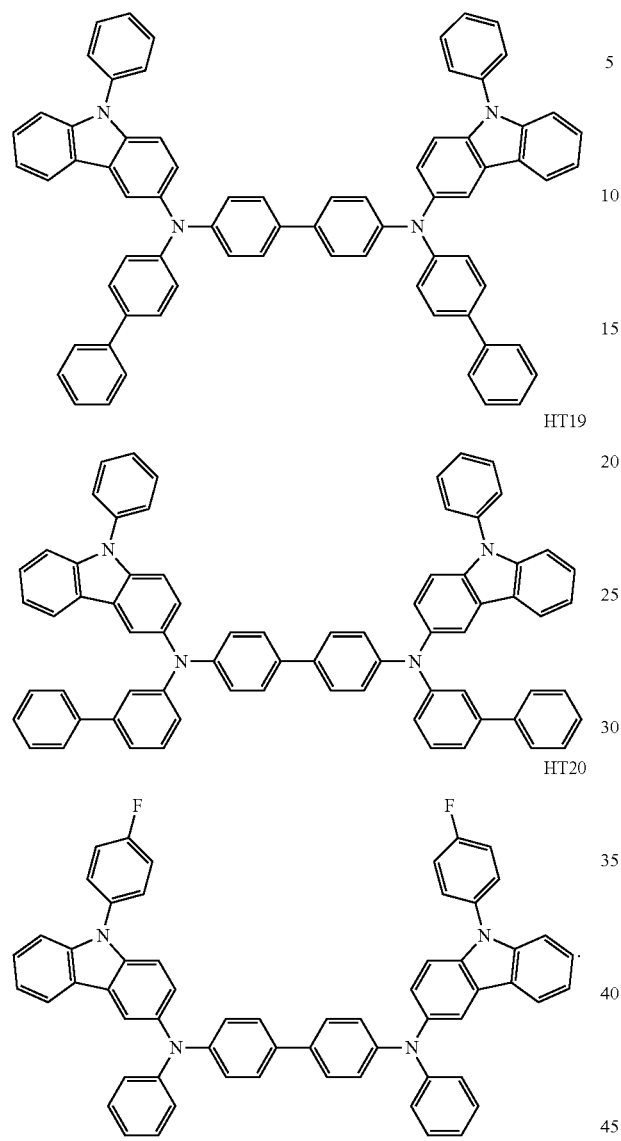

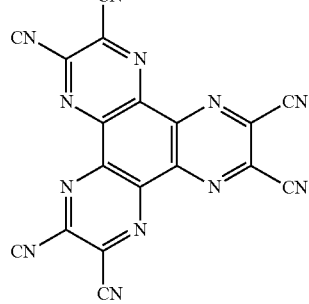

HT-D1

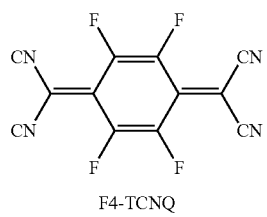

F4-TCNQ

A thickness of the hole transport region may be in a range of about 100 Å to about 10,000 Å, for example, about 100 Å to about 1,000 Å. When the hole transport region includes at least one of a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, mCP, Compound H50, and Compound H51:

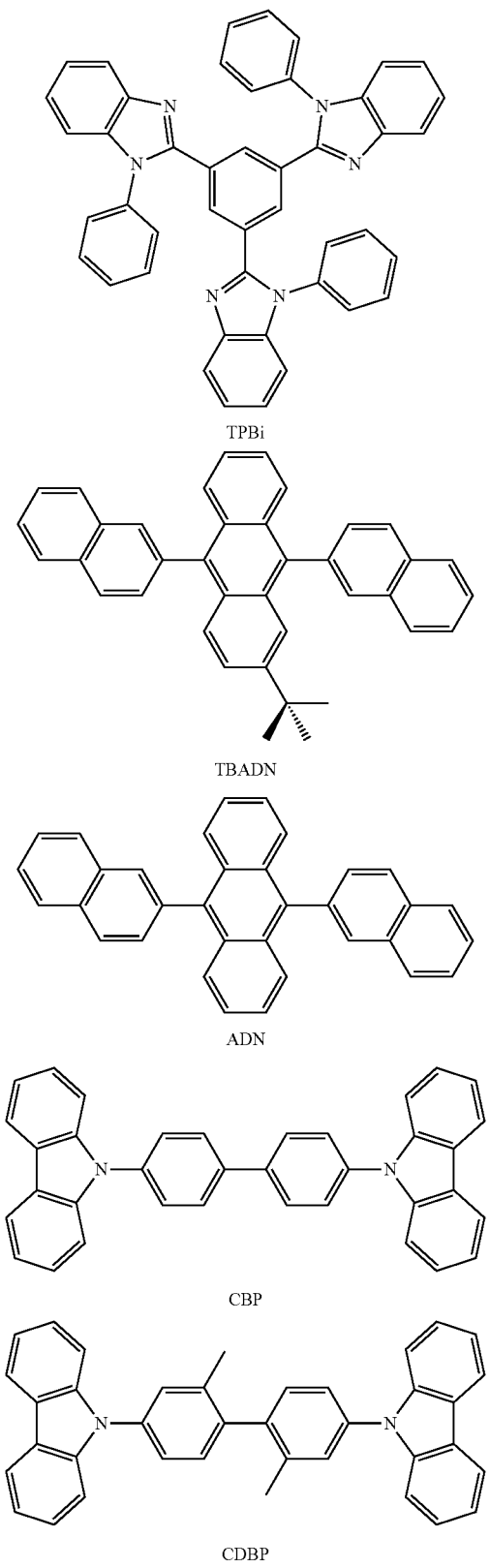

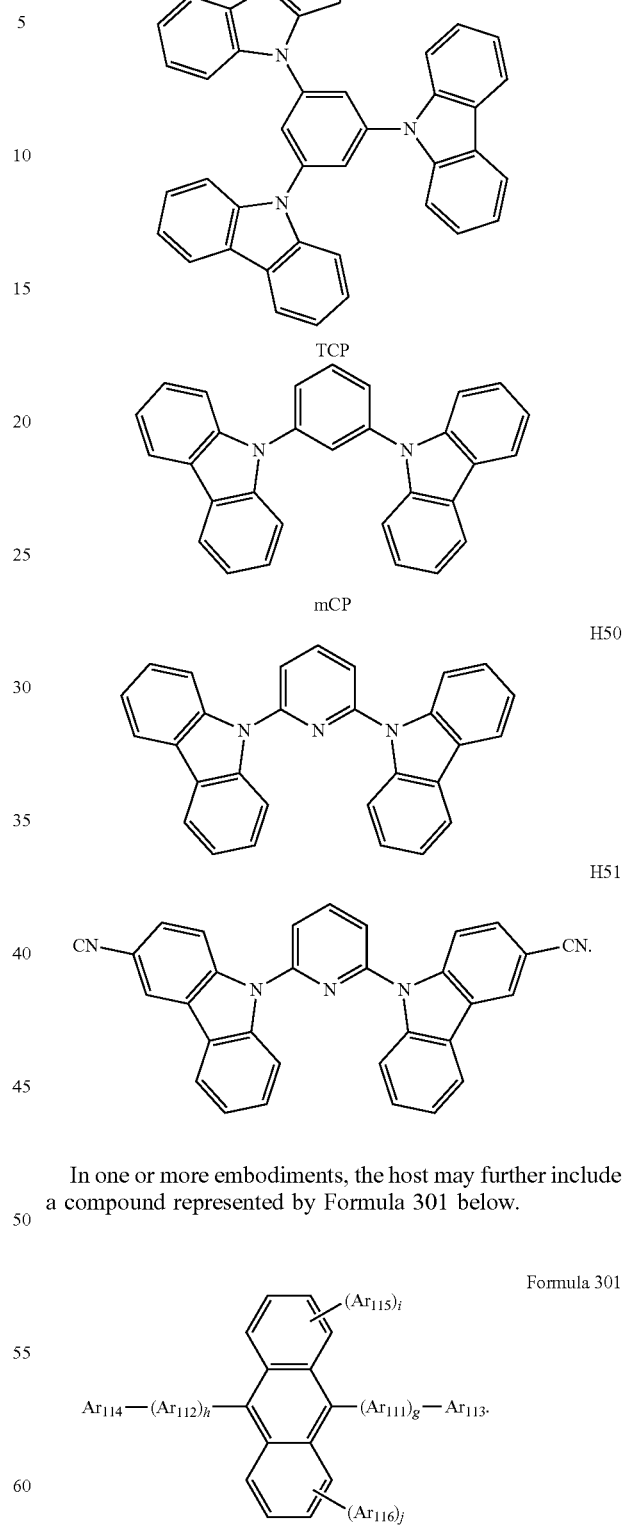

In one or more embodiments, the host may further include a compound represented by Formula 301 below.

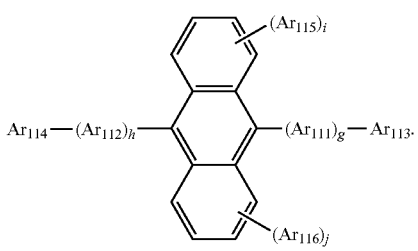

Formula 301

$Ar_{111}$ and $Ar_{112}$ in Formula 301 may each independently be selected from:

a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may each independently be selected from:

a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one selected from a phenyl group, a naphthyl group, and an anthracenyl group.

g, h, i, and j in Formula 301 may each independently be an integer from 0 to 4, for example, 0, 1, or 2.

$Ar_{113}$ to $Ar_{116}$ in Formula 301 may each independently be selected from:

a $C_1$-$C_{10}$ alkyl group substituted with at least one selected from a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

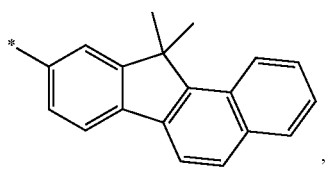 [SMILES: *c1ccc2c(c1)C(C)(C)c1c-2ccc2ccccc12]

but embodiments of the present disclosure are not limited thereto.

In one or more embodiments, the host may include a compound represented by Formula 302 below:

Formula 302

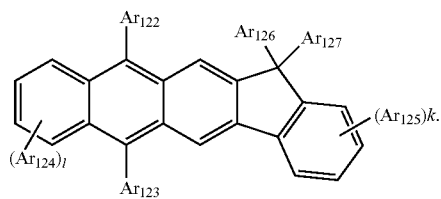

$Ar_{122}$ to $Ar_{125}$ in Formula 302 are the same as described in connection with $Ar_{113}$ in Formula 301.

$Ar_{126}$ and $Ar_{127}$ in Formula 302 may each independently be a $C_1$-$C_{10}$ alkyl group (for example, a methyl group, an ethyl group, or a propyl group).

k and l in Formula 302 may each independently be an integer from 0 to 4. For example, k and l may be 0, 1, or 2.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

When the emission layer includes a host and a dopant, an amount of the dopant may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq but embodiments of the present disclosure are not limited thereto.

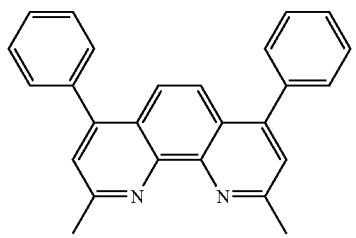

BCP

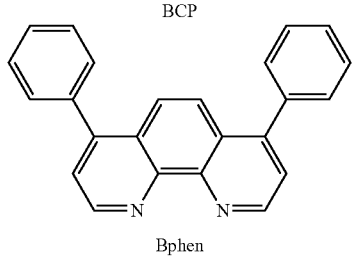

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq₃, BAlq, TAZ, and NTAZ:

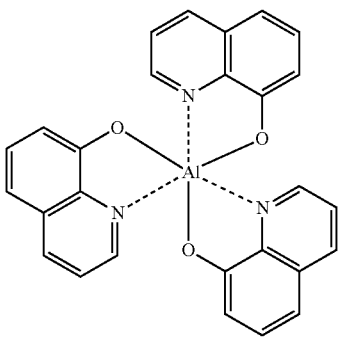
Alq3

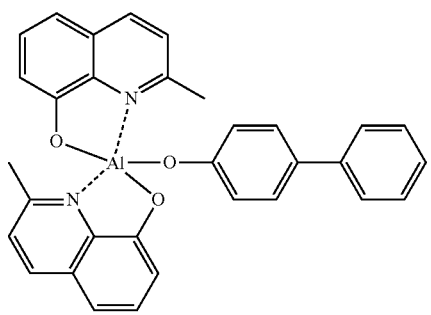
BAlq

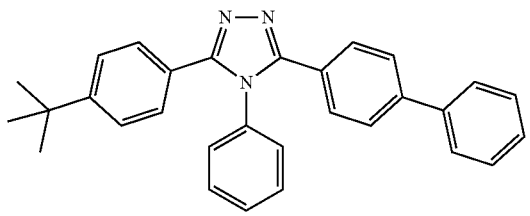
TAZ

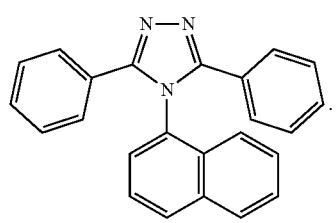
NTAZ

In one or more embodiments, the electron transport layer may include at least one of ET1 to ET25, but are not limited thereto:

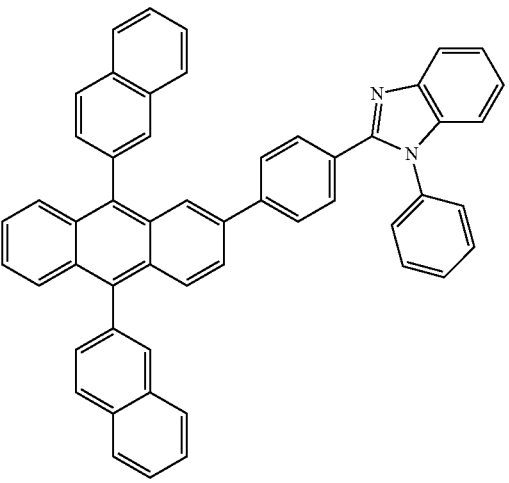
ET1

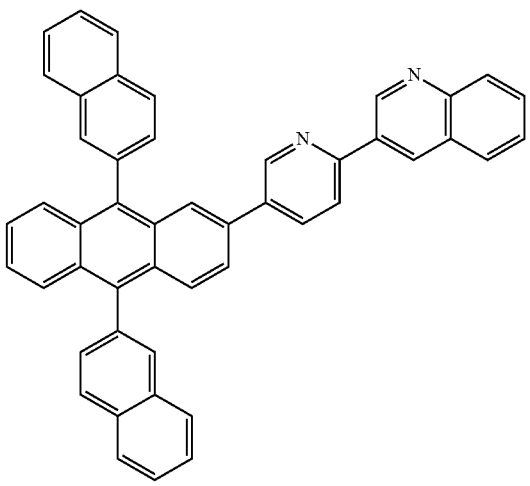
ET2

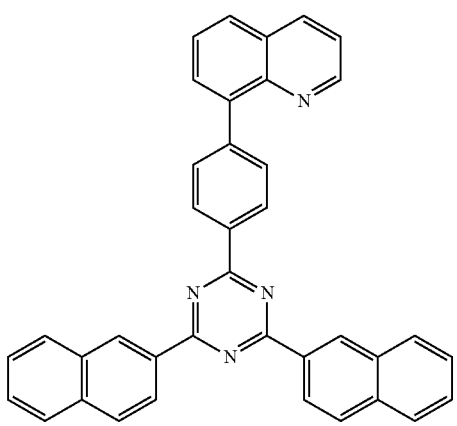
ET3

-continued
ET4
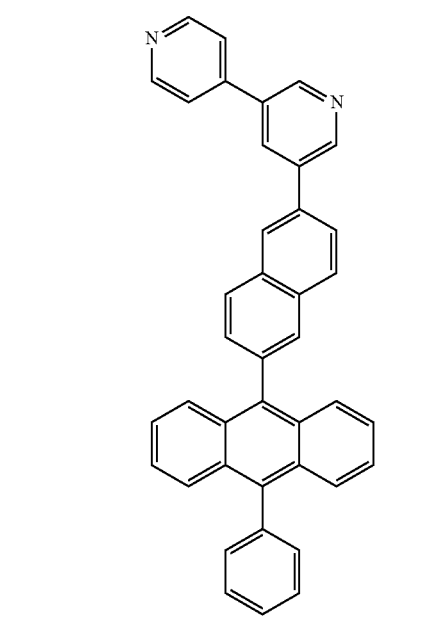
ET5
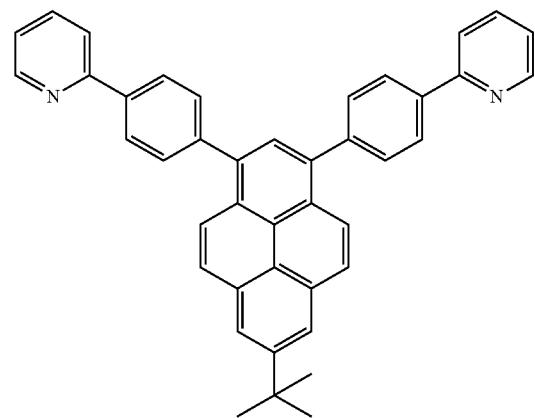
ET6
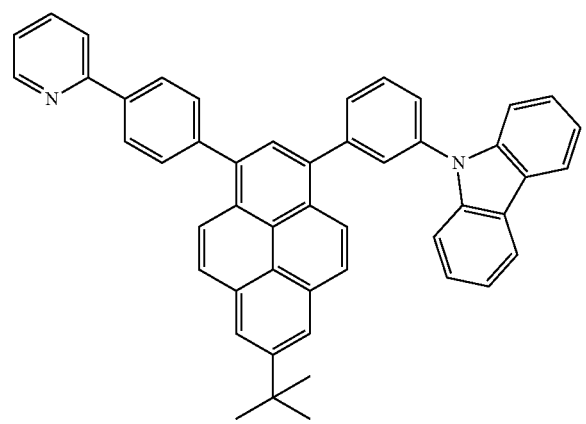
-continued
ET7
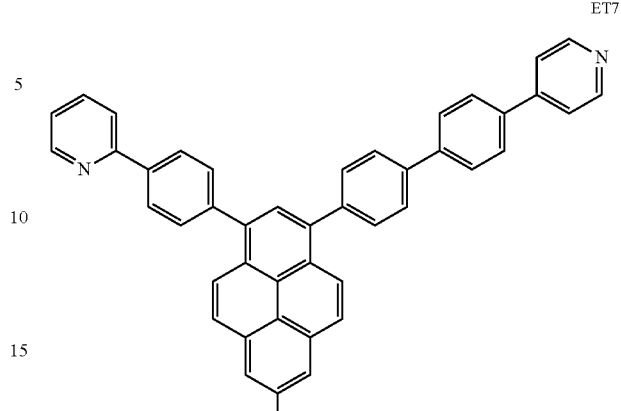
ET8
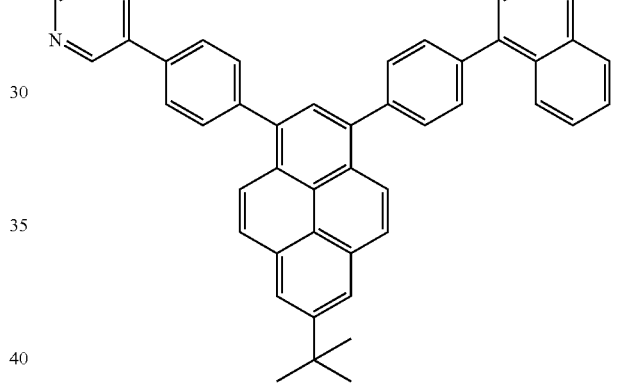
ET9
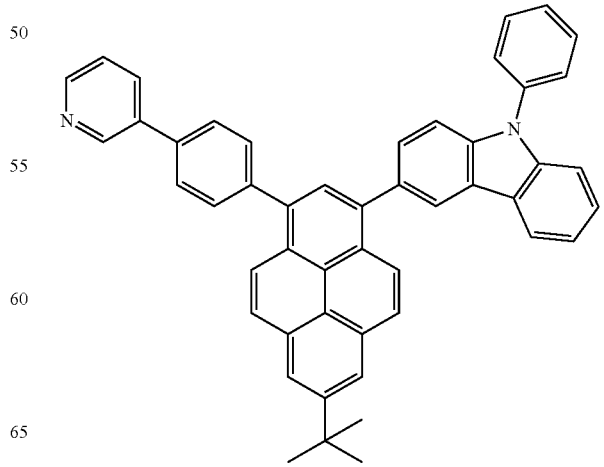

ET10
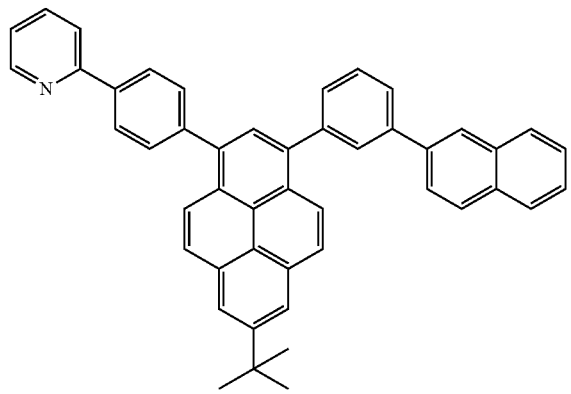
ET11
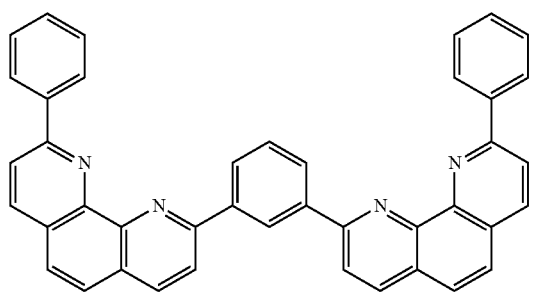
ET12
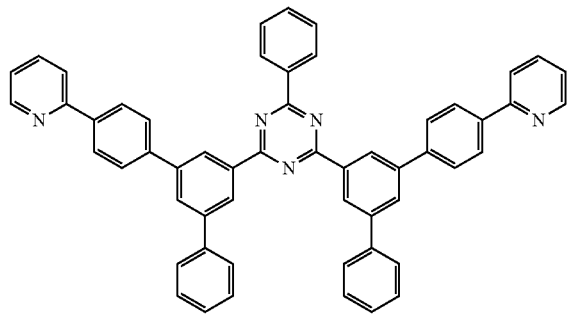
ET13
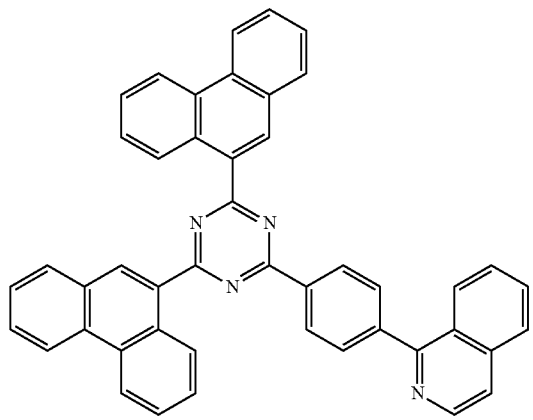
ET14
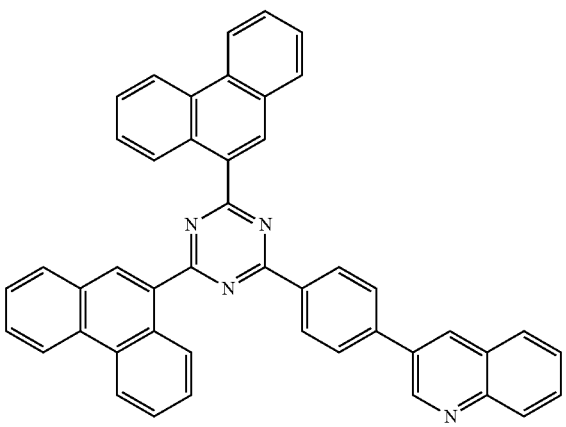
ET15
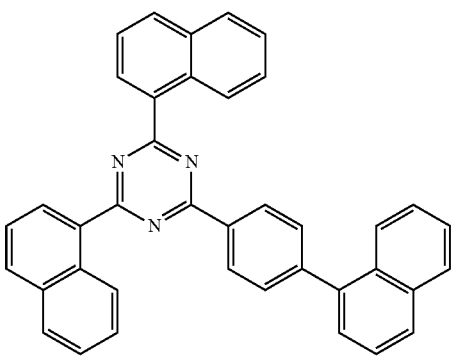
ET16
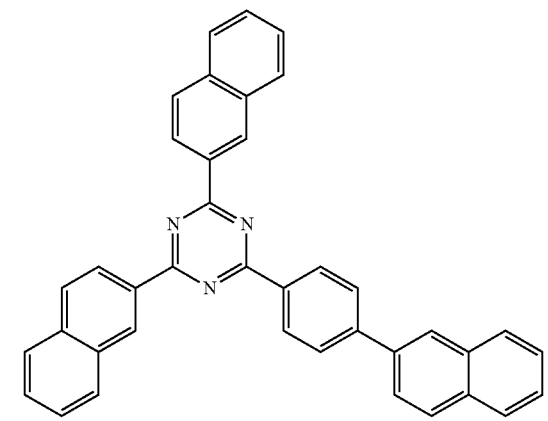

ET17
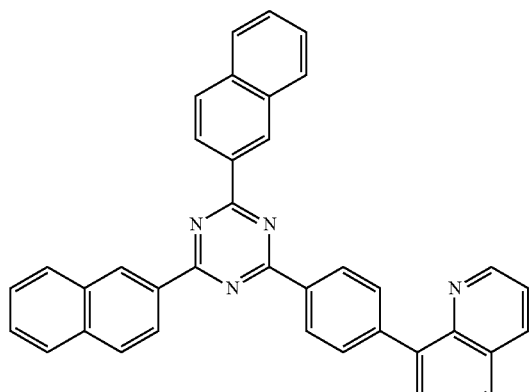
ET20
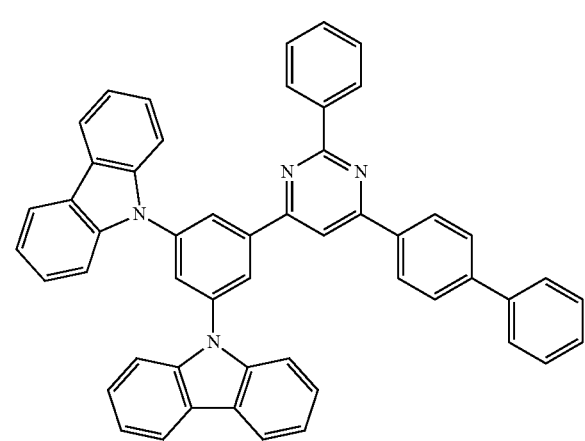
ET18
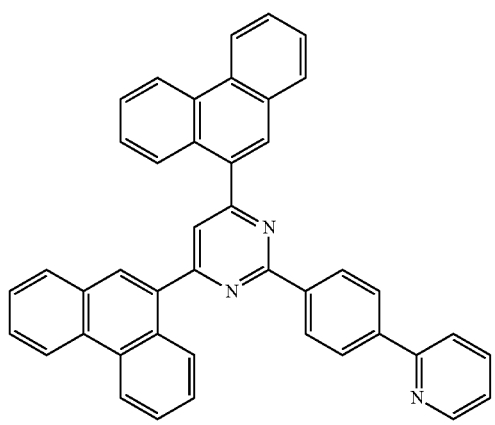
ET21
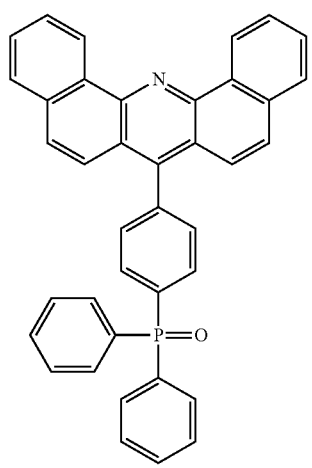
ET19
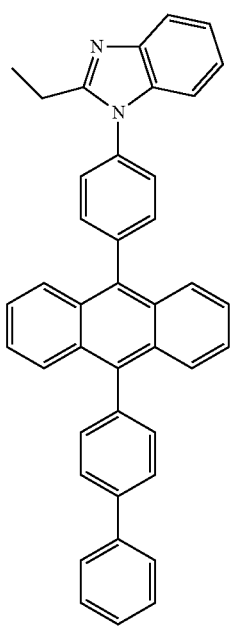
ET22
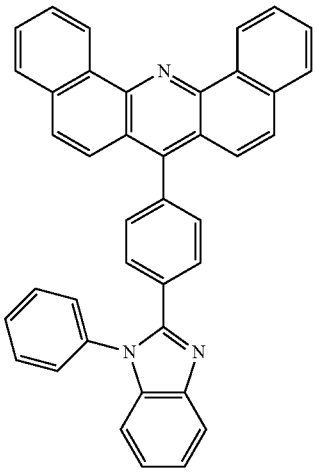

ET23

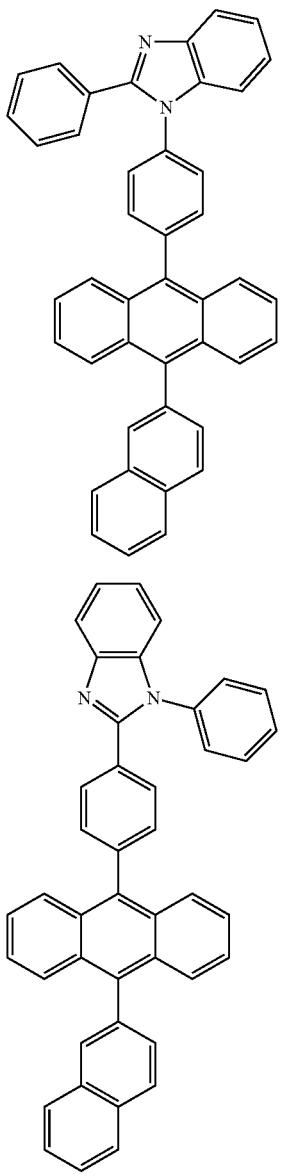

ET24

ET25

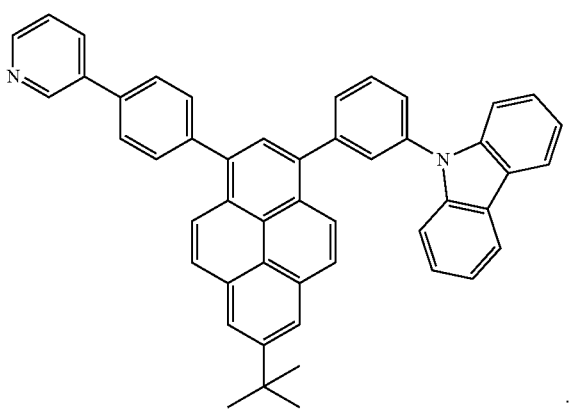

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium 8-hydroxyquinolate, LiQ) or ET-D2:

ET-D1

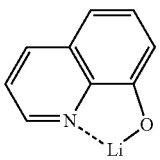

ET-D2

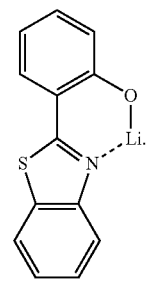

The electron transport region may include an electron injection layer that promotes flow of electrons from the second electrode 19 thereinto.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to FIG. 1, but embodiments of the present disclosure are not limited thereto.

Another aspect of the present disclosure provides a diagnostic composition including at least one organometallic compound represented by Formula 1.

The organometallic compound represented by Formula 1 provides high luminescent efficiency. Accordingly, a diagnostic composition including the organometallic compound may have high diagnostic efficiency.

The diagnostic composition may be used in various applications including a diagnosis kit, a diagnosis reagent, a biosensor, and a biomarker.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having an aromatic system that has at least one heteroatom selected from N, O, P, Si, and S as a ring-forming atom, and 1 to 60 carbon atoms. The term "$C_1$-$C_{60}$ heteroarylene group" as used herein refers to a divalent group having an aromatic system that has at least one heteroatom selected from N, O, P, Si and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein A103 is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_6$-$C_{30}$ carbocyclic group" as used herein refers to a saturated or unsaturated cyclic group having, as a ring-forming atom, 5 to 30 carbon atoms only. The $C_6$-$C_{30}$ carbocyclic group may be a monocyclic group or a polycyclic group.

The term "$C_1$-$C_{30}$ heterocyclic group" as used herein refers to a saturated or unsaturated cyclic group having, as a ring-forming atom, at least one heteroatom selected from N, O, Si, P, and S other than 1 to 30 carbon atoms. The $C_1$-$C_{30}$ heterocyclic group may be a monocyclic group or a polycyclic group.

At least one substituent of the substituted $C_6$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{16})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{36})$, —$B(Q_{36})(Q_{37})$, and —$P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Hereinafter, a compound and an organic light-emitting device according to embodiments are described in detail with reference to Synthesis Examples and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1: Synthesis of Compound 1

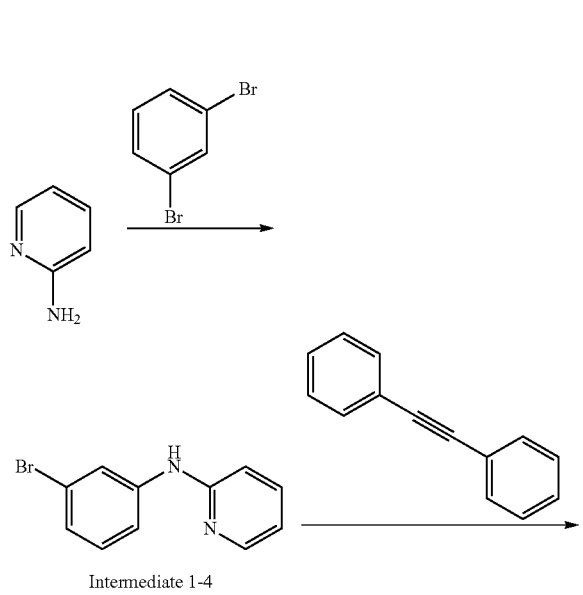

Intermediate 1-4

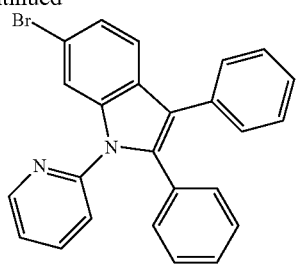

Intermediate 1-3

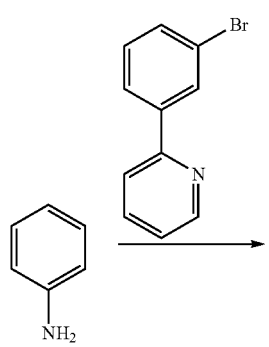

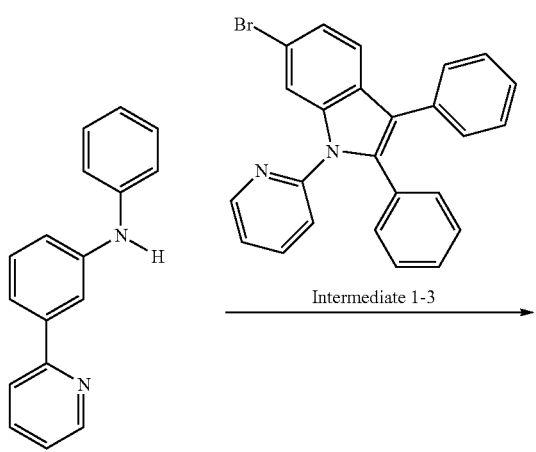

Intermediate 1-2

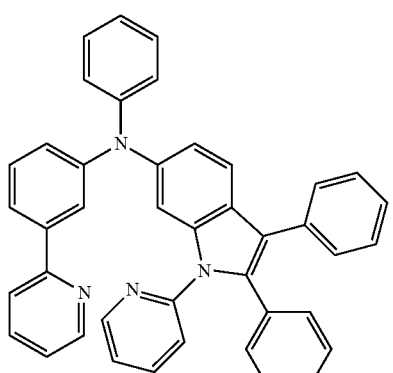

Intermediate 1-1

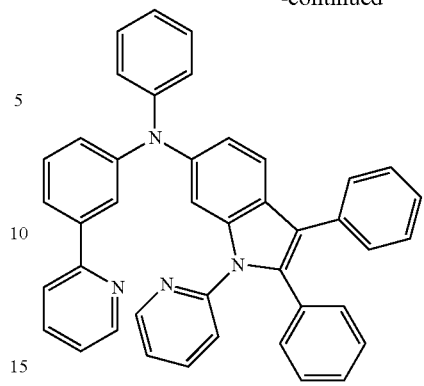

Intermediate 1-1

$\xrightarrow{\text{PtCl}_2}{\text{PhCN}}$

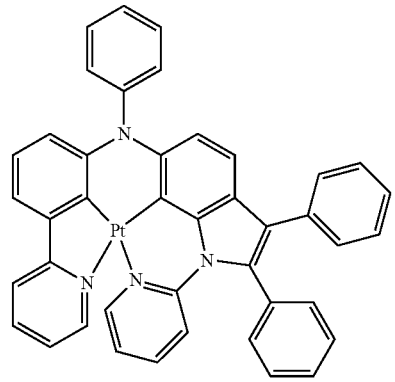

Compound 1

Synthesis of Intermediate 1-4

35.4 grams (g) (150 millimoles, mmol) of 1,3-dibromobenzene, 14.1 g (150 mmol) of 2-aminopyridine, 4.25 g (7.5 mmol) of bis(dibenzylideneacetone)palladium(0) (Pd(dba)$_2$), 6.0 g (15 mmol) of tri-tert-butylphosphine (P(t-Bu)$_3$), and 21.6 g (225 mmol) of sodium tert-butoxide (NaOtBu) were added to a flask, 500 milliliters (mL) of toluene was added thereto, and the flask was purged with nitrogen. The resultant mixture was refluxed for 24 hours, cooled to room temperature, and extracted by using dichloromethane/water (MC/H$_2$O). The organic layer was dried by using magnesium sulfate (MgSO$_4$) and then concentrated. The crude product was purified by column chromatography (hexane/ethyl acetate=3/1) to obtain Intermediate 1-4 (yield=65%).

Synthesis of Intermediate 1-3

14.8 g (60 mmol) of Intermediate 1-4, 16.0 g (90 mmol) of diphenylacetylene, 16.9 g (126 mmol) of CuCl$_2$, and 0.78 g (3.0 mmol) of bis(acetonitrile)dichloropalladium (Pd(CH$_3$CN)$_2$Cl$_2$) were added to a flask, 300 mL of DMF was added thereto, and the flask was purged with nitrogen. Then, the resultant mixture was allowed to react at a temperature of 105° C. for 12 hours. Then, the mixture was cooled to room temperature and extracted by using dichloromethane/water (MC/H$_2$O). The organic layer was dried by using magnesium sulfate (MgSO$_4$) and concentrated. The crude product was purified by column chromatography (hexane/ethyl acetate=20/1) to obtain Intermediate 1-3 (yield=90%).

Synthesis of Intermediate 1-2

23.4 g (100 mmol) of 2-(3-bromophenyl)pyridine, 9.3 g (100 mmol) of aniline, 2.87 g (5.0 mmol) of bis(dibenzylideneacetone)palladium(0) (Pd(dba)$_2$), 2.0 g (10 mmol) of tri-tert-butylphosphine (P(t-Bu)$_3$), and 14.4 g (150 mmol) of sodium tert-butoxide (NaOtBu) were added to a flask, 200 mL of toluene was added thereto, and the flask was purged with nitrogen. The resultant mixture was refluxed for 24 hours, cooled to room temperature, and extracted by using dichloromethane/water (MC/H$_2$O). The organic layer was dried by using magnesium sulfate (MgSO$_4$) and concentrated. The crude product was purified by column chromatography (hexane/ethyl acetate=3/1) to obtain Intermediate 1-2 (yield=75%).

Synthesis of Intermediate 1-1

Intermediate 1-1 (yield=82%) was synthesized in the same manner in which Intermediate 1-2 was synthesized, except that Intermediate 1-2 was used instead of aniline.

Synthesis of Compound 1

3.38 g (3.5 mmol) of Intermediate 1-1, 0.93 g (3.5 mmol) of platinum chloride, and 100 mL of cyanobenzene were added to a 500-mL round bottom flask, and the mixture was refluxed for 24 hours. After the reaction was completed, the mixture was cooled to room temperature, and the solvent was distilled off under reduced pressure. The crude product was purified by column chromatography by using methylene chloride and normal hexane as a developing solvent to obtain 1.4 g (yield=52%) of Compound 1.

LCMS: m/z calcd for C$_{42}$H$_{28}$N$_4$Pt=783.20; Found [M+H]$^+$=784.29.

Synthesis Example 2: Synthesis of Compound 16

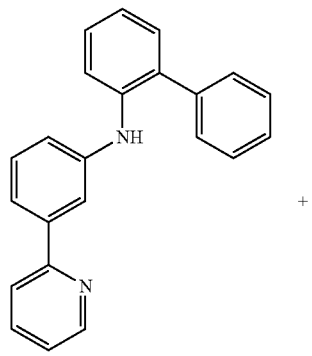

Intermediate 16-2

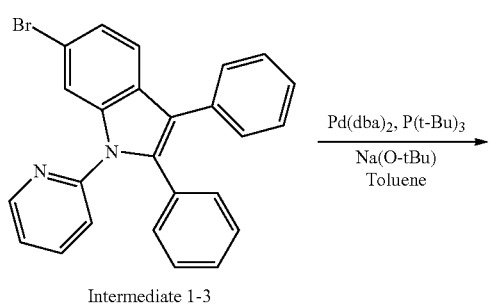

Intermediate 1-3

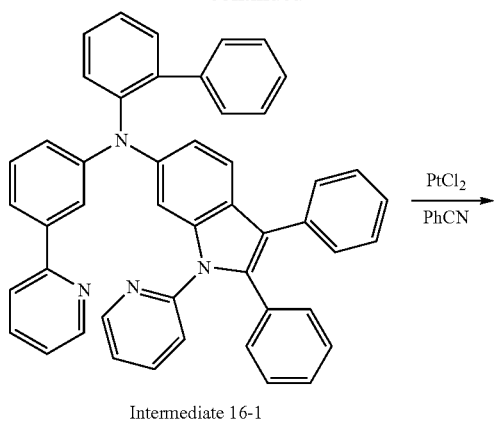

Intermediate 16-1

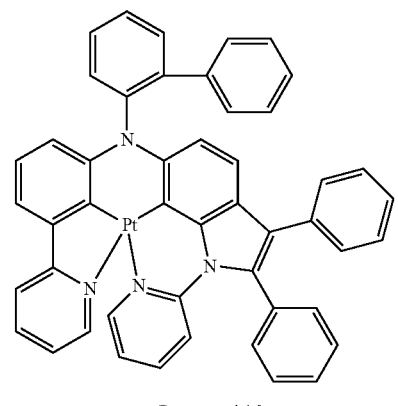

Compound 16

Synthesis of Intermediate 16-1

Intermediate 16-1 (yield=78%) was synthesized in the same manner in which Intermediate 1-1 was synthesized in Synthesis Example 1, except that Intermediate 16-2 was used instead of Intermediate 1-2.

Synthesis of Compound 16

Compound 16 (yield=45%) was synthesized in the same manner in which Compound 1 was synthesized in Synthesis Example 1, except that Intermediate 16-1 was used instead of Intermediate 1-1.

LCMS: m/z calcd for C$_{48}$H$_{32}$N$_4$Pt=859.23; Found [M+H]$^+$=860.27.

Synthesis Example 3: Synthesis of Compound 19

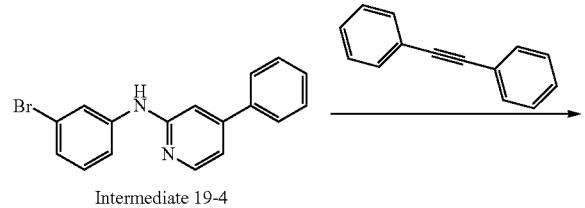

Intermediate 19-4

137
-continued

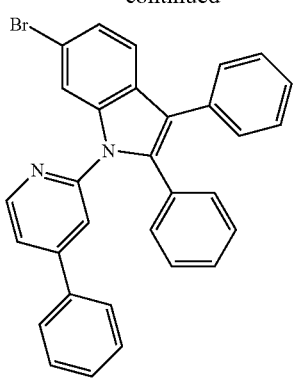

Intermediate 19-3

+

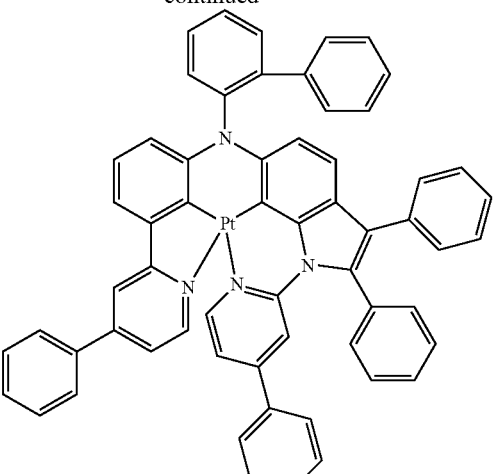

Compound 19

Synthesis of Intermediate 19-3

Intermediate 19-3 (yield=88%) was synthesized in the same manner in which Intermediate 1-3 was synthesized in Synthesis Example 1, except that Intermediate 19-4 was used instead of Intermediate 1-4.

Synthesis of Intermediate 19-1

Intermediate 19-1 (yield=75%) was synthesized in the same manner in which Intermediate 1-1 was synthesized in Synthesis Example 1, except that Intermediate 19-2 and Intermediate 19-3 were respectively used instead of Intermediate 1-2 and Intermediate 1-3.

Synthesis of Compound 19

Compound 19 (yield=47%) was synthesized in the same manner in which Compound 1 was synthesized in Synthesis Example 1, except that Intermediate 19-1 was used instead of Intermediate 1-1.

LCMS: m/z calcd for $C_{60}H_{40}N_4Pt$=1011.29; Found $[M+H]^+$=1012.34.

Synthesis Example 4: Synthesis of Compound 45

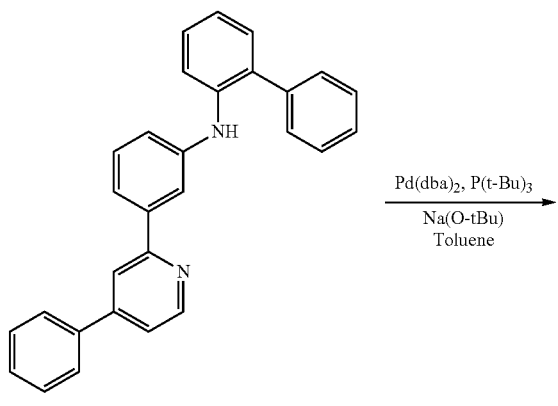

Intermediate 19-2

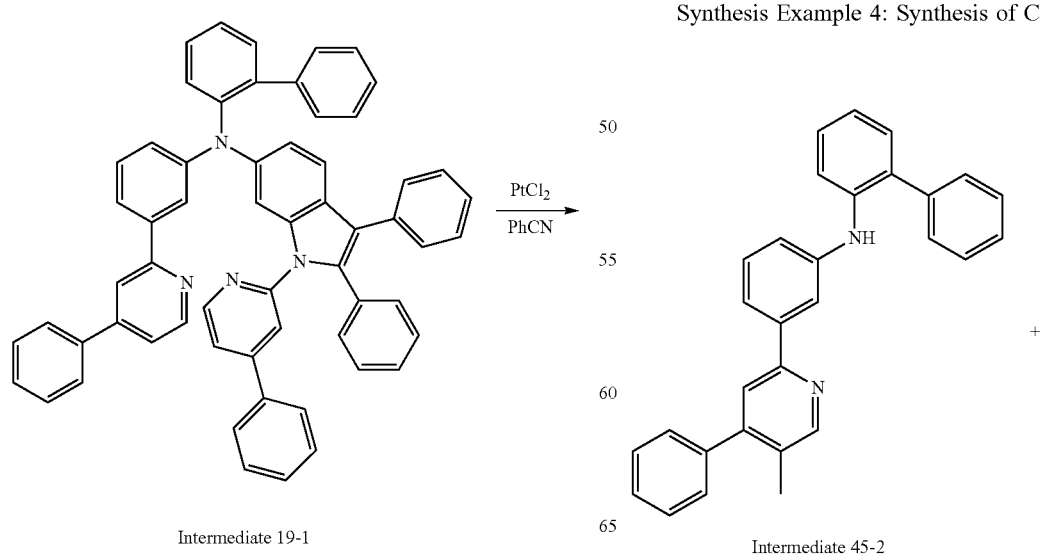

Intermediate 19-1

Intermediate 45-2

-continued

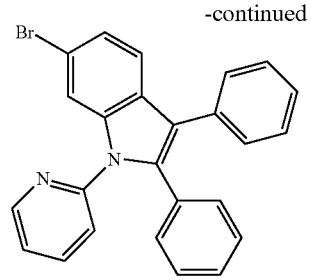

Intermediate 1-3

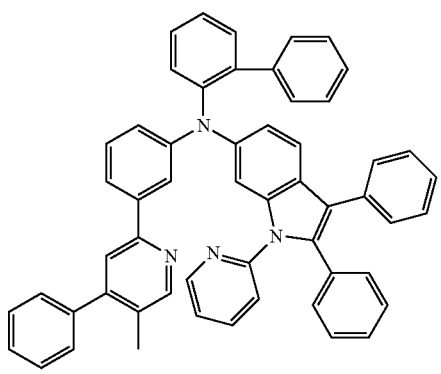

Intermediate 45-1

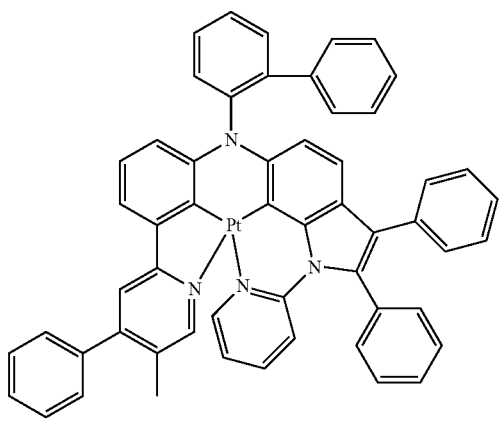

Compound 45

Synthesis of Intermediate 45-1

Intermediate 45-1 (yield=80%) was synthesized in the same manner in which Intermediate 1-1 was synthesized in Synthesis Example 1, except that Intermediate 45-2 was used instead of Intermediate 1-2.

Synthesis of Compound 45

Compound 45 (yield=43%) was synthesized in the same manner in which Compound 1 was synthesized in Synthesis Example 1, except that Intermediate 45-1 was used instead of Intermediate 1-1.

LCMS: m/z calcd for $C_{55}H_{38}N_4Pt$=949.27; Found $[M+H]^+$=948.27.

Synthesis Example 5: Synthesis of Compound 49

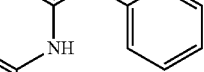

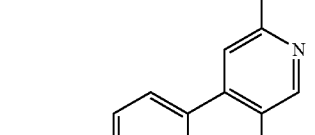

Intermediate 49-2

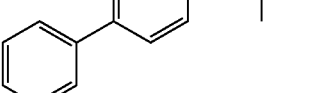

Intermediate 1-3

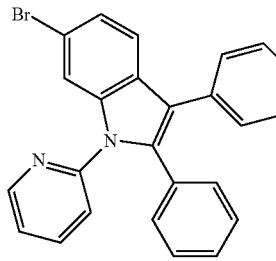

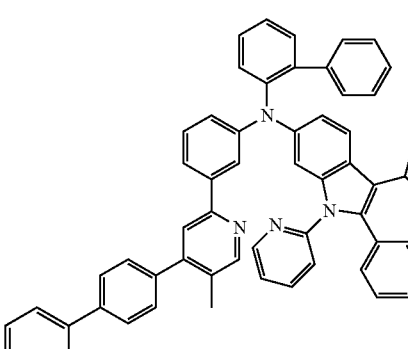

Intermediate 49-1

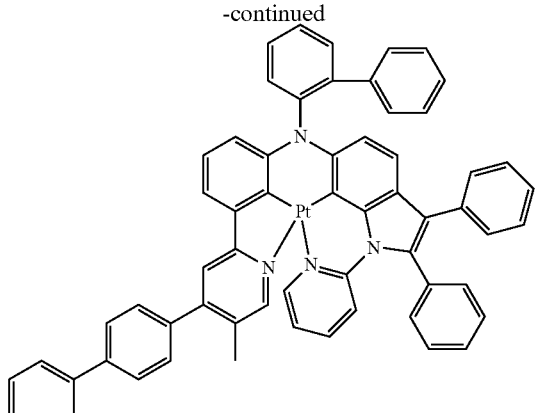

Compound 49

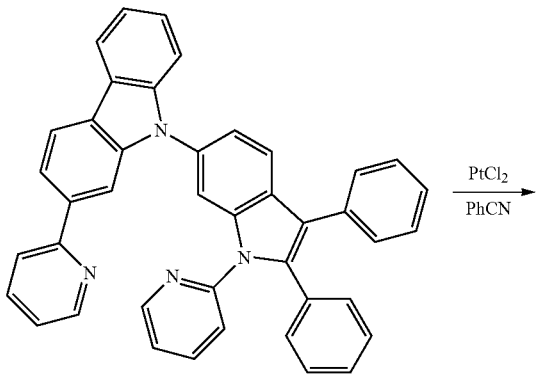

Intermediate 72-1

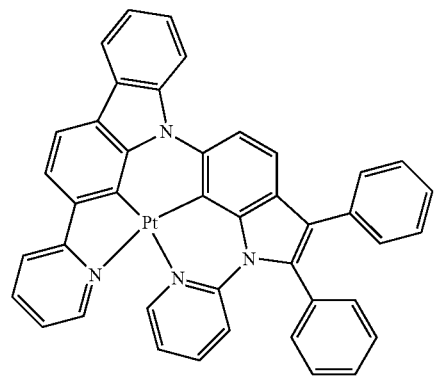

Compound 72

Synthesis of Intermediate 49-1

Compound 49-1 (yield=81%) was synthesized in the same manner in which Intermediate 1-1 was synthesized in Synthesis Example 1, except that Intermediate 49-2 was used instead of Intermediate 1-2.

Synthesis of Compound 49

Compound 49 (yield=47%) was synthesized in the same manner in which Compound 1 was synthesized in Synthesis Example 1, except that Intermediate 49-1 was used instead of Intermediate 1-1.

LCMS: m/z calcd for $C_{61}H_{42}N_4Pt$=1025.31; Found $[M+H]^+$=1026.34.

Synthesis Example 6: Synthesis of Compound 72

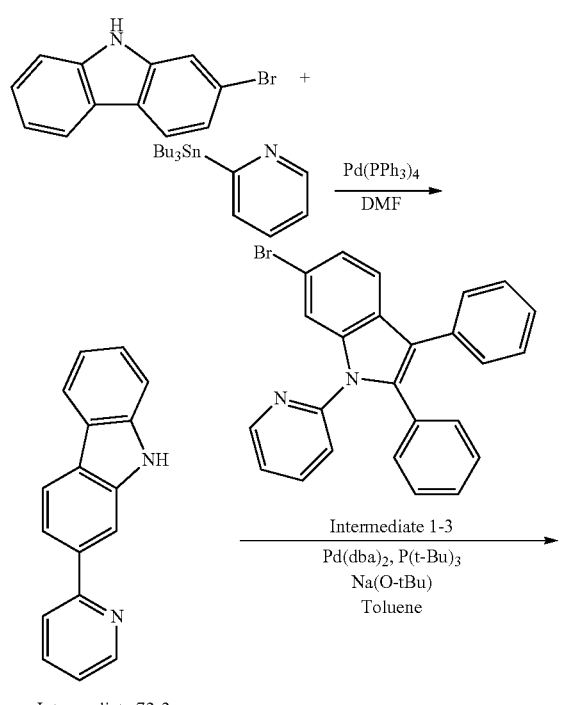

Intermediate 72-2

Synthesis of Intermediate 72-2

19.7 g (80 mmol) of 2-bromo-9H-carbazole, 31.3 g (85 mmol) of 2-(tributylstannyl)pyridine, and 4.62 g (4 mmol) of tetrakis(triphenylphosphine)palladium(0) (Pd(PPh$_3$)$_4$) were added to a flask, 160 mL of DMF was added thereto, and the flask was purged with nitrogen. The resultant mixture was refluxed for 24 hours, cooled to room temperature, and extracted by using dichloromethane/water (MC/H$_2$O). The organic layer was dried by using magnesium sulfate (MgSO$_4$) and concentrated. The crude product was purified by column chromatography (hexane/methylene chloride=3/1) to obtain Intermediate 72-2 (yield=59%).

Synthesis of Intermediate 72-1

Intermediate 72-1 (yield=75%) was synthesized in the same manner in which Intermediate 1-1 was synthesized in Synthesis Example 1, except that Intermediate 72-2 was used instead of Intermediate 1-2.

Synthesis of Compound 72

Compound 72 (yield=42%) was synthesized in the same manner in which Compound 1 was synthesized in Synthesis Example 1, except that Intermediate 72-1 was used instead of Intermediate 1-1.

LCMS: m/z calcd for $C_{42}H_{26}N_4Pt$=781.18; Found $[M+H]^+$=782.29.

Comparative Synthesis Example A: Synthesis of Compound A

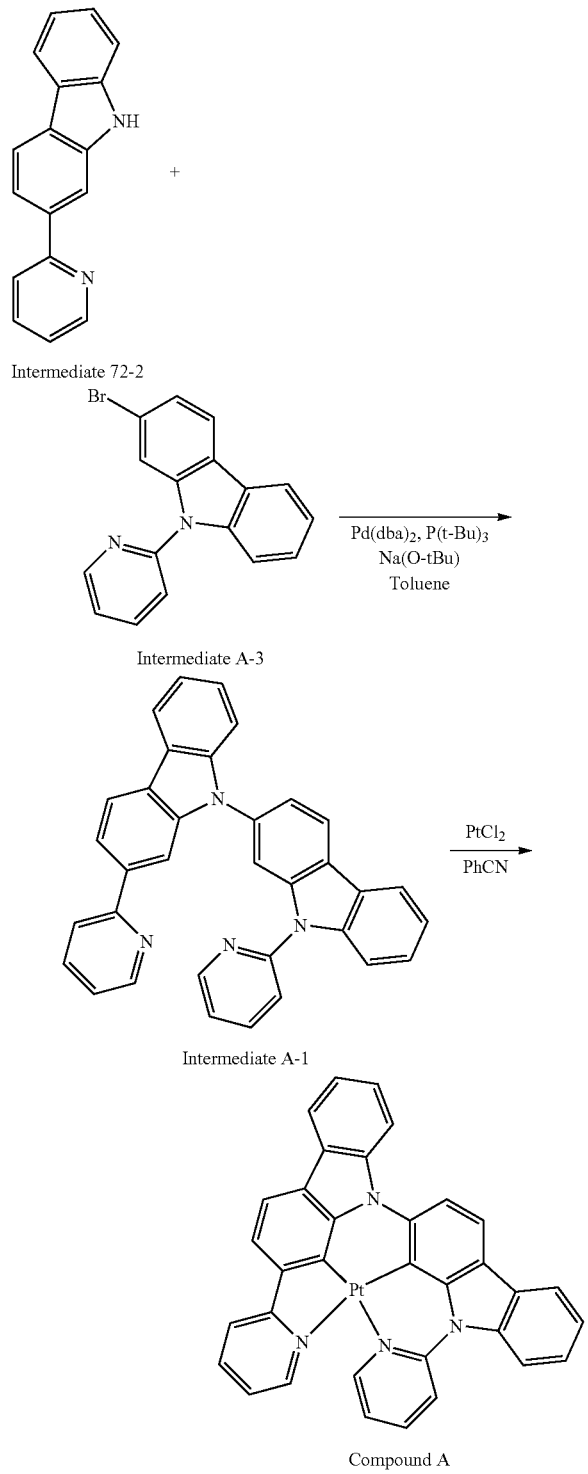

Synthesis of Intermediate A-1

Intermediate A-1 (yield=74%) was synthesized in the same manner in which Intermediate 72-1 was synthesized in Synthesis Example 6, except that Intermediate A-3 was used instead of Intermediate 1-3.

Synthesis of Compound A

Compound A (yield=38%) was synthesized in the same manner in which Compound 1 was synthesized in Synthesis Example 1, except that Intermediate A-1 was used instead of Intermediate 1-1.

LCMS: m/z calcd for $C_{34}H_{20}N_4Pt$=679.13; Found $[M+H]^+$=680.17.

Comparative Synthesis Example B: Synthesis of Compound B

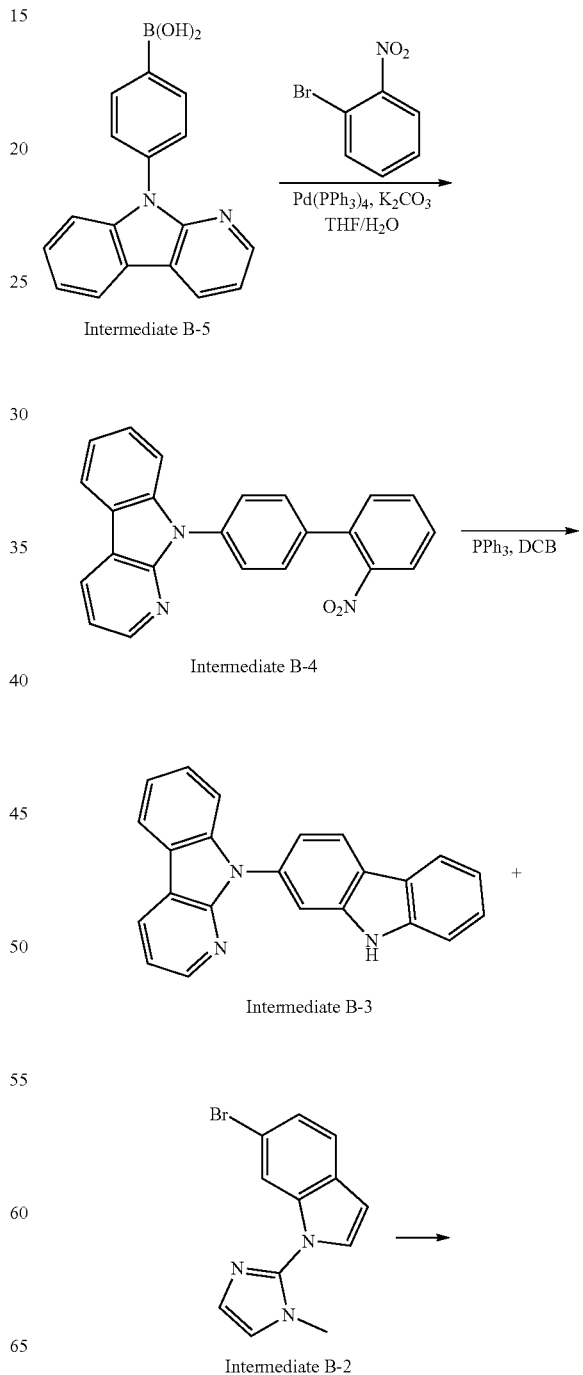

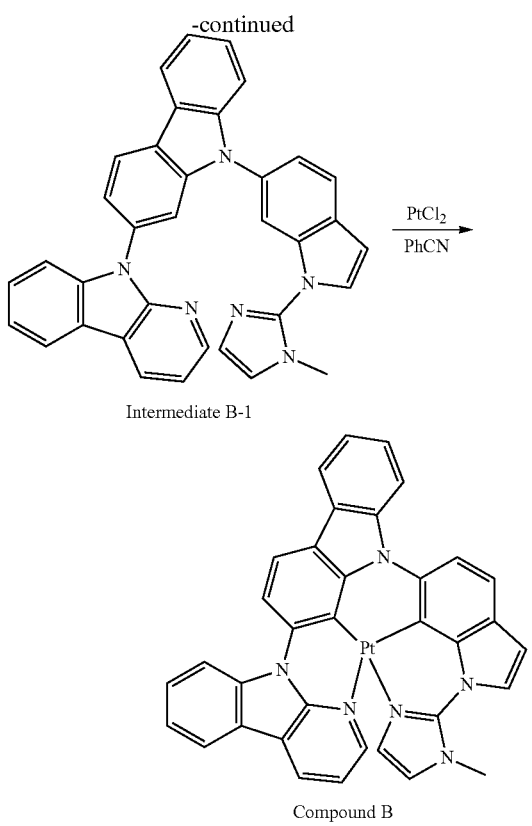

Intermediate B-1

Compound B

Synthesis of Intermediate B-4

14.4 g (50 mmol) of Intermediate B-5, 10.1 g (50 mmol) of 1-bromo-2-nitrobenzene, 17.3 g (125 mmol) of $K_2CO_3$, and 2.9 g (2.5 mmol) of tetrakis(triphenylphosphine)palladium(0) $(Pd(PPh_3)_4)$ were added to a flask, and 150 mL of $THF/H_2O$ (3/1) was added thereto. The resultant mixture was refluxed for 24 hours, cooled to room temperature, and extracted by using ethyl acetate/water ($EA/H_2O$). The organic layer was dried by using magnesium sulfate ($MgSO_4$) and concentrated. The crude product was purified by column chromatography (hexane/methylene chloride=2/1) to obtain Intermediate B-4 (yield=67%).

Synthesis of Intermediate B-3

19 g (52 mmol) of Intermediate B-4 and 54 g (206 mmol) of triphenylphosphine were added to a flask, and 170 mL of dichlorobenzene was added thereto. The resultant mixture was allowed to react at a temperature of 175° C. for 24 hours. The resultant mixture was cooled to room temperature, and the crude product was purified by column chromatography (hexane/methylene chloride=1/1) to obtain a solid. The solid was washed by using methanol to obtain Intermediate B-3 (yield=70%).

Synthesis of Intermediate B-1

Intermediate B-1 (yield=72%) was synthesized in the same manner in which Intermediate 1-1 was synthesized in Synthesis Example 1, except that Intermediate B-2 and Intermediate B-3 were respectively used instead of Intermediate 1-2 and Intermediate 1-3.

Synthesis of Compound B

Compound B(yield=25%) was synthesized in the same manner in which Compound 1 was synthesized in Synthesis Example 1, except that Intermediate B-1 was used instead of Intermediate 1-1.

LCMS: m/z calcd for $C_{35}H_{22}N_6Pt$=721.16; Found $[M+H]^+$=722.21.

Figure 2:
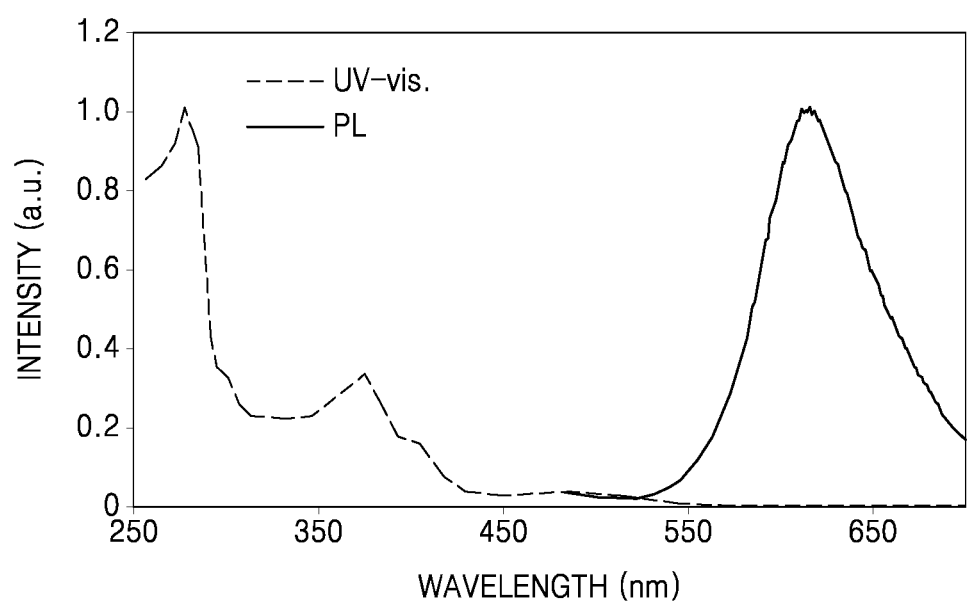
FIG. 2 is a graph of intensity (arbitrary units, a. u.) versus wavelength (nanometers, nm), showing an ultraviolet (UV) absorption spectrum and a photoluminescence (PL) spectrum in solution, with respect to Compound 1.

Evaluation Example 1: Evaluation of UV-Vis Absorption Spectrum and Photoluminescence (PL) Spectrum Luminescent characteristics of each Compound were evaluated by evaluating a UV-Vis absorption spectrum and a PL spectrum of Compound 1. Compound 1 was diluted at a concentration of $1\times10^{-5}$ M in MeTHF, and a UV-Vis absorption spectrum was measured at room temperature by using a Shimadzu UV-350 spectrometer. Compound 1 was diluted at a concentration of 10 mM in MeTHF, and a PL spectrum thereof was measured at room temperature by using an ISC PC1 spectrofluorometer equipped with a xenon lamp. Results thereof are shown in Table 2. Referring to FIG. 2, it is confirmed that Compound 1 has a UV-Vis absorption spectrum and a PL spectrum suitable for use in an electronic device, for example, an organic light-emitting device.

Evaluation Example 2: Measurement of Decay Time

A quartz substrate washed with chloroform and distilled water was prepared, and films 1 to 6, A, and B, each having a thickness of 50 nm, were prepared by vacuum-depositing (co-depositing) certain materials shown in Table 2 below at a degree of vacuum of $10^{-7}$ torr.

TABLE 2

| Film name | Compound used to manufacture film |
|---|---|
| Film 1 | CBP:Compound 1 (weight ratio of 9:1) |
| Film 2 | CBP:Compound 16 (weight ratio of 9:1) |
| Film 3 | CBP:Compound 19 (weight ratio of 9:1) |
| Film 4 | CBP:Compound 45 (weight ratio of 9:1) |
| Film 5 | CBP:Compound 49 (weight ratio of 9:1) |
| Film 6 | CBP:Compound 72 (weight ratio of 9:1) |
| Film A | CBP:Compound A (weight ratio of 9:1) |
| Film B | CBP:Compound B (weight ratio of 9:1) |

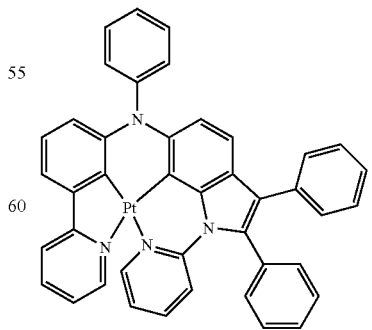

1

TABLE 2-continued

| Film name | Compound used to manufacture film |
|---|---|
| 16 | (structure) |
| 19 | (structure) |
| 45 | (structure) |
| 49 | (structure) |
| 72 | (structure) |
| A | (structure) |
| B | (structure) |

Then, PL spectra of the films 1 to 6, A, and B prepared as described above were evaluated at room temperature by using a time-resolved photoluminescence (TRPL) measurement system FluoTime 300 (manufactured by PicoQuant) and a pumping source PLS340 (excitation wavelength=340 nanometers (nm), spectral width=20 nm) (manufactured by PicoQuant), wavelengths of main peaks of the PL spectra were determined, and the number of photons emitted from each film at the main peak by a photon pulse (pulse width=500 picoseconds, ps) applied to each film by PLS340 was measured over time using Time-Correlated Single Photon Counting (TCSPC). By repeating the above processes, a sufficiently fittable TRPL curve was obtained. Then, a decay time value $T_{decay}(Ex)$ of each of the films 1 to 5, A, and B was obtained by fitting two or more exponential decay functions to a result obtained from the TRPL curve. Results thereof are shown in Table 3. A function represented by Equation 1 was used for the fitting, and a greatest value among values $T_{decay}$ obtained from the exponential decay functions used for the fitting was taken as $T_{decay}(Ex)$. At this time, the same measurement was performed once more for the same measurement time as that for calculating the TRPL curve in a dark state (a state in which the pumping signal input to a certain film was blocked) to obtain a baseline or background signal curve. The baseline or background curve was used as a baseline for fitting.

$$f(t) = \sum_{i=1}^{n} A_i \exp(-t/T_{decay,i})$$  Equation 1

TABLE 3

| Film name | Decay time (micrometers, μm) |
|---|---|
| Film 1 | 7.08 |
| Film 2 | 7.01 |
| Film 3 | 5.98 |
| Film 4 | 6.72 |
| Film 5 | 6.14 |
| Film 6 | 8.78 |
| Film A | 9.01 |
| Film B | 9.58 |

Referring to Table 3, it is confirmed that Compounds 1, 16, 19, 45, 49, and 72 each have a shorter decay time, as compared with Compounds A and B.

Example 1

As an anode, a glass substrate, on which ITO/Ag/ITO were respectively deposited to thicknesses of 70 Å/1,000 Å/70 Å (Å=Angstrom), was cut to a size of 50 mm×50 mm×0.5 mm (mm=millimeter), sonicated with iso-propyl alcohol and pure water each for 5 minutes, and then cleaned by exposure to ultraviolet rays and ozone for 30 minutes. Then, the glass substrate was provided to a vacuum deposition apparatus.

2-TNATA was deposited on the anode to form a hole injection layer having a thickness of 600 Å, and 4,4'-bis[N-(1-naphthyl)-N-phenylamino]biphenyl (NPB) was deposited on the hole injection layer to form a hole transport layer having a thickness of 1,350 Å.

CBP (host) and Compound 1 (dopant) were co-deposited on the hole transport layer at a weight ratio of 98:2 to form an emission layer having a thickness of 400 Å, and BCP was deposited on the emission layer to form a hole blocking layer having a thickness of 50 Å. Then, Alq$_3$ was deposited on the hole blocking layer to form an electron transport layer having a thickness of 350 Å, LiF was deposited on the electron transport layer to form an electron injection layer having a thickness of 10 Å, and MgAg was deposited on the electron injection layer at a weight ratio of 90:10 to form a cathode having a thickness of 120 Å, thereby completing the manufacture of an organic light-emitting device (emitting red color light) having a structure of ITO/Ag/ITO/2-TNATA (600 Å)/NPB (1,350 Å)/CBP+Compound 1 (2 wt %) (400 Å)/BCP (50 Å)/Alq$_3$ (350 Å)/LiF(10 Å)/MgAg (120 Å).

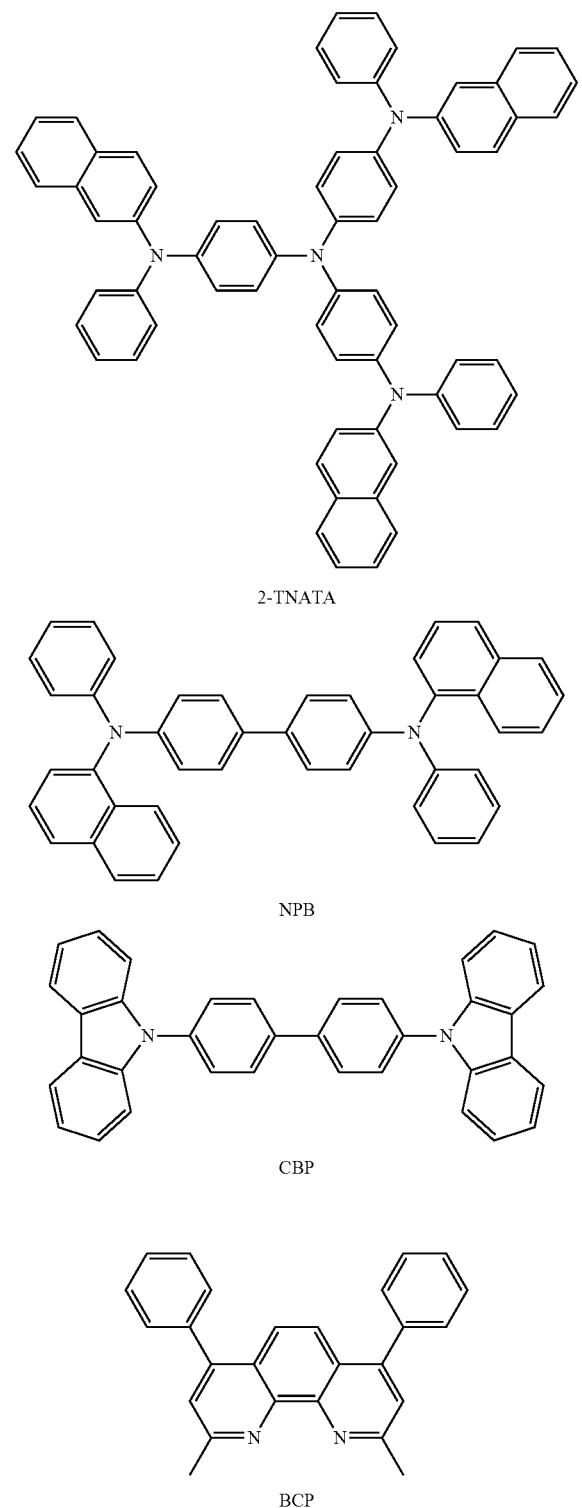

2-TNATA

NPB

CBP

BCP

-continued

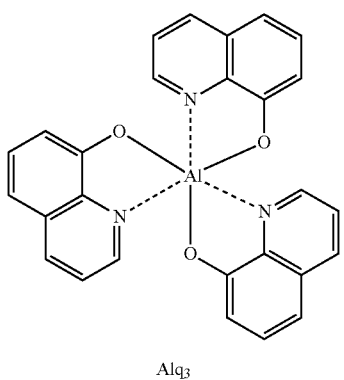

Alq₃

Examples 2 to 6 and Comparative Examples A and B

Organic light-emitting devices were manufactured in the same manner as in Example 1, except that Compounds shown in Table 4 were each used instead of Compound 1 as a dopant in forming an emission layer.

Figure 3:
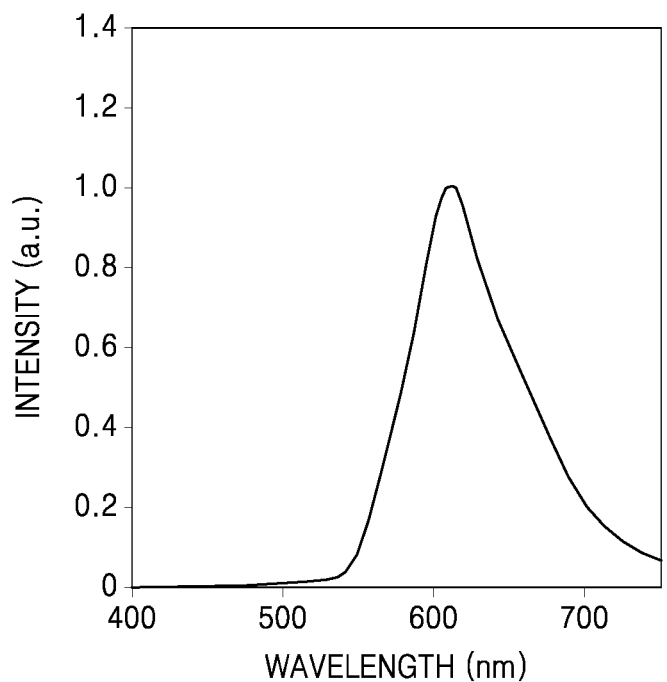
FIG. 3 is a graph of intensity (arbitrary units, a. u.) versus wavelength (nanometers, nm), showing an electroluminescence (EL) spectrum of an organic light-emitting device manufactured according to Example 1.
Figure 4:
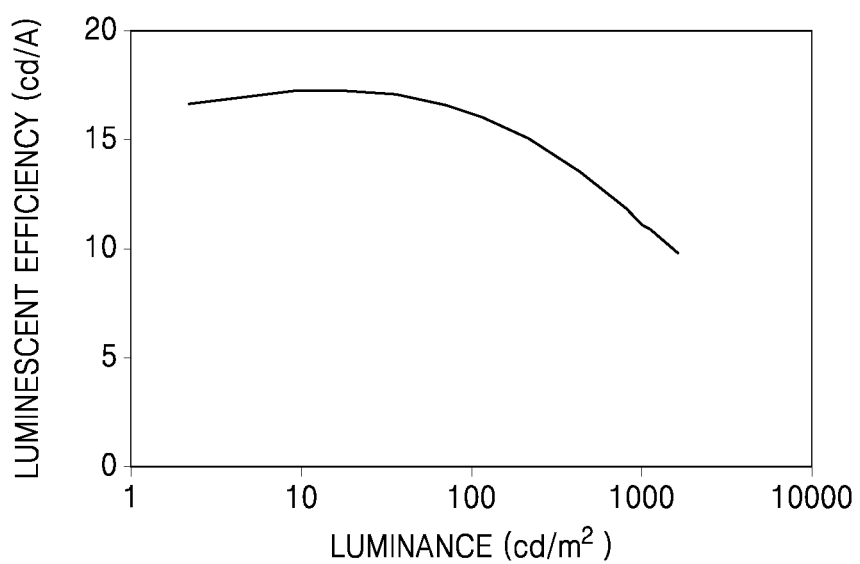
FIG. 4 is a graph of luminescent efficiency (candelas per ampere, cd/A) vs. luminance (candelas per square meter) of an organic light-emitting device manufactured according to Example 1.

Evaluation Example 3: Evaluation of Characteristics of Organic Light-Emitting Devices The driving voltage, maximum luminescence quantum efficiency, maximum emission wavelength, and color purity of the organic light-emitting devices manufactured according to Examples 1 to 6 and Comparative Examples A and B were evaluated, and results thereof are shown in Table 4. This evaluation was performed by using a current-voltage meter (Keithley 2400) and a luminance meter (Minolta Cs-1,000A). FIGS. 3 and 4 respectively show an EL spectrum and a graph of luminance vs. luminescent efficiency of the organic light-emitting device manufactured according to Example 1.

TABLE 4

| | Dopant | Driving voltage (V) | Maximum luminescence quantum efficiency (%) | Maximum emission wavelength (nm) | CIE_x |
|---|---|---|---|---|---|
| Example 1 | Compound 1 | 4.97 | 17.2 | 613 | 0.635 |
| Example 2 | Compound 16 | 4.91 | 18.5 | 611 | 0.633 |
| Example 3 | Compound 19 | 4.85 | 20.5 | 625 | 0.657 |
| Example 4 | Compound 45 | 4.75 | 18.3 | 615 | 0.652 |
| Example 5 | Compound 49 | 4.64 | 19.1 | 613 | 0.635 |
| Example 6 | Compound 72 | 4.27 | 16.7 | 596 | 0.598 |
| Comparative Example A | Compound A | 4.67 | 15.8 | 554 | 0.346 |
| Comparative Example B | Compound B | 5.06 | 16.5 | 532 | 0.257 |

TABLE 4-continued

| Dopant | Driving voltage (V) | Maximum luminescence quantum efficiency (%) | Maximum emission wavelength (nm) | CIE_x |
|---|---|---|---|---|

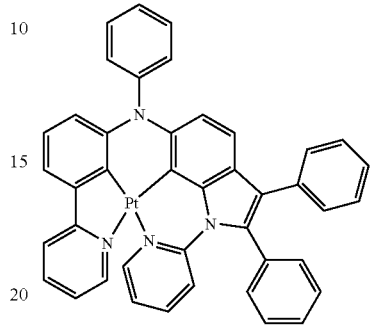

1

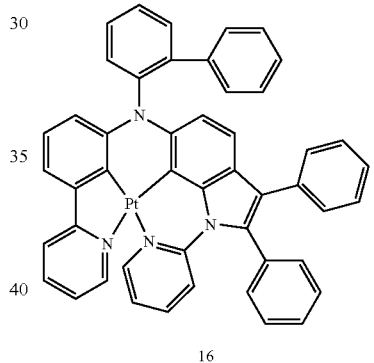

16

19

TABLE 4-continued

| Dopant | Driving voltage (V) | Maximum luminescence quantum efficiency (%) | Maximum emission wavelength (nm) | CIE_x |
|---|---|---|---|---|

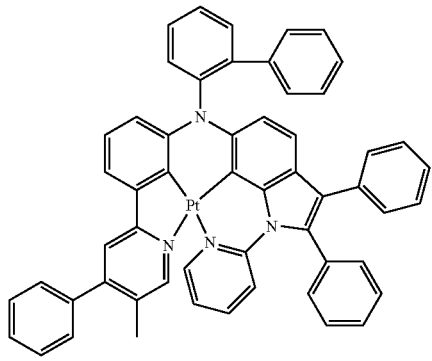

45

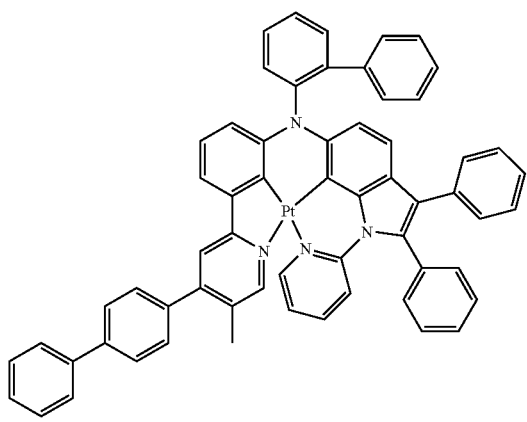

49

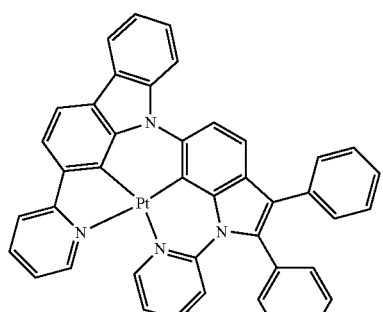

72

TABLE 4-continued

| Dopant | Driving voltage (V) | Maximum luminescence quantum efficiency (%) | Maximum emission wavelength (nm) | CIE_x |
|---|---|---|---|---|

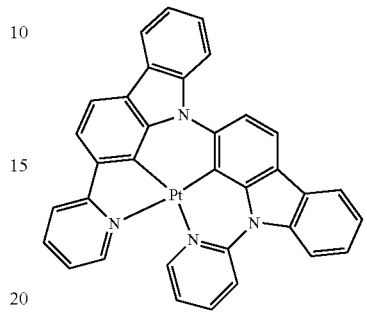

A

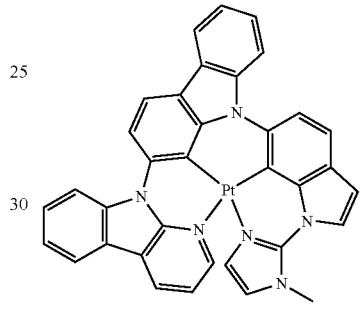

B

Referring to Table 4, it is confirmed that the organic light-emitting devices of Examples 1 to 6 have improved maximum luminescence quantum efficiency and can emit red light having excellent color purity, as compared to the organic light-emitting devices of Comparative Examples A and B.

As described above, the organometallic compounds according to the embodiments of the present disclosure have excellent electrical characteristics and thermal stability, and accordingly, organic light-emitting devices including such organometallic compounds may have excellent driving voltage, efficiency, power, color purity, and lifespan characteristics. Also, due to excellent phosphorescent luminescence characteristics, such organometallic compounds may provide a diagnostic composition having high diagnostic efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:
1. An organometallic compound represented by Formula 1:

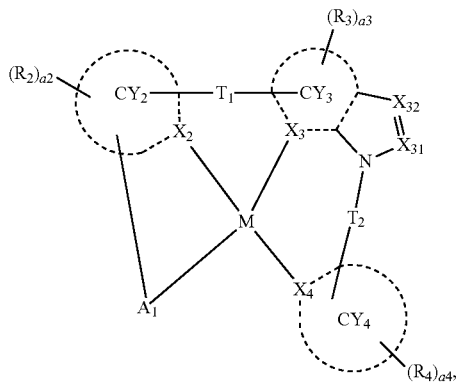

Formula 1 wherein, in Formula 1,
M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au),
two bonds selected from a bond between $A_1$ and M, a bond between $X_2$ and M, a bond between $X_3$ and M, and a bond between $X_4$ and M are each a covalent bond, and the others thereof are each a coordinate bond,
$A_1$ is a first atom linked to M, a non-cyclic moiety comprising the first atom linked to M, or ring $CY_1$ comprising $X_1$ linked to M and substituted with groups $R_1$ in the number of a1,
the first atom is B, N, P, C, Si, O, or S,
$X_1$ and $X_2$ are each independently N or C, $X_3$ is C and $X_4$ is N,
rings $CY_1$ to $CY_4$ are each independently selected from a $C_5$-$C_{30}$ carbocyclic group and a $C_1$-$C_{30}$ heterocyclic group,
a cyclometalated ring formed by $A_1$, $CY_2$, and M is a 5-membered ring,
$X_{31}$ is $C(R_{31})$ or N, and $X_{32}$ is $C(R_{32})$ or N, wherein, when $X_{31}$ is $C(R_{31})$ and $X_{32}$ is $C(R_{32})$, $R_{31}$ and $R_{32}$ are not linked to each other,
$T_1$ and $T_2$ may each independently be selected from a single bond, a double bond, *—N($R_5$)—*', *—B($R_5$)—*', *—P($R_5$)—*', *—C($R_5$)($R_6$)—*', *—Si($R_5$)($R_6$)—*', *—Ge($R_5$)($R_6$)—*', *—S—*', *—Se—*', *—O—*', *—C(=O)—*', *—S(=O)—*', *—S(=O)$_2$—*', *—C($R_5$)=*', *'=C($R_5$)—*', C($R_5$)=C($R_6$)—*', *—C(=S)—*', and *—C≡C—*', and * and *' each indicate a binding site to a neighboring atom,
$R_5$ and $R_6$ may optionally be linked via a single bond, a double bond, or a first linking group to form a substituted or unsubstituted $C_5$-$C_{30}$ carbocyclic group or a substituted or unsubstituted $C_1$-$C_{30}$ heterocyclic group,
$R_1$ to $R_6$, $R_{31}$, and $R_{32}$ may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$),
$a_1$ to $a_4$ are each independently an integer from 0 to 20,
two of a plurality of neighboring groups $R_1$ are optionally linked to form a substituted or unsubstituted $C_5$-$C_{30}$ carbocyclic group or a substituted or unsubstituted $C_1$-$C_{30}$ heterocyclic group,
two of a plurality of neighboring groups $R_2$ are optionally linked to form a substituted or unsubstituted $C_5$-$C_{30}$ carbocyclic group or a substituted or unsubstituted $C_1$-$C_{30}$ heterocyclic group,
two of a plurality of neighboring groups $R_3$ are optionally linked to form a substituted or unsubstituted $C_5$-$C_{30}$ carbocyclic group or a substituted or unsubstituted $C_1$-$C_{30}$ heterocyclic group,
two of a plurality of neighboring groups $R_4$ are optionally linked to form a substituted or unsubstituted $C_5$-$C_{30}$ carbocyclic group or a substituted or unsubstituted $C_1$-$C_{30}$ heterocyclic group,
two or more neighboring groups selected from $R_1$ to $R_4$ are optionally linked to form a substituted or unsubstituted $C_5$-$C_{30}$ carbocyclic group or a substituted or unsubstituted $C_1$-$C_{30}$ heterocyclic group,
at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one selected from deuterium, a $C_1$-$C_{60}$ alkyl group, and a $C_6$-$C_{60}$ aryl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from deuterium, a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organometallic compound of claim 1, wherein a bond between $A_1$ and M and a bond between $X_4$ and M are each a coordinate bond, and a bond between $X_2$ and M and a bond between $X_3$ and M are each a covalent bond.

3. The organometallic compound of claim 1, wherein rings $CY_1$ to $CY_4$ are each independently selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzooxadiazole group, a benzothiadiazole group, a 5,6,7,8-tetrahydroisoquinoline group, and a 5,6,7,8-tetrahydroquinoline group.

4. The organometallic compound of claim 1, wherein at least one of rings $CY_2$ and $CY_4$ is a condensed ring with at least one 5-membered ring and at least one 6-membered ring, the 5-membered ring is selected from a cyclopentadiene group, a furan group, a thiophene group, a pyrrole group, a silole group, an oxazole group, an isoxazole group, an oxadiazole group, an isoxadiazole group, an oxatriazole group, an isoxatriazole group, a thiazole group, an isothiazole group, a thiadiazole group, an isothiadiazole group, a thiatriazole group, an isothiatriazole group, a pyrazole group, an imidazole group, a triazole group, a tetrazole group, an azasilole group, a diazasilole group, and a triazasilole group, and the 6-membered ring is selected from a cyclohexane group, a cyclohexene group, a benzene group, a pyridine group, a pyrimidine group, a pyrazine group, and a pyridazine group.

5. The organometallic compound of claim 1, wherein $T_2$ is a single bond.

6. The organometallic compound of claim 1, wherein $R_1$ to $R_6$, $R_{31}$, and $R_{32}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, and —Si($Q_{33}$)($Q_{34}$)($Q_{35}$); and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ and $Q_{33}$ to $Q_{35}$ may each independently be selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

7. The organometallic compound of claim 1, wherein $R_1$ to $R_6$, $R_{31}$, and $R_{32}$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-161, —N($Q_1$)($Q_2$), —Si($Q_3$)($Q_4$)($Q_5$), —B($Q_6$)($Q_7$), and —P(=O)($Q_8$)($Q_9$):

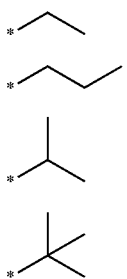

Formula 9-1

Formula 9-2

Formula 9-3

Formula 9-4

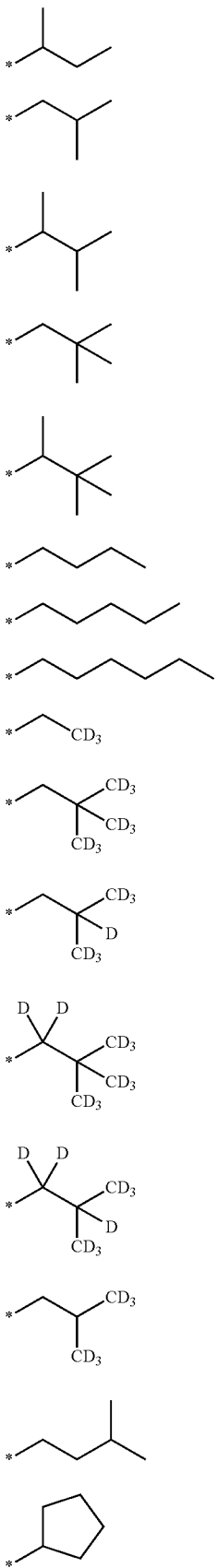
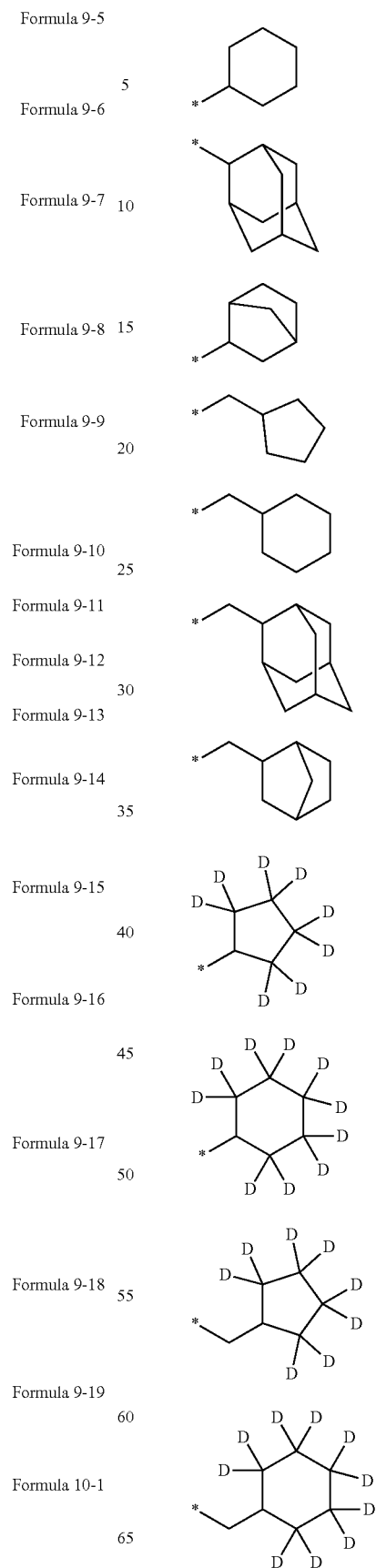

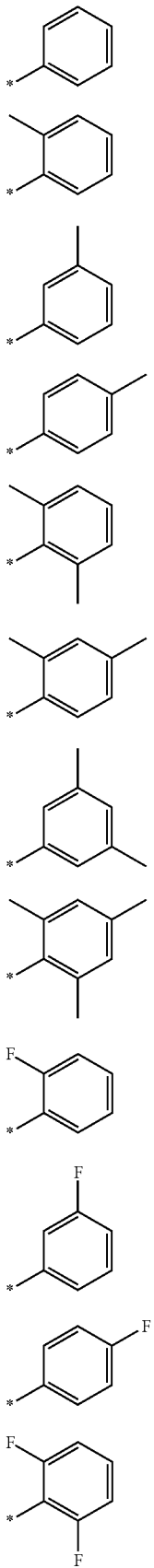
Formula 10-13
Formula 10-14
Formula 10-15
Formula 10-16
Formula 10-17
Formula 10-18
Formula 10-19
Formula 10-20
Formula 10-21
Formula 10-22
Formula 10-23
Formula 10-24
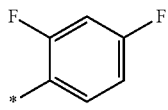
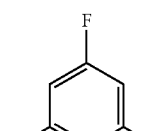
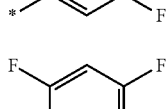
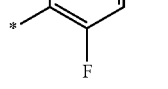
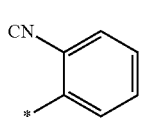
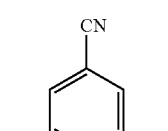
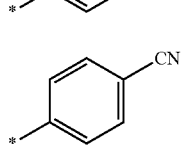
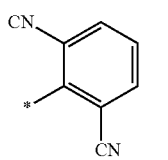
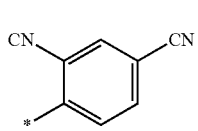
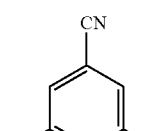
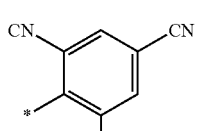
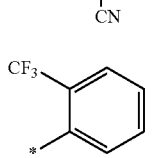
Formula 10-25
Formula 10-26
Formula 10-27
Formula 10-28
Formula 10-29
Formula 10-30
Formula 10-31
Formula 10-32
Formula 10-33
Formula 10-34
Formula 10-35

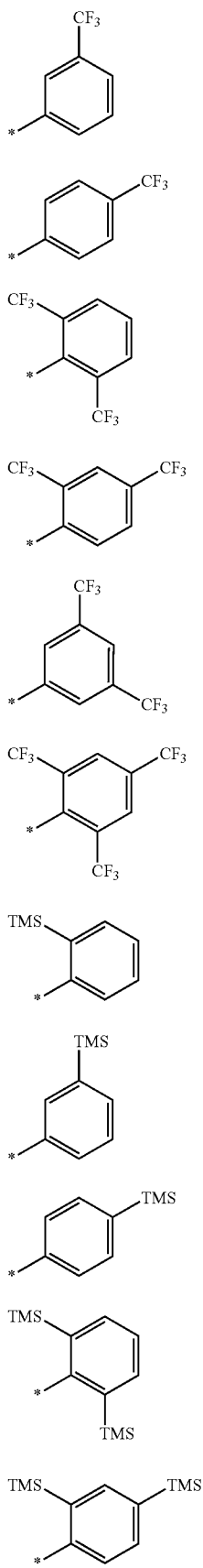
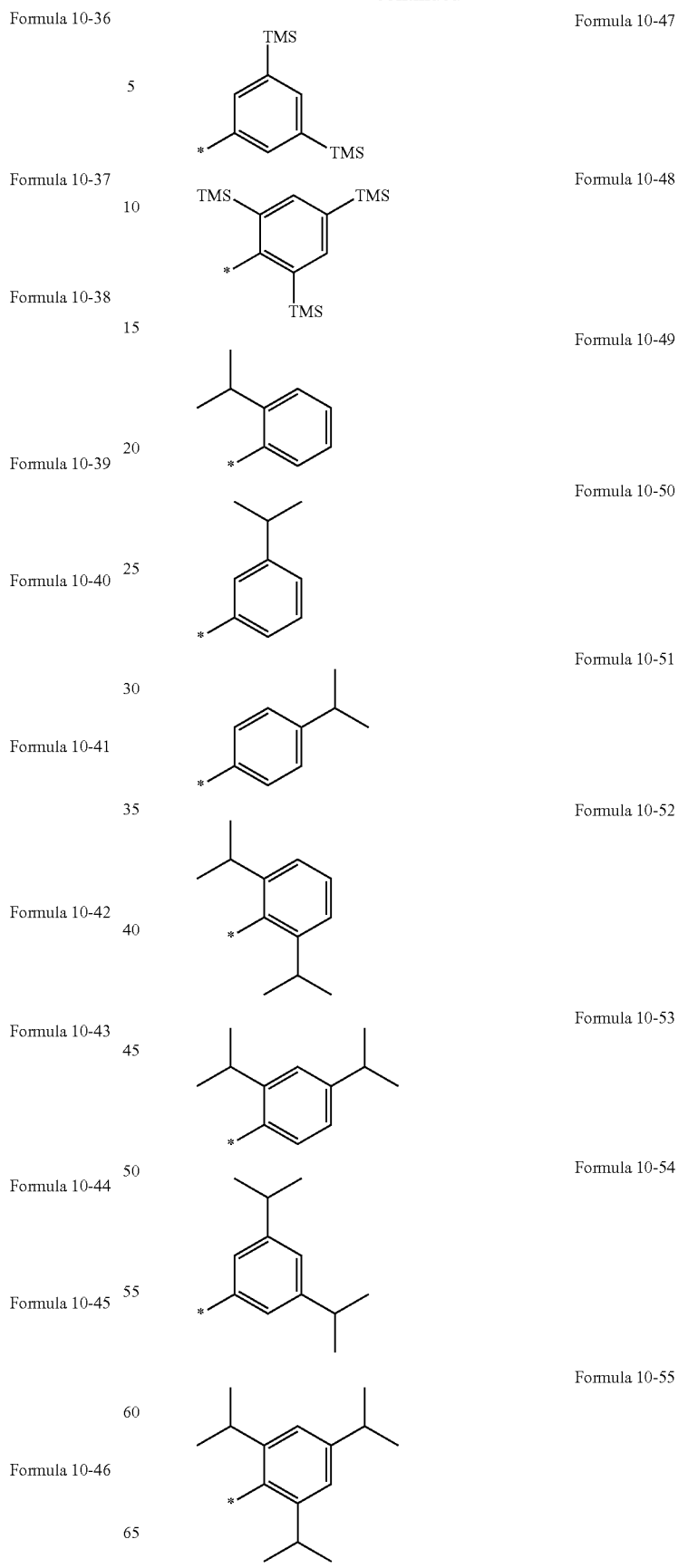

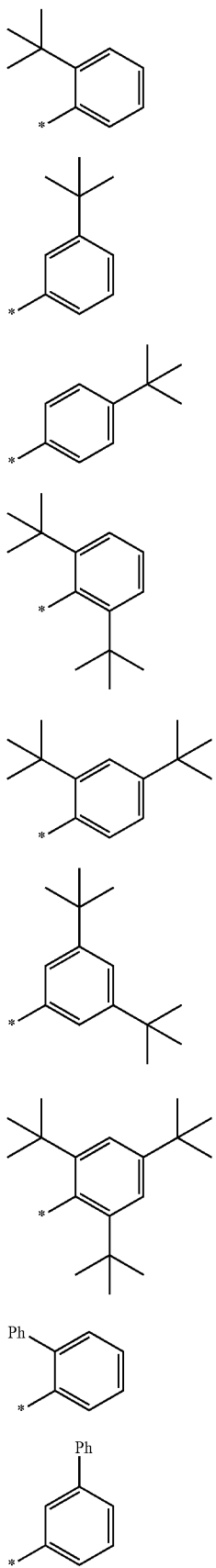
Formula 10-56
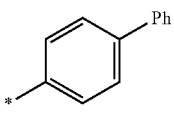
Formula 10-65
Formula 10-57
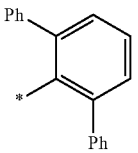
Formula 10-66
Formula 10-58
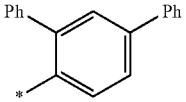
Formula 10-67
Formula 10-59
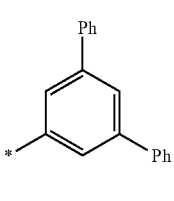
Formula 10-68
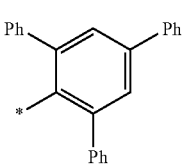
Formula 10-69
Formula 10-60
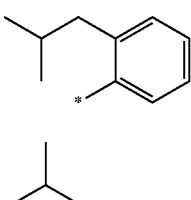
Formula 10-70
Formula 10-61
Formula 10-71
Formula 10-62
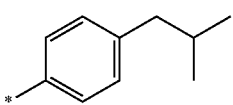
Formula 10-72
Formula 10-63
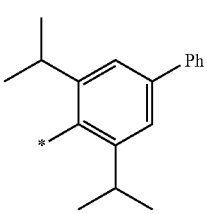
Formula 10-73
Formula 10-64
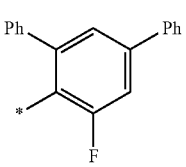
Formula 10-74

Formula 10-75
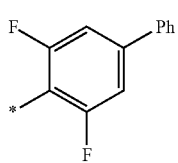
Formula 10-76
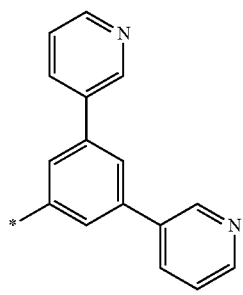
Formula 10-77
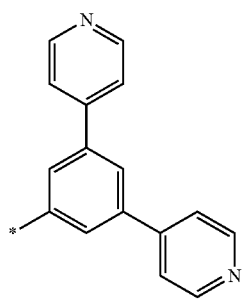
Formula 10-78
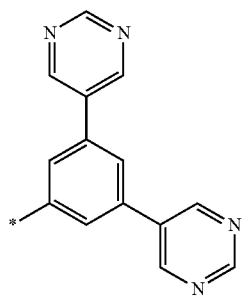
Formula 10-79
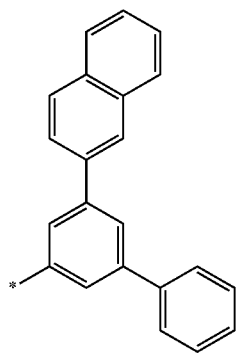
Formula 10-80
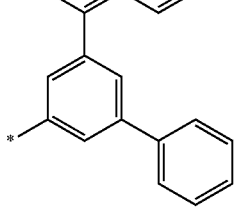
Formula 10-81
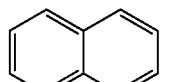
Formula 10-82
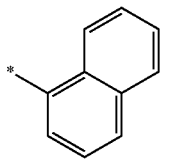
Formula 10-83
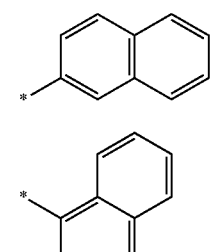
Formula 10-84
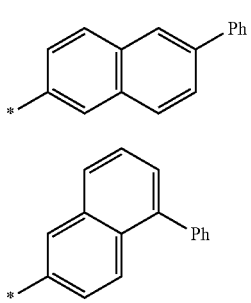
Formula 10-85
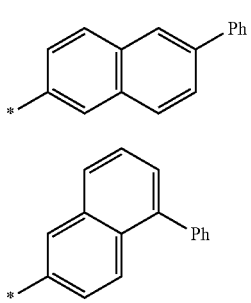
Formula 10-86
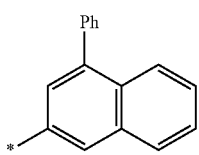
Formula 10-87
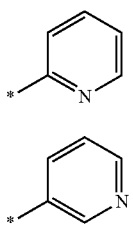
Formula 10-88
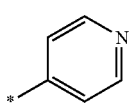
Formula 10-89
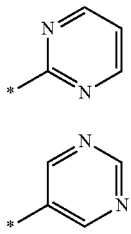
Formula 10-90
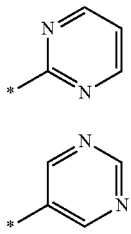

-continued
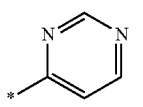
Formula 10-91
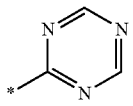
Formula 10-92
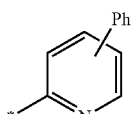
Formula 10-93
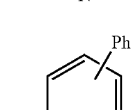
Formula 10-94
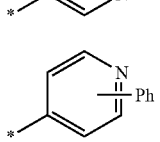
Formula 10-95
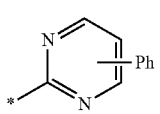
Formula 10-96
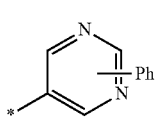
Formula 10-97
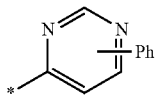
Formula 10-98
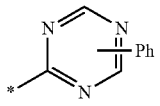
Formula 10-99
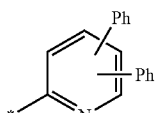
Formula 10-100
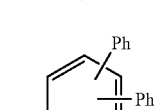
Formula 10-101
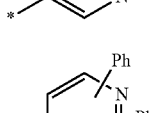
Formula 10-102
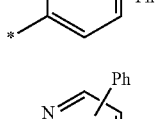
Formula 10-103
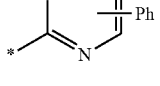
-continued
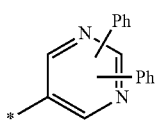
Formula 10-104
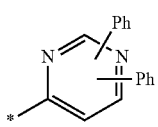
Formula 10-105
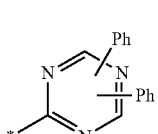
Formula 10-106
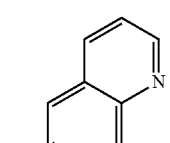
Formula 10-107
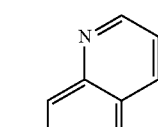
Formula 10-108
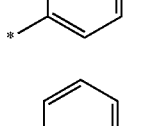
Formula 10-109
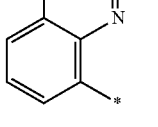
Formula 10-110
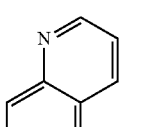
Formula 10-111
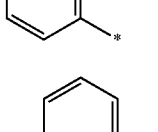
Formula 10-112
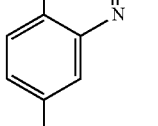
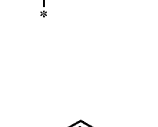
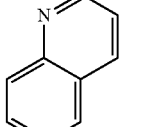

Formula 10-113
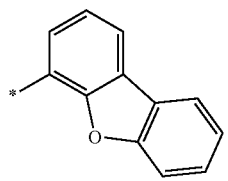
Formula 10-114
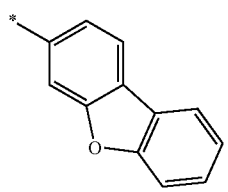
Formula 10-115
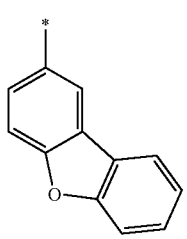
Formula 10-116
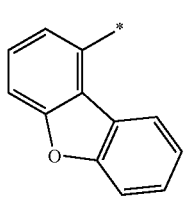
Formula 10-117
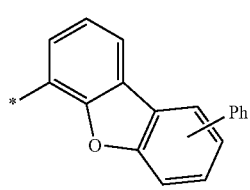
Formula 10-118
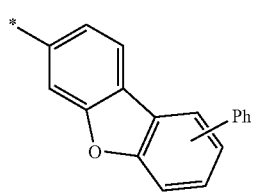
Formula 10-119
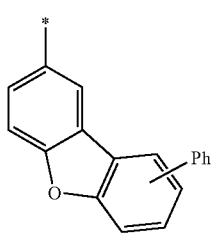
Formula 10-120
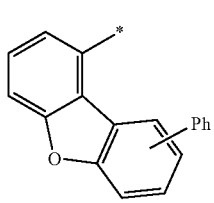
Formula 10-121
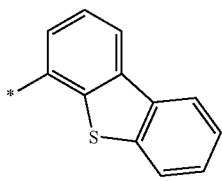
Formula 10-122
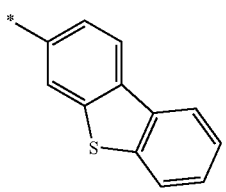
Formula 10-123
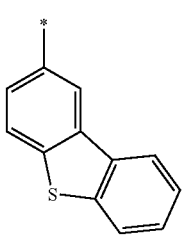
Formula 10-124
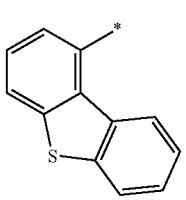
Formula 10-125
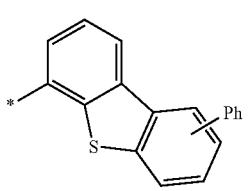
Formula 10-126
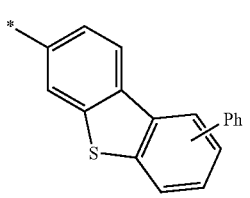
Formula 10-127
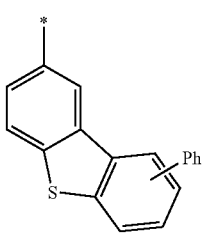
Formula 10-128
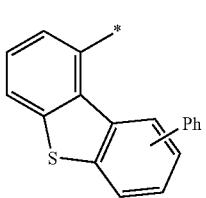

US 10,950,807 B2
| | |
|---|---|
| 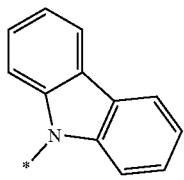 | 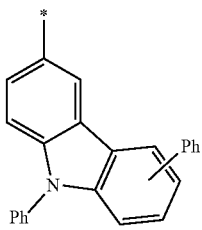 Formula 10-137 |
| 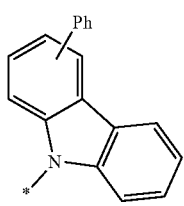 Formula 10-130 | 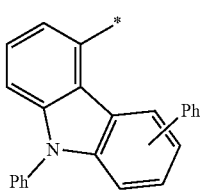 Formula 10-138 |
| 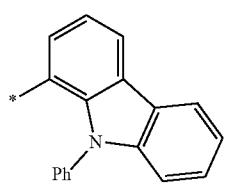 Formula 10-131 | 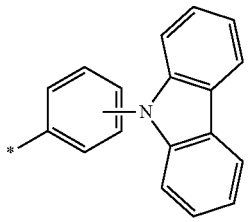 Formula 10-139 |
| 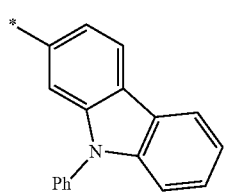 Formula 10-132 | 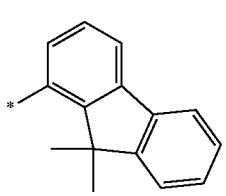 Formula 10-140 |
| 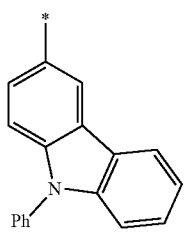 Formula 10-133 | 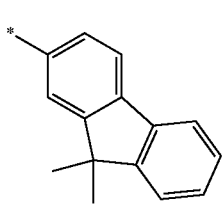 Formula 10-141 |
| 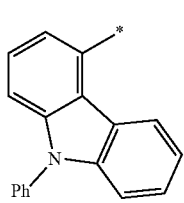 Formula 10-134 | 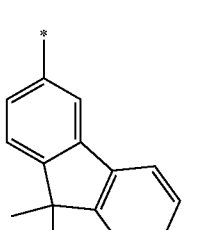 Formula 10-142 |
| 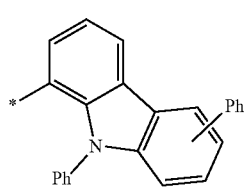 Formula 10-135 | |
| 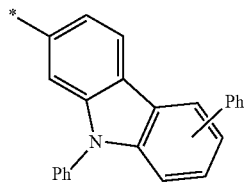 Formula 10-136 | 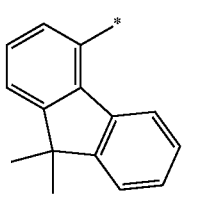 Formula 10-143 | wherein, in Formulae 9-1 to 9-19 and 10-1 to 10-161, "Ph" indicates a phenyl group, "TMS" indicates a trimethylsilyl group, and * indicates a binding site to a neighboring atom.

8. An organometallic compound represented by Formula 1:

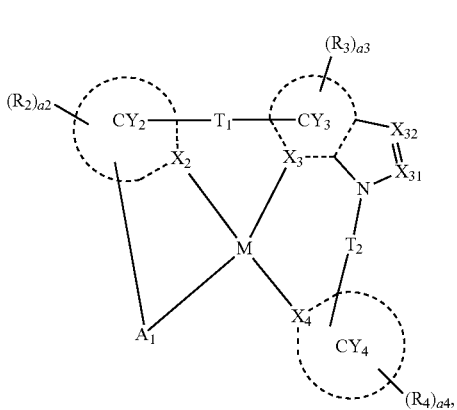

Formula 1 wherein, in Formula 1,
M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au),
two bonds selected from a bond between $A_1$ and M, a bond between $X_2$ and M, a bond between $X_3$ and M, and a bond between $X_4$ and M are each a covalent bond, and the others thereof are each a coordinate bond,
$A_1$ is a first atom linked to M, a non-cyclic moiety comprising the first atom linked to M, or ring $CY_1$ comprising $X_1$ linked to M and substituted with groups $R_1$ in the number of $a_1$,
the first atom is B, N, P, C, Si, O, or S,
rings $CY_1$ to $CY_4$ are each independently selected from a $C_5$-$C_{30}$ carbocyclic group and a $C_1$-$C_{30}$ heterocyclic group,
a cyclometalated ring formed by $A_1$, $CY_2$, and M is a 5-membered ring,
$X_1$ to $X_4$ are each independently N or C, $X_{31}$ is $C(R_{31})$ or N, and $X_{32}$ is $C(R_{32})$, wherein, when $X_{31}$ is $C(R_{31})$, $R_{31}$ and $R_{32}$ are not linked to each other,
$T_1$ and $T_2$ may each independently be selected from a single bond, a double bond, *—$N(R_5)$—*', *—$B(R_5)$—*', *—$P(R_5)$—*', *—$C(R_5)(R_6)$—*', *—$Si(R_5)(R_6)$—*', *—$Ge(R_5)(R_6)$—*', *—S—*', *—Se—*', *—O—*', *—C($=$O)—*', *—S($=$O)—*', *—S($=$O)$_2$—*', *—$C(R_5)=$*', *=$C(R_5)$—*', $C(R_5)=C(R_6)$—*', *—C($=$S)—*', and *—C≡C—*', and * and *' each indicate a binding site to a neighboring atom,
$R_5$ and $R_6$ are optionally linked via a single bond, a double bond, or a first linking group to form a substituted or unsubstituted $C_5$-$C_{30}$ carbocyclic group or a substituted or unsubstituted $C_1$-$C_{30}$ heterocyclic group,
$R_1$ to $R_6$, $R_{31}$, and $R_{32}$ are each independently selected from hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$,
$a_1$ to $a_4$ are each independently an integer from 0 to 20,
two of a plurality of neighboring groups $R_1$ are optionally linked to form a substituted or unsubstituted $C_5$-$C_{30}$ carbocyclic group or a substituted or unsubstituted $C_1$-$C_{30}$ heterocyclic group,
two of a plurality of neighboring groups $R_2$ are optionally linked to form a substituted or unsubstituted $C_5$-$C_{30}$ carbocyclic group or a substituted or unsubstituted $C_1$-$C_{30}$ heterocyclic group,
two of a plurality of neighboring groups $R_3$ are optionally linked to form a substituted or unsubstituted $C_5$-$C_{30}$ carbocyclic group or a substituted or unsubstituted $C_1$-$C_{30}$ heterocyclic group,
two of a plurality of neighboring groups $R_4$ are optionally linked to form a substituted or unsubstituted $C_5$-$C_{30}$ carbocyclic group or a substituted or unsubstituted $C_1$-$C_{30}$ heterocyclic group,
two or more neighboring groups selected from $R_1$ to $R_4$ are optionally linked to form a substituted or unsubstituted $C_5$-$C_{30}$ carbocyclic group or a substituted or unsubstituted $C_1$-$C_{30}$ heterocyclic group,
at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one selected from deuterium, a $C_1$-$C_{60}$ alkyl group, and a $C_6$-$C_{60}$ aryl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from deuterium, a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

9. The organometallic compound of claim 1, wherein $A_1$ is selected from moieties represented by Formulae CY1-1 to CY1-44 and A1-1 to A1-4:

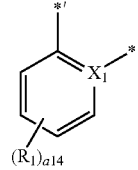

Formula CY1-1

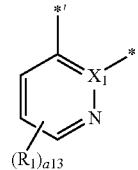

Formula CY1-2

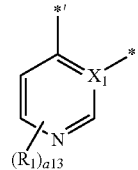

Formula CY1-3

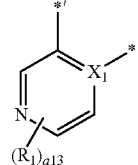

Formula CY1-4

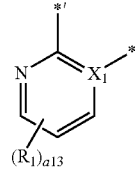

Formula CY1-5

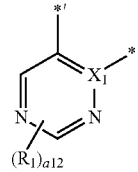

Formula CY1-6

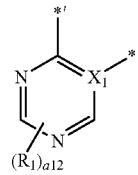

Formula CY1-7

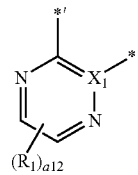

Formula CY1-8

-continued
Formula CY1-9
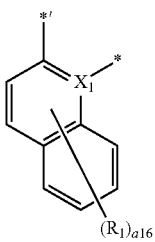
Formula CY1-10
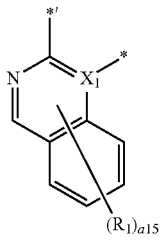
Formula CY1-11
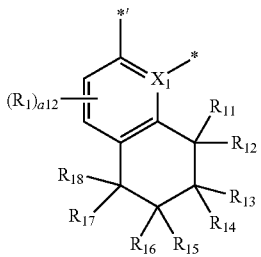
Formula CY1-12
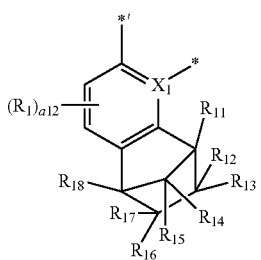
Formula CY1-13
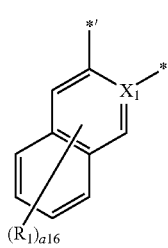
Formula CY1-14
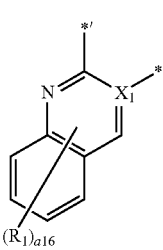
Formula CY1-15
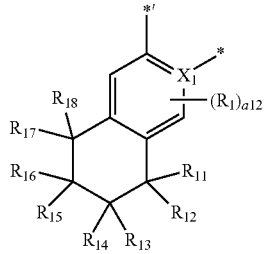
Formula CY1-16
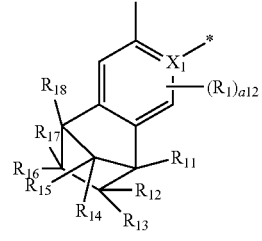
Formula CY1-17
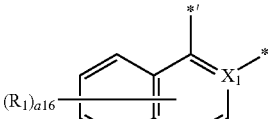
Formula CY1-18
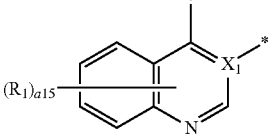
Formula CY1-19
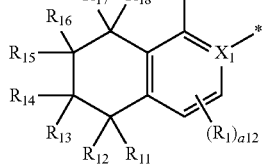
Formula CY1-20
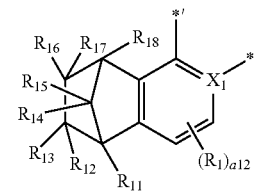
Formula CY1-21
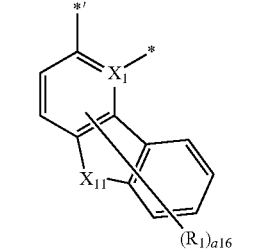

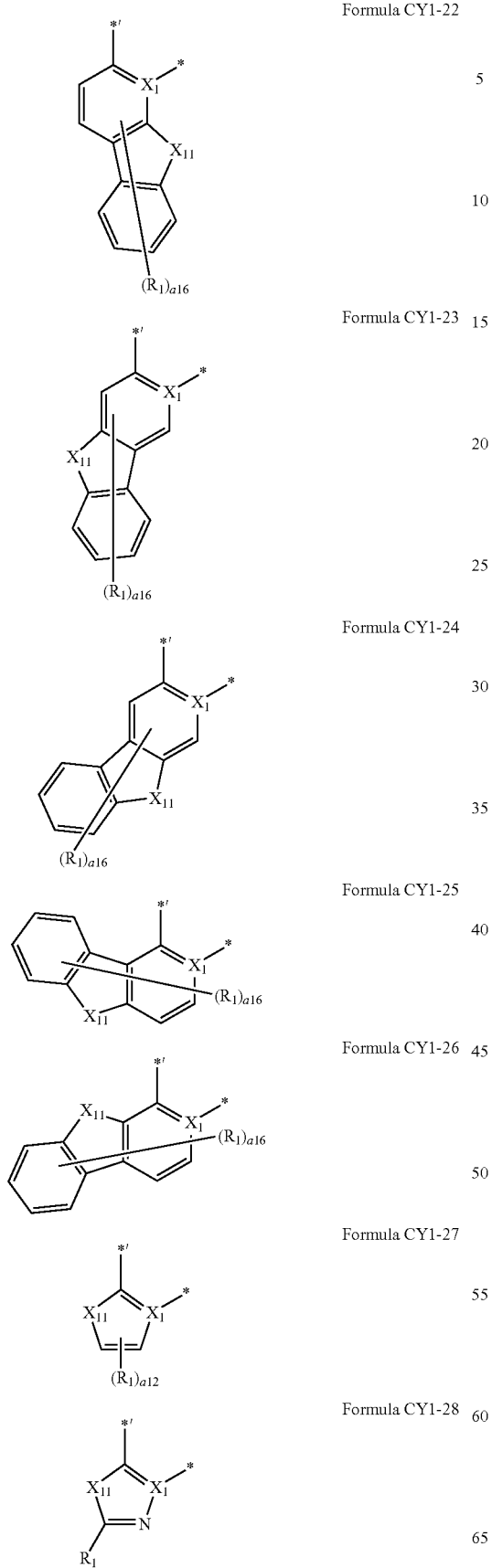
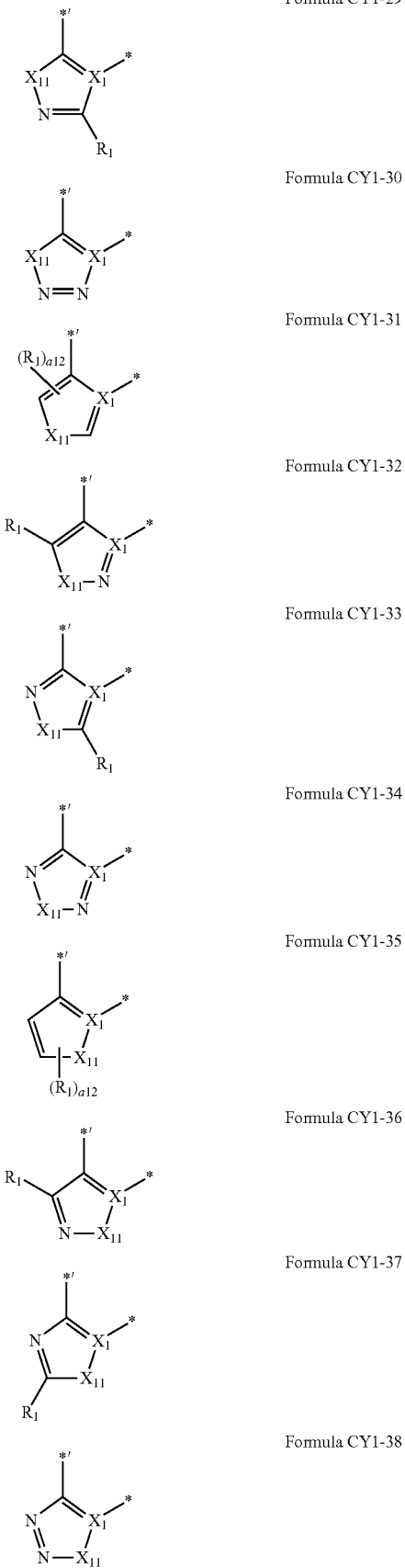

-continued

Formula CY1-39
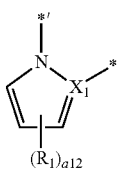

Formula CY1-40
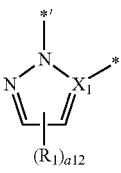

Formula CY1-41
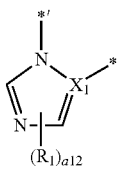

Formula CY1-42
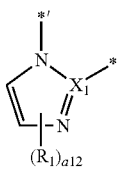

Formula CY1-43
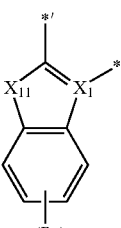

Formula CY1-44
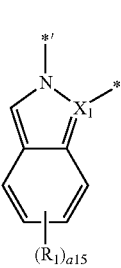

Formula A1-1
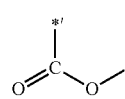

Formula A1-2
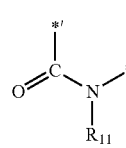

Formula A1-3
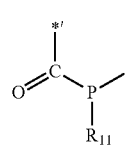

Formula A1-4
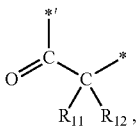

wherein, in Formulae CY1-1 to CY1-44 and A1-1 to A1-4, $X_1$ and $R_1$ are the same as described in claim 1, $X_{11}$ is O, S, $C(R_{11})(R_{12})$, or $Si(R_{11})(R_{12})$, $R_{11}$ to $R_{18}$ are the same as described in connection with $R_1$ in claim 1, a16 is an integer from 0 to 6, a15 is an integer from 0 to 5, a14 is an integer from 0 to 4, a13 is an integer from 0 to 3, a12 is an integer from 0 to 2,

* indicates a binding site to M in Formula 1, and

*' indicates a binding site to ring $CY_2$ in Formula 1.

10. The organometallic compound of claim 1, wherein a moiety represented by

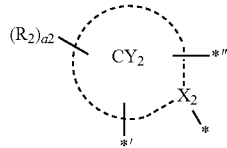

in Formula 1 is represented by one of Formulae CY2-1 to CY2-45:

Formula CY2-1
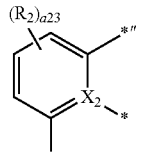

Formula CY2-2
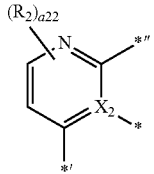

Formula CY2-3
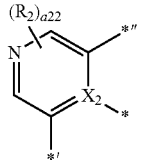

Formula CY2-4
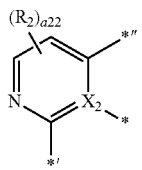

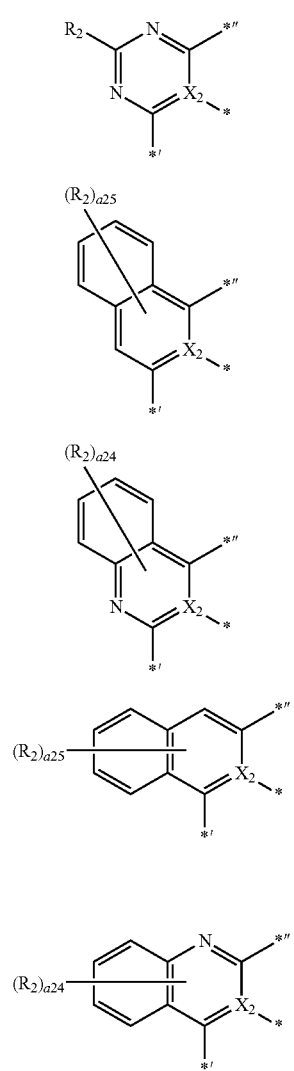
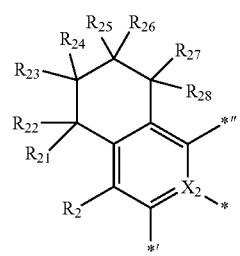
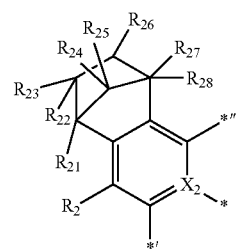
Formula CY2-5
Formula CY2-6
Formula CY2-7
Formula CY2-8
Formula CY2-9
Formula CY2-10
Formula CY2-11
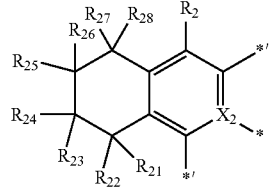
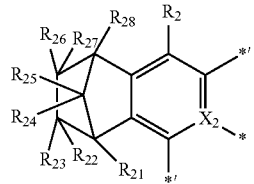
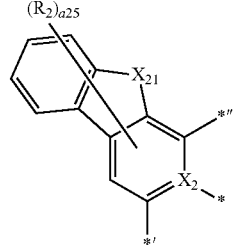
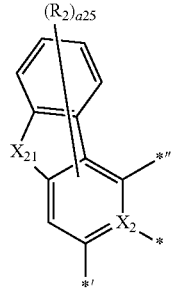
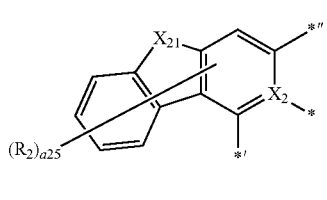
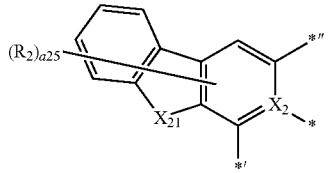
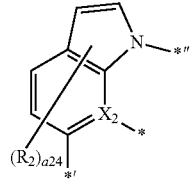
Formula CY2-12
Formula CY2-13
Formula CY2-14
Formula CY2-15
Formula CY2-16
Formula CY2-17
Formula CY2-18

-continued
Formula CY2-19
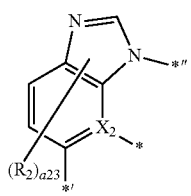
Formula CY2-20
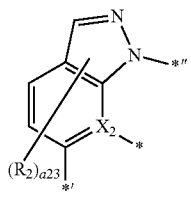
Formula CY2-21
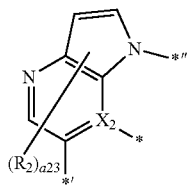
Formual CY2-22
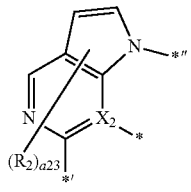
Formula CY2-23
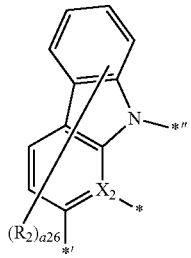
Formula CY2-24
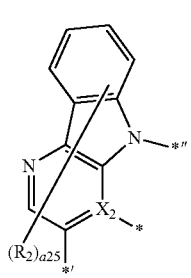
Formula CY2-25
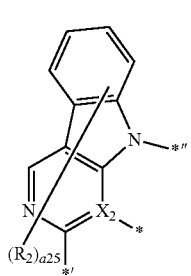
-continued
Formula CY2-26
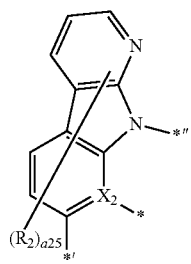
Formula CY2-27
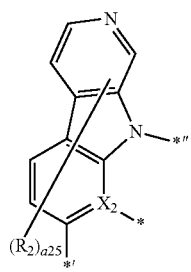
Formula CY2-28
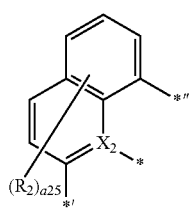
Formula CY2-29
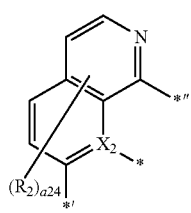
Formula CY2-30
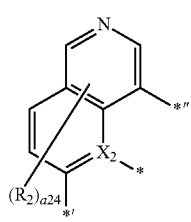
Formula CY2-31
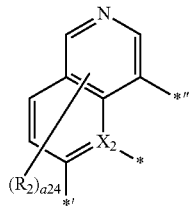
Formula CY2-32
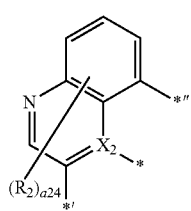

Formula CY2-33
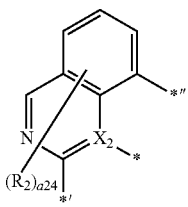

Formula CY2-34
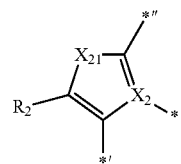

Formula CY2-35
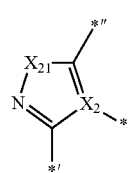

Formula CY2-36
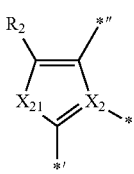

Formula CY2-37
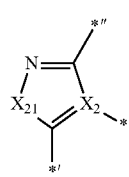

Formula CY2-38
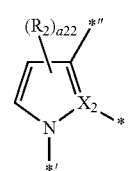

Formula CY2-39
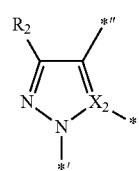

Formula CY2-40
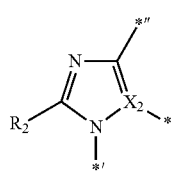

Formula CY2-41
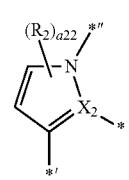

Formula CY2-42
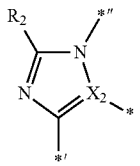

Formula CY2-43
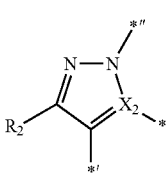

Formula CY2-44
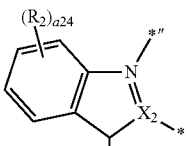

Formula CY2-45
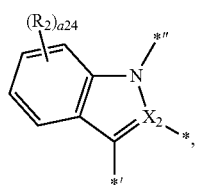

wherein, in Formulae CY2-1 to CY2-45, $X_2$ and $R_2$ are the same as described in claim 1, $X_{21}$ is O, S, $N(R_{21})$, $C(R_{21})(R_{22})$, or $Si(R_{21})(R_{22})$, $R_{21}$ to $R_{28}$ are the same as described in connection with $R_2$ in claim 1, a26 is an integer from 0 to 6, a25 is an integer from 0 to 5, a24 is an integer from 0 to 4, a23 is an integer from 0 to 3, a22 is an integer from 0 to 2, \* indicates a binding site to M in Formula 1, \*' indicates a binding site to $A_1$ in Formula 1, and \*" indicates a binding site to $T_1$ in Formula 1.

11. The organometallic compound of claim 1, wherein a moiety represented by

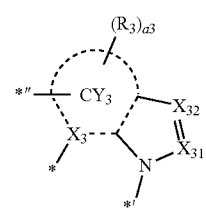

in Formula 1 is represented by one of Formulae CY3-1 to CY3-10:

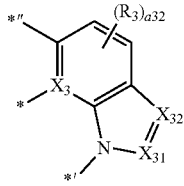

Formula CY3-1

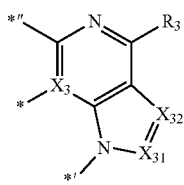

Formula CY3-2

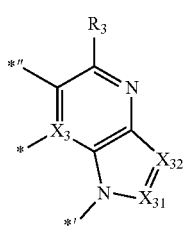

Formula CY3-3

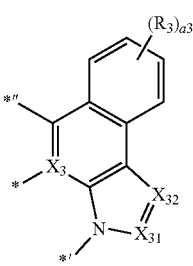

Formula CY3-4

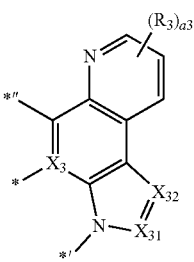

Formula CY3-5

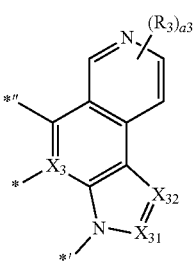

Formula CY3-6

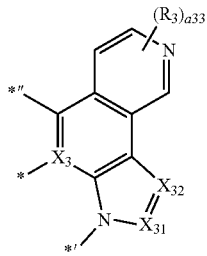

Formula CY3-7

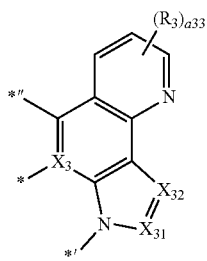

Formula CY3-8

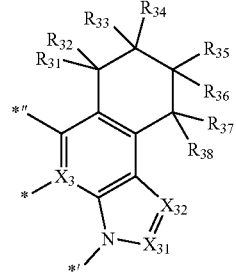

Formula CY3-9

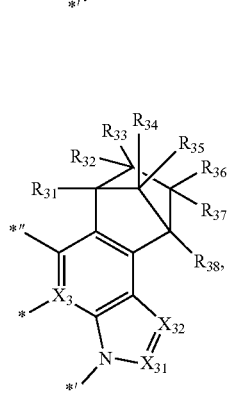

Formula CY3-10 wherein, in Formulae CY3-1 to CY3-10, $X_3$, $R_3$, $X_{31}$, and $X_{32}$ are the same as described in claim 1, $R_{31}$ to $R_{38}$ are the same as described in connection with $R_3$ in claim 1, a34 is an integer from 0 to 4, a33 is an integer from 0 to 3, a32 is an integer from 0 to 2, \* indicates a binding site to M in Formula 1, \*" indicates a binding site to $T_1$ in Formula 1, and \*' indicates a binding site to $T_2$ in Formula 1.

12. The organometallic compound of claim 1, wherein a moiety represented in
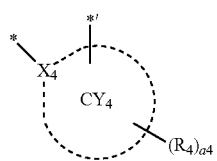
in Formula 1 is represented by one of Formulae CY4-1 to CY4-44:
Formula CY4-1
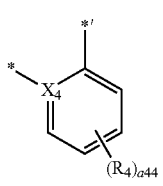
Formula CY4-2
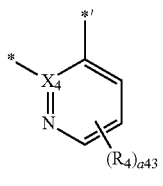
Formula CY4-3
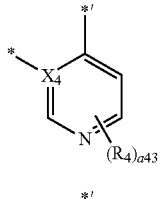
Formula CY4-4
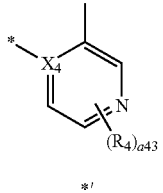
Formula CY4-5
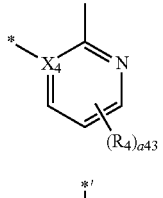
Formula CY4-6
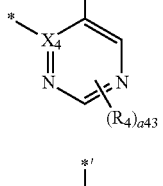
Formula CY4-7
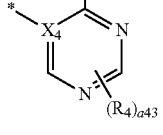
Formula CY4-8
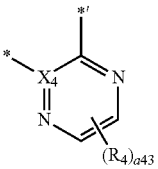
Formula CY4-9
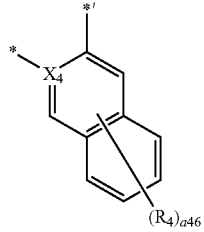
Formula CY4-10
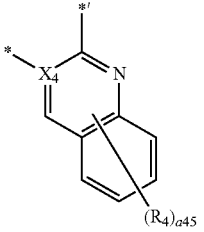
Formula CY4-11
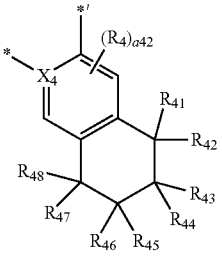
Formula CY4-12
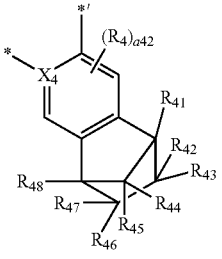
Formula CY4-13
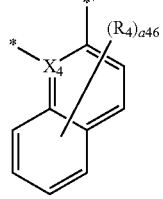
Formula CY4-14
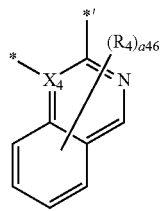

Formula CY4-15
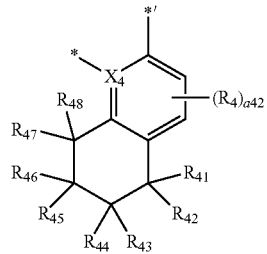
Formula CY4-16
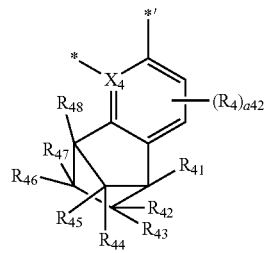
Formula CY4-17
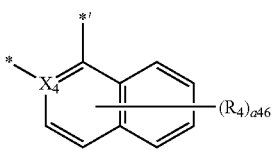
Formula CY4-18
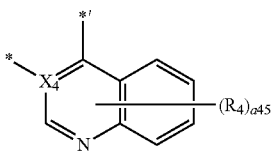
Formula CY4-19
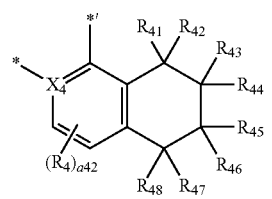
Formula CY4-20
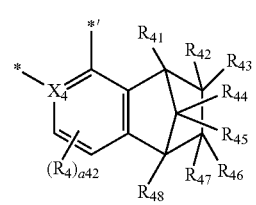
Formula CY4-21
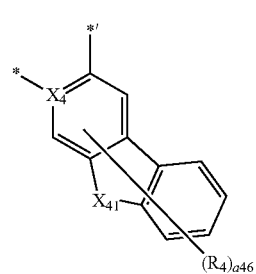
Formula CY4-22
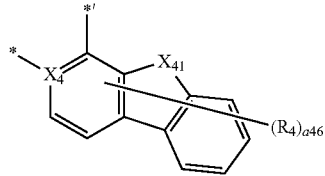
Formula CY4-23
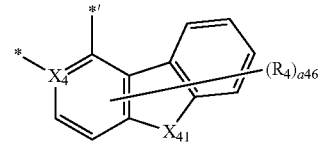
Formula CY4-24
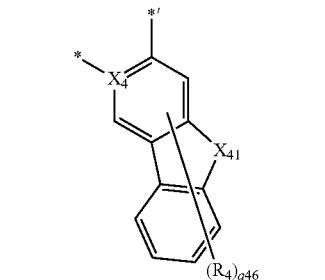
Formula CY4-25
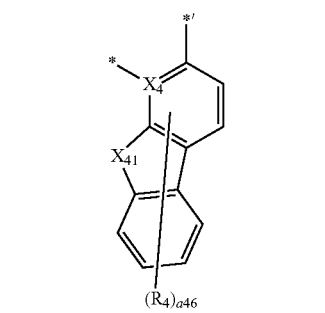
Formula CY4-26
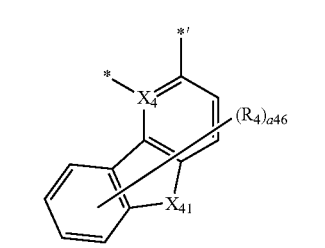
Formula CY4-27
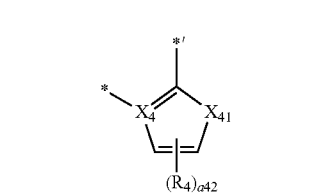
Formula CY4-28
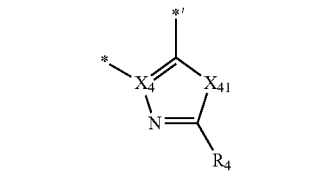

Formula CY4-29
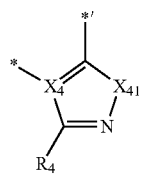

Formula CY4-30
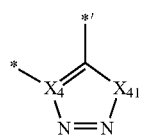

Formula CY4-31
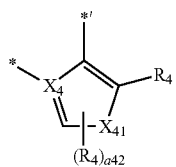

Formula CY4-32
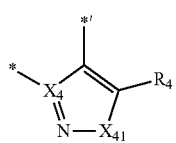

Formula CY4-33
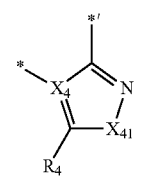

Formula CY4-34
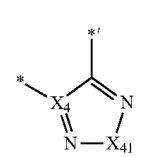

Formula CY4-35
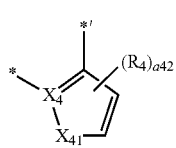

Formula CY4-36
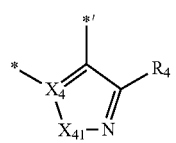

Formula CY4-37
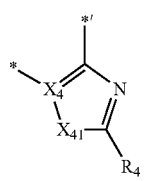

Formula CY4-38
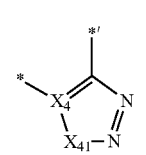

Formula CY4-39
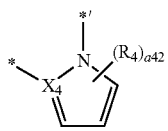

Formula CY4-40
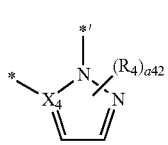

Formula CY4-41
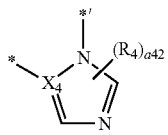

Formula CY4-42
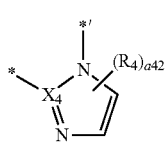

Formula CY4-43
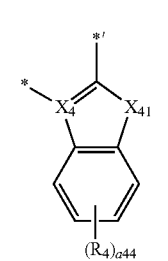

Formula CY4-44
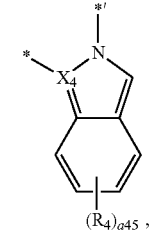

wherein, in Formulae CY4-1 to CY4-44, $X_4$ and $R_4$ are the same as described in claim 1, $X_{41}$ is O, S, N($R_{41}$), C($R_{41}$)($R_{42}$), or Si($R_{41}$)($R_{42}$), $R_{41}$ to $R_{48}$ are the same as described in connection with $R_4$ in claim 1, $a_{46}$ is an integer from 0 to 6, $a_{45}$ is an integer from 0 to 5, $a_{44}$ is an integer from 0 to 4, $a_{43}$ is an integer from 0 to 3, $a_{42}$ is an integer from 0 to 2, \* indicates a binding site to M in Formula 1, and \*' indicates a binding site to $T_2$ in Formula 1.

13. The organometallic compound of claim 1, wherein $A_1$ is selected from moieties represented by Formulae CY1(1) to CY1(19), a moiety represented by

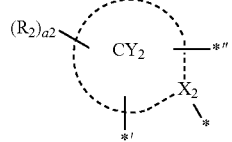

is represented by one of Formulae CY2(1) to CY2(13), a moiety represented by

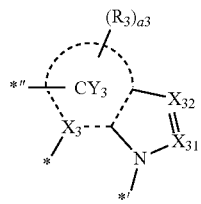

is represented by one of Formulae CY3(1) to CY3(18), and a moiety represented by

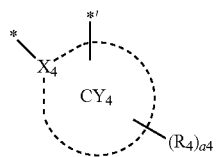

is represented by one of Formulae CY4(1) to CY4(11):

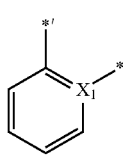

Formula CY1(1)

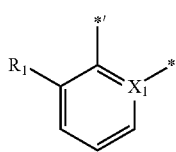

Formula CY1(2)

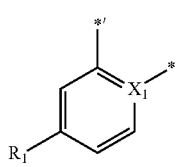

Formula CY1(3)

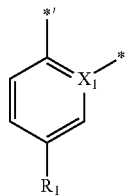

Formula CY1(4)

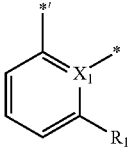

Formula CY1(5)

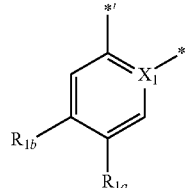

Formula CY1(6)

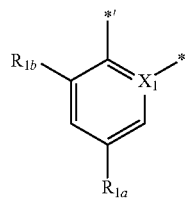

Formula CY1(7)

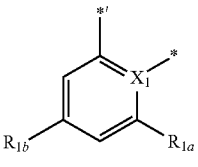

Formula CY1(8)

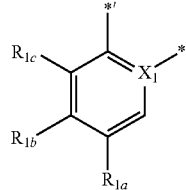

Formula CY1(9)

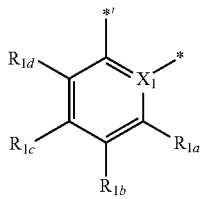

Formula CY1(10)

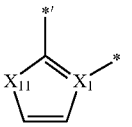

Formula CY1(11)

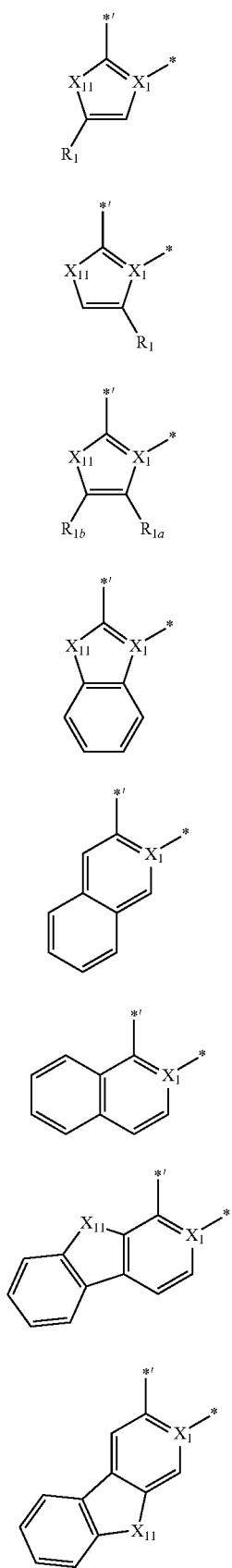

Formula CY2(9)

Formula CY2(10)

Formula CY2(11)

Formula CY2(12)

Formula CY2(13)

Formula CY3(1)

Formula CY3(2)

Formula CY3(3)

Formula CY3(3)

Formula CY3(4)

Formula CY3(5)

Formula CY3(6)

Formula CY3(7)

Formula CY3(8)

Formula CY3(9)

Formula CY3(10)

-continued
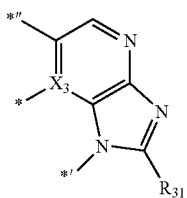
Formula CY3(12)
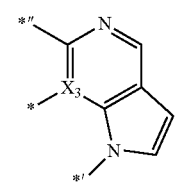
Formula CY3(13)
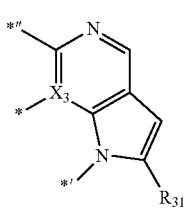
Formula CY3(14)
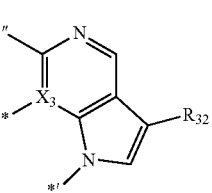
Formula CY3(15)
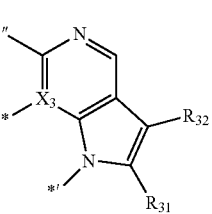
Formula CY3(16)
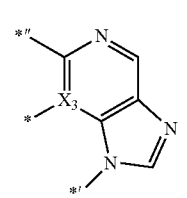
Formula CY3(17)
-continued
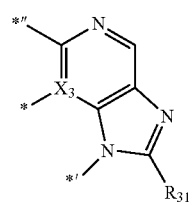
Formula CY3(18)
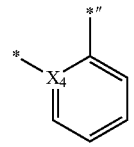
Formula CY4(1)
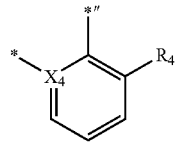
Formula CY4(2)
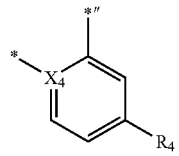
Formula CY4(3)
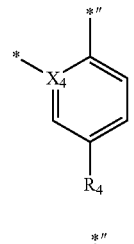
Formula CY4(4)
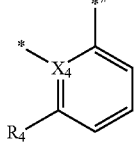
Formula CY4(5)
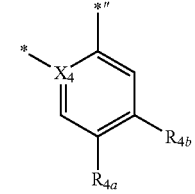
Formula CY4(6)
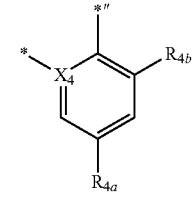
Formula CY4(7)

211

-continued

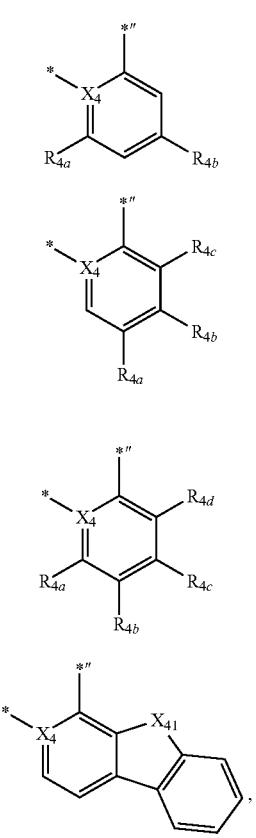

Formula CY4(8)

Formula CY4(9)

Formula CY4(10)

Formula CY4(11)

wherein, in Formulae CY1(1) to CY1(19), CY2(1) to CY2(13), CY3(1) to CY3(18), and CY4(1) to CY4(11), $X_1$ to $X_4$, $R_1$ to $R_4$, $R_{31}$, and $R_{32}$ are the same as described in claim 1, $X_{11}$ is O, S, N($R_{11}$), C($R_{11}$)($R_{12}$), or Si($R_{11}$)($R_{12}$), $X_{21}$ is O, S, N($R_{21}$), C($R_{21}$)($R_{22}$), or Si($R_{21}$)($R_{22}$), $X_{41}$ is O, S, N($R_{41}$), C($R_{41}$)($R_{42}$), or Si($R_{41}$)($R_{42}$), $R_{1a}$ to $R_{1d}$, $R_{11}$, and $R_{12}$ are the same as described in connection with $R_1$ in claim 1, $R_{2a}$, $R_{2b}$, $R_{21}$, and $R_{22}$ are the same as described in connection with $R_2$ in claim 1, $R_{4a}$ to $R_{4d}$, $R_{41}$, and $R_{42}$ are the same as described in connection with $R_4$ in claim 1, \* in Formulae CY1(1) to CY1(19), CY2(1) to CY2(13), CY3(1) to CY3(18), and CY4(1) to CY4(11) indicates a binding site to M in Formula 1, \*' in Formulae CY1(1) to CY1(19) indicates a binding site to ring CY2 in Formula 1, \*' in Formulae CY2(1) to CY2(13) indicates a binding site to $A_1$ in Formula 1, \*''' in Formulae CY2(1) to CY2(13) indicates a binding site to $T_1$ in Formula 1, \*''' in Formulae CY3(1) to CY3(18) indicates a binding site to $T_1$ in Formula 1, \*' in Formulae CY3(1) to CY3(18) indicates a binding site to $T_2$ in Formula 1, and \*' in Formulae CY4(1) to CY4(11) indicates a binding site to $T_2$ in Formula 1.

212

14. The organometallic compound of claim 1, wherein the organometallic compound is represented by Formula 1-1:

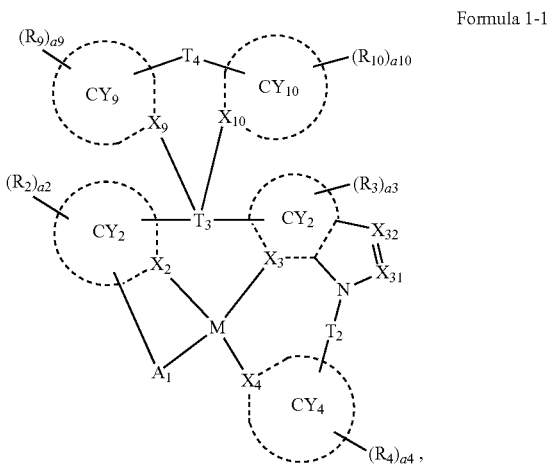

Formula 1-1 wherein, in Formula 1-1,

M, $A_1$, $X_2$ to $X_4$, $CY_2$ to $CY_4$, $X_{31}$, $X_{32}$, $T_2$, $R_2$ to $R_4$, and $a_2$ to $a_4$ are the same as described in claim 1, $X_9$ and $X_{10}$ are each independently C or N, $CY_9$ and $CY_{10}$ are each independently selected from a $C_5$-$C_{30}$ carbocyclic group and a $C_1$-$C_{30}$ heterocyclic group, $R_9$ and $R_{10}$ are the same as described in connection with $R_1$ in claim 1, $a_9$ and $a_{10}$ are the same as described in connection with a1 in claim 1, $T_3$ is C, Si, or Ge, $T_4$ may be selected from a single bond, a double bond, \*—N($R_7$)—\*', \*—B($R_7$)—\*', \*—P($R_7$)—\*', \*—C($R_7$)($R_8$)—\*', \*—Si($R_7$)($R_8$)—\*', \*—Ge($R_7$)($R_8$)—\*', \*—S—\*', \*—Se—\*', \*—O—\*', \*—C(=O)—\*', \*—S(=O)—\*', \*—S(=O)$_2$—\*', \*—C($R_7$)=\*', \*=C($R_7$)—\*', \*—C($R_7$)=C($R_8$)—\*', \*—C(=S)—\*', and \*—C≡C—\*', $R_7$ and $R_8$ are the same as described in connection with $R_5$ in claim 1, and \* and \*¹ each indicate a binding site to a neighboring atom.

15. The organometallic compound of claim 1, wherein the organometallic compound is one of Compounds 1 to 105 below:

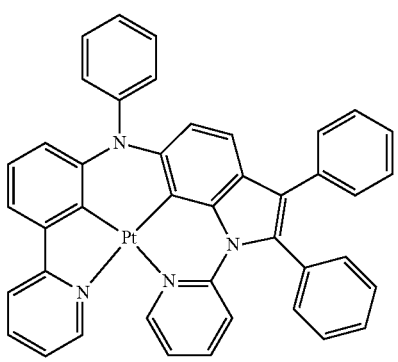

1

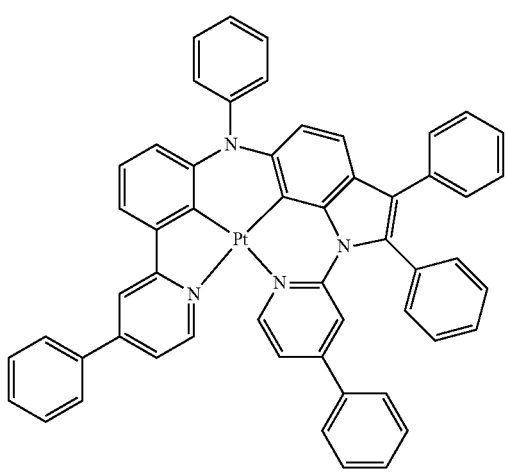
2
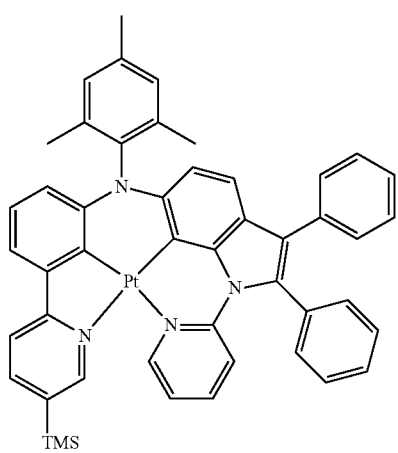
5
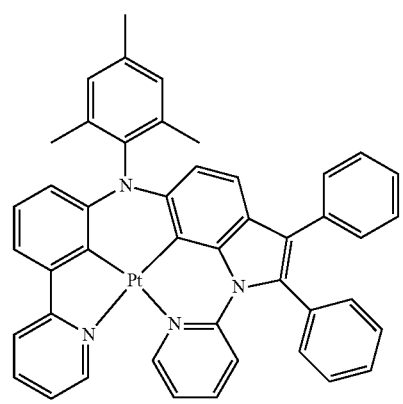
3
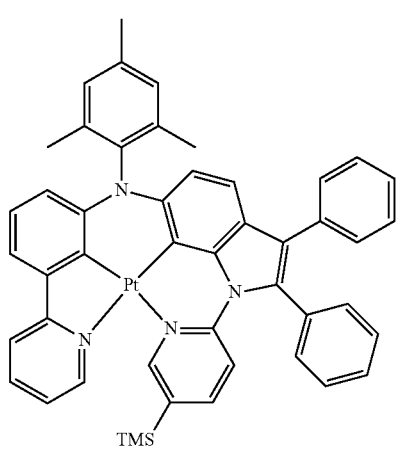
6
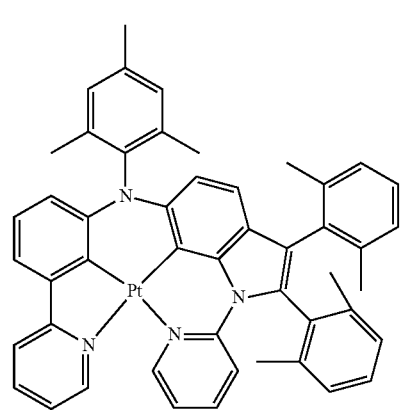
4
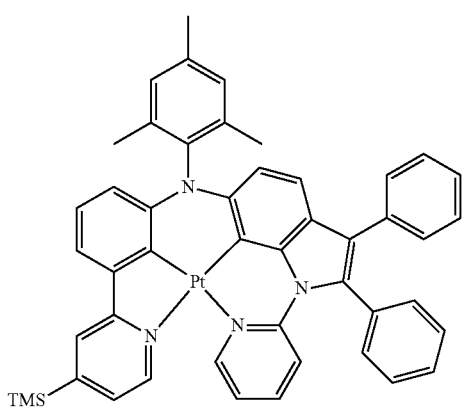
7

8
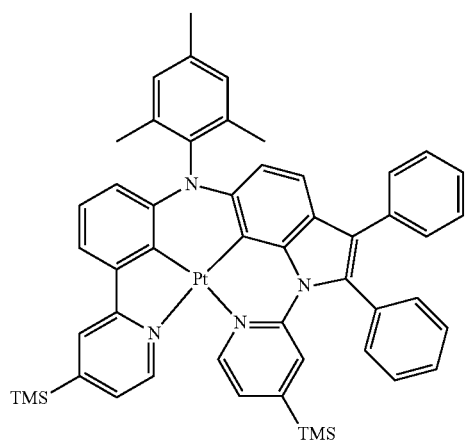
9
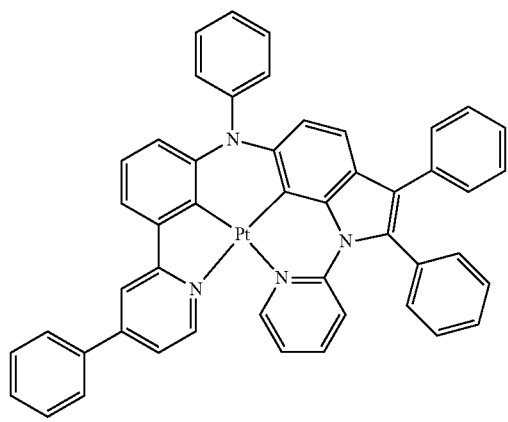
10
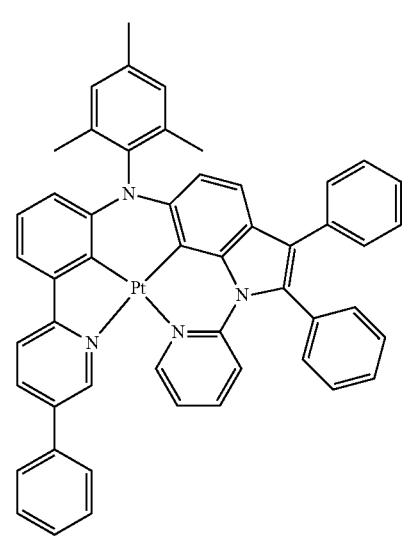
11
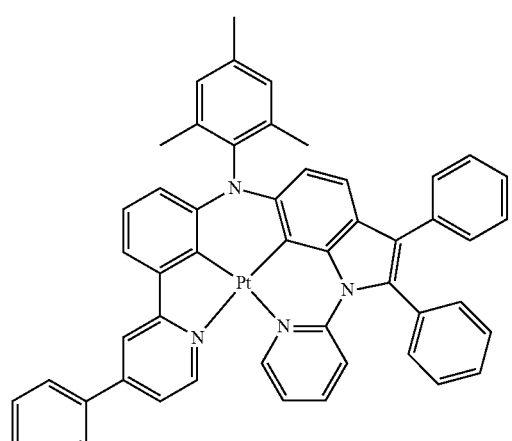
12
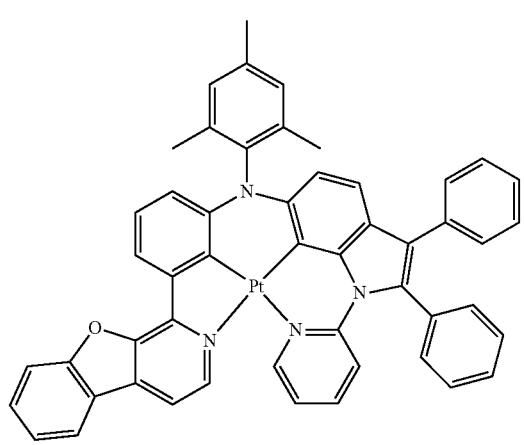
13
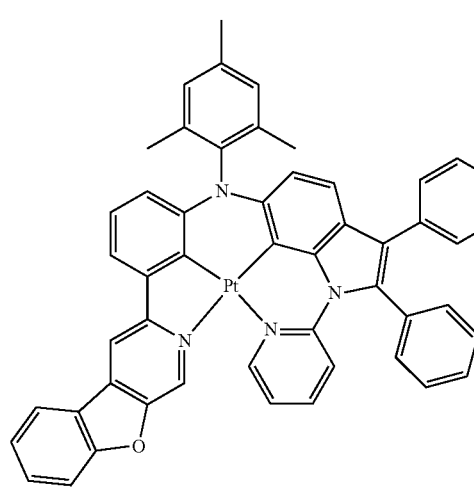

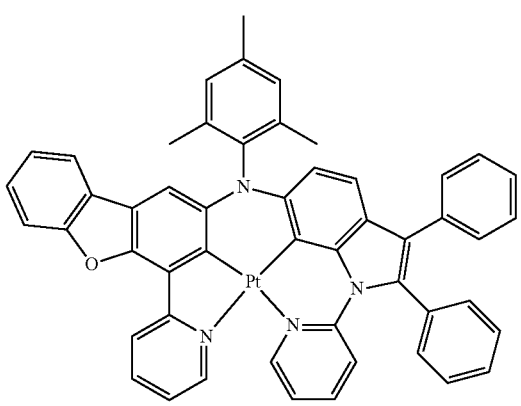
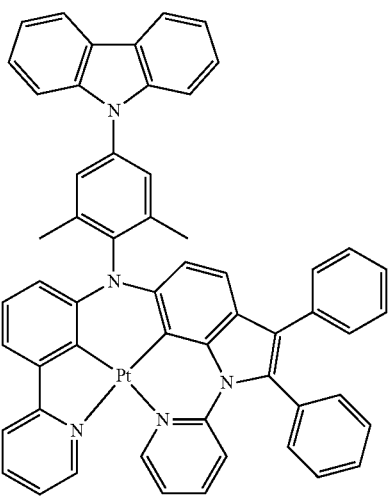
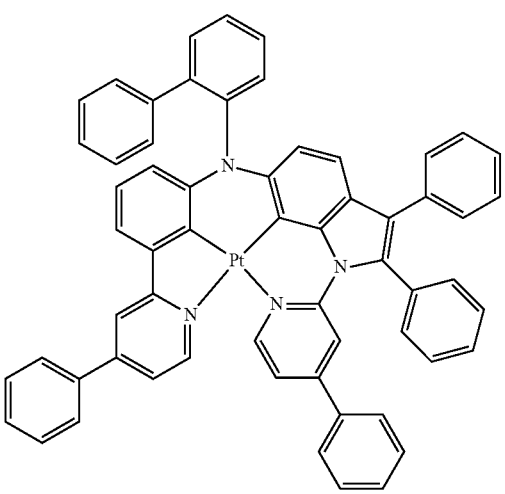
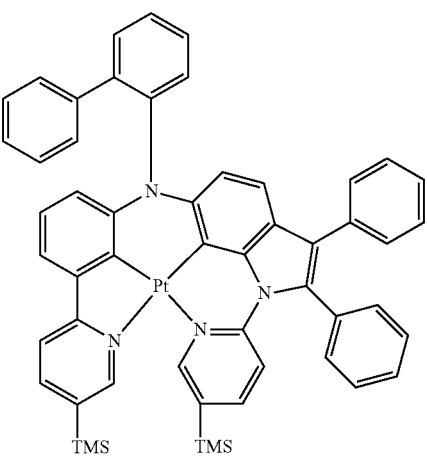

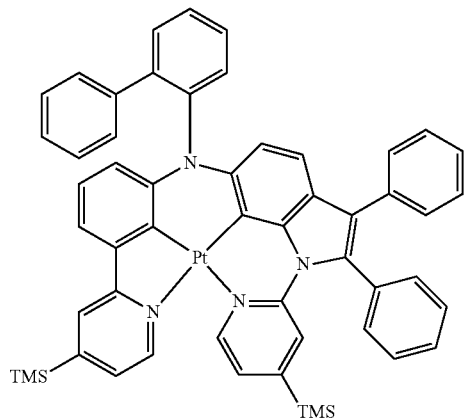
21
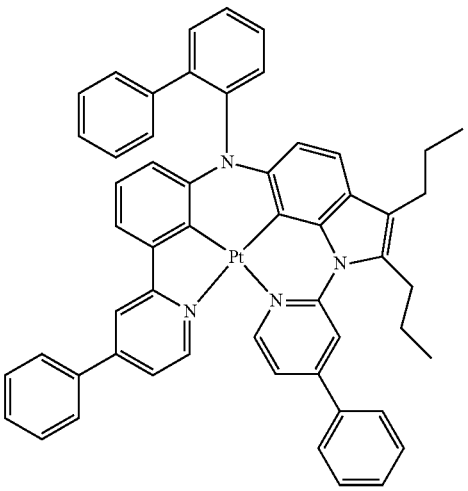
24
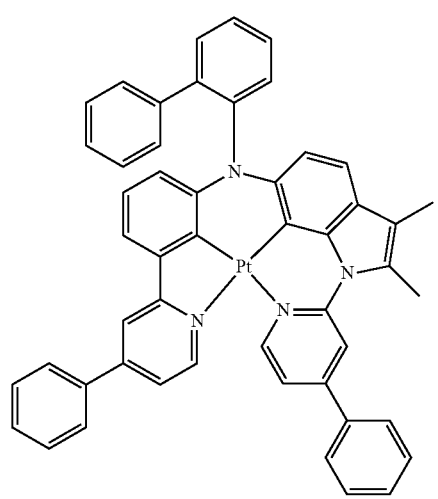
22
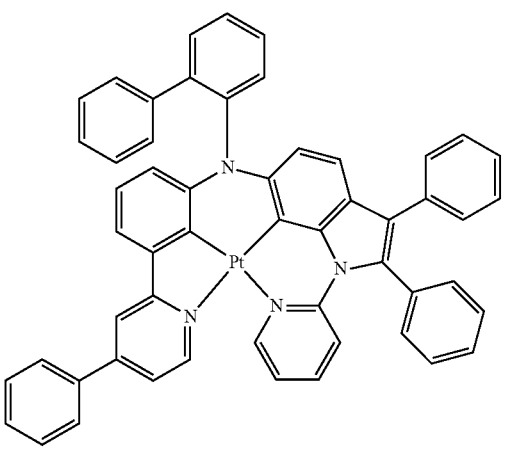
25
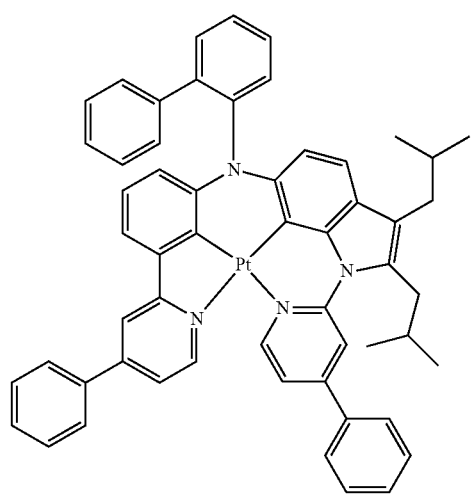
23
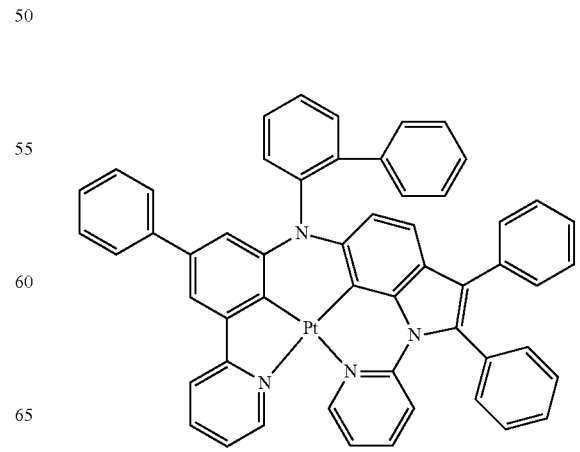
26

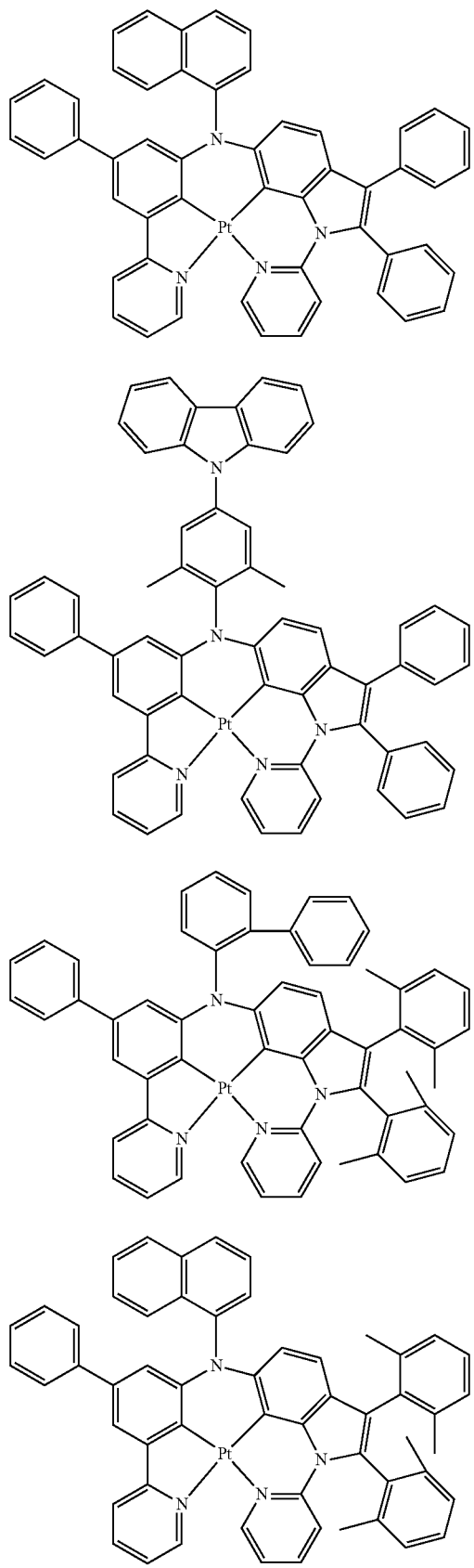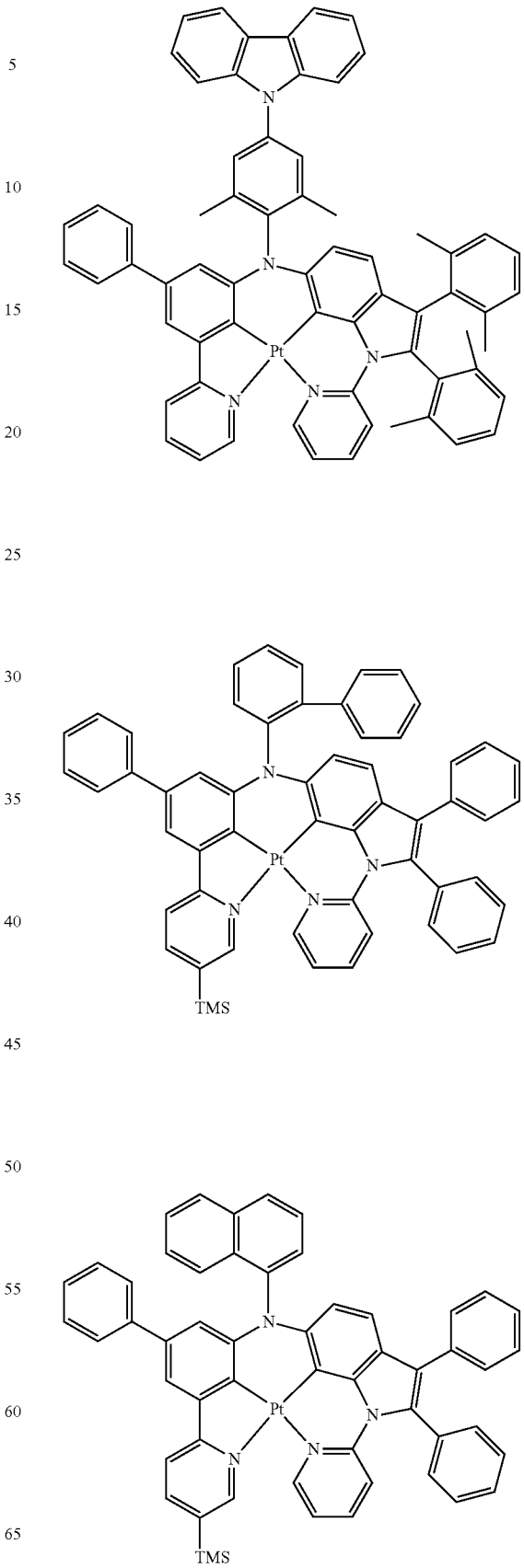

34
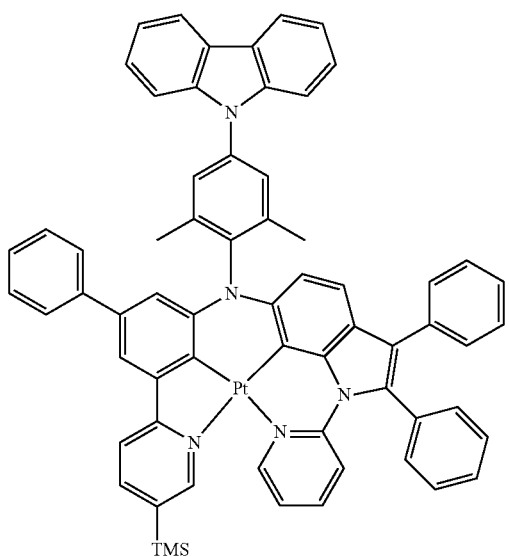
35
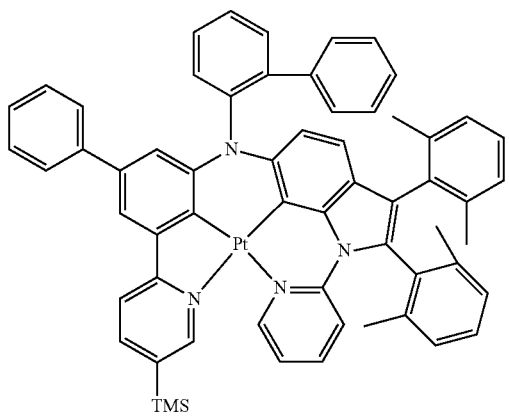
36
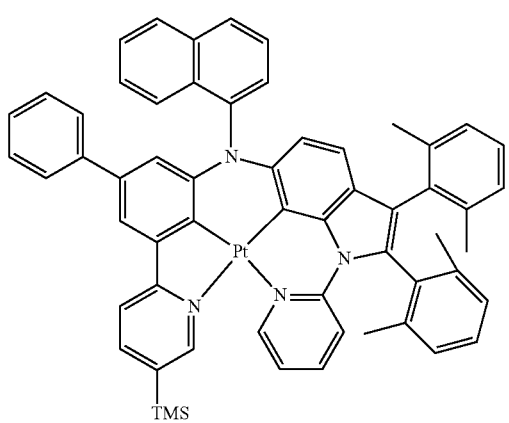
37
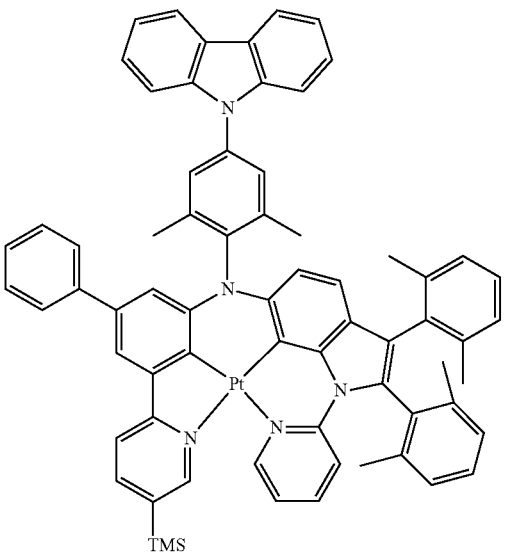
38
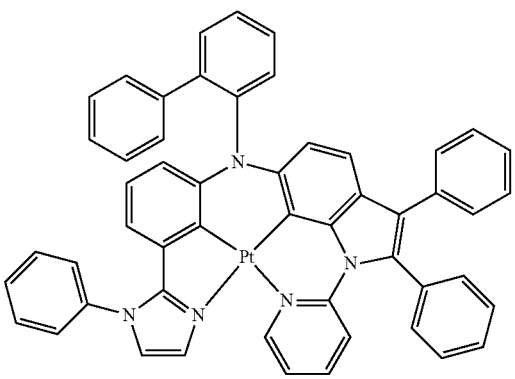
39
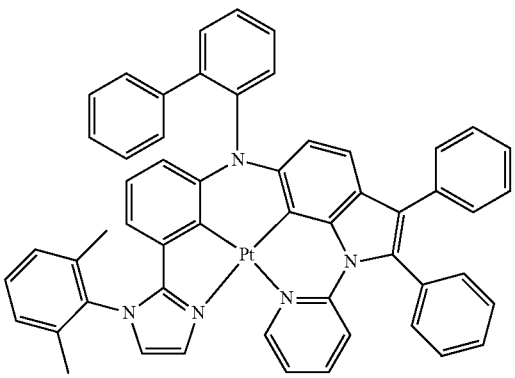

225
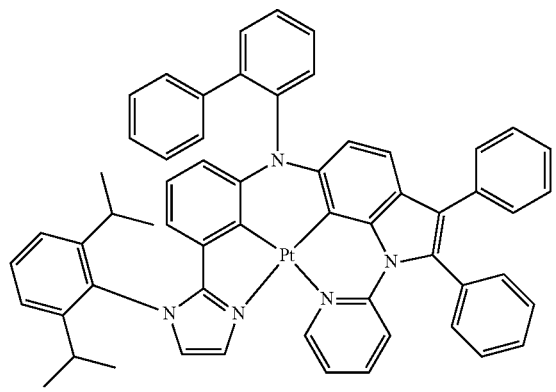
40
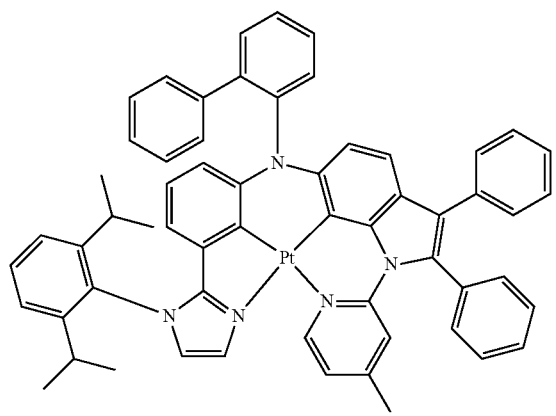
41
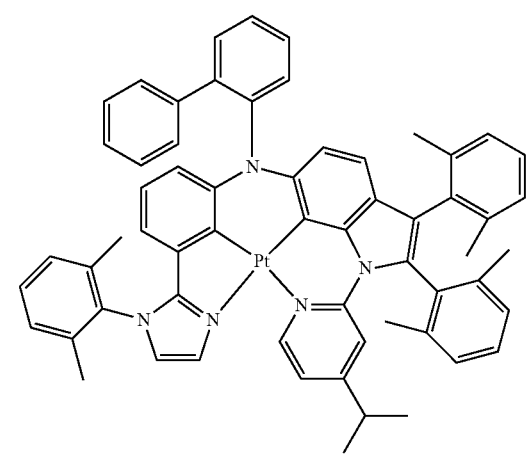
42
226
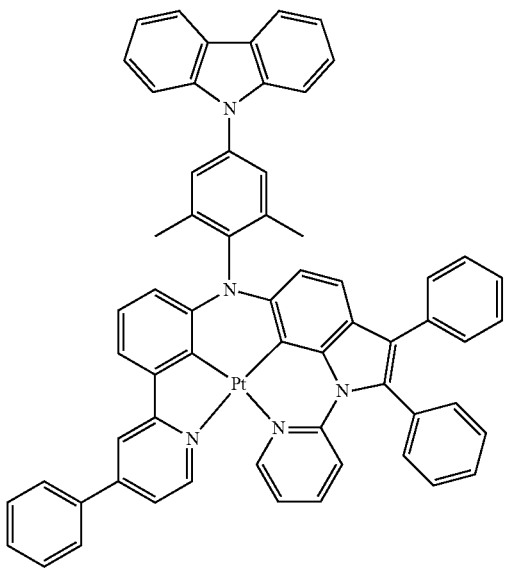
43
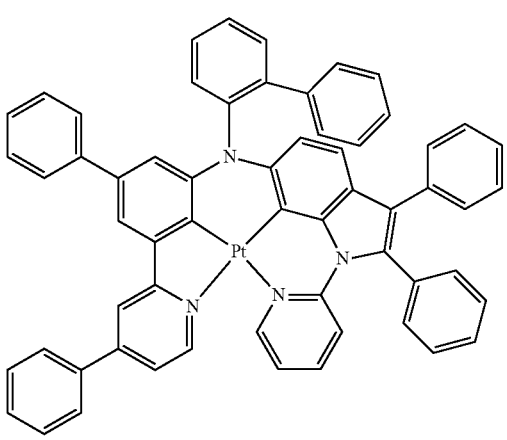
44
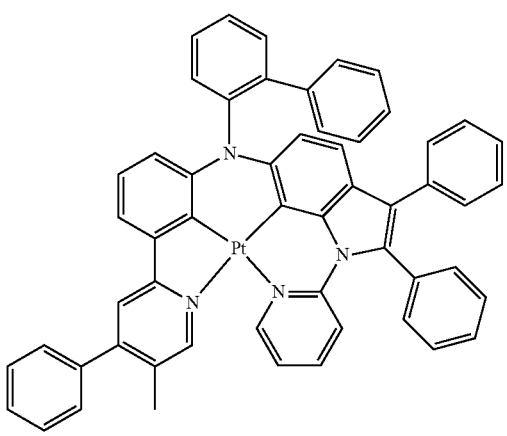
45

227
-continued
46
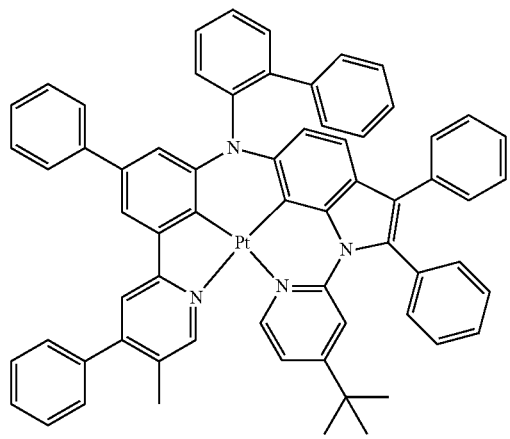
48
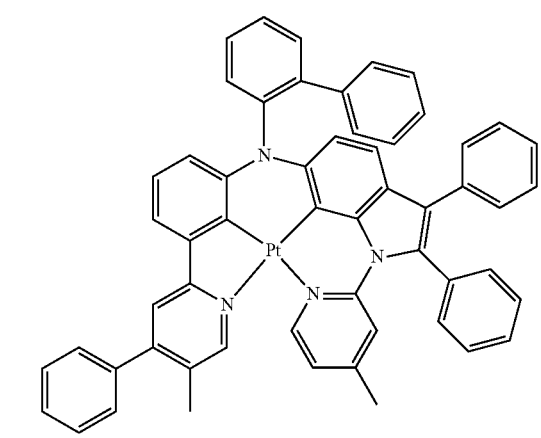
228
-continued
49
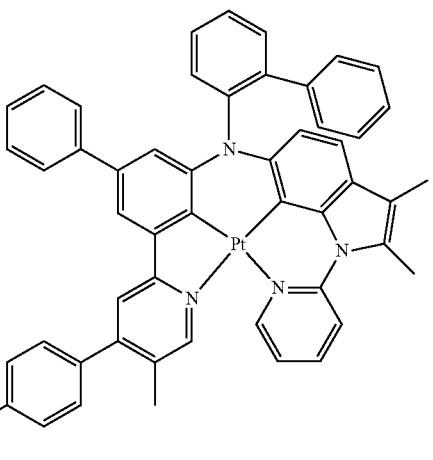
50
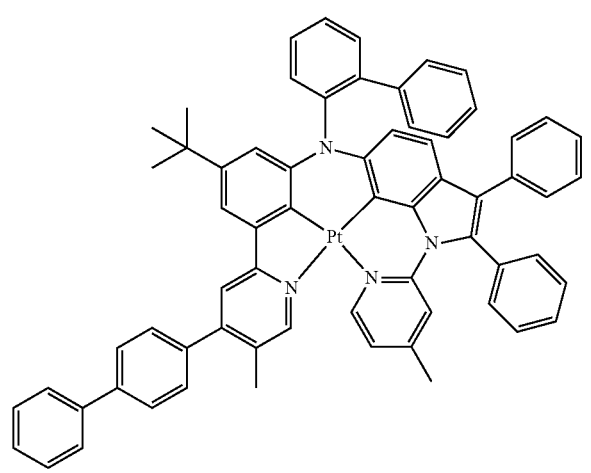
51
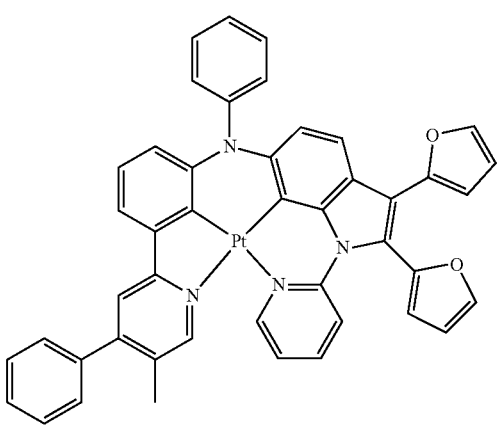

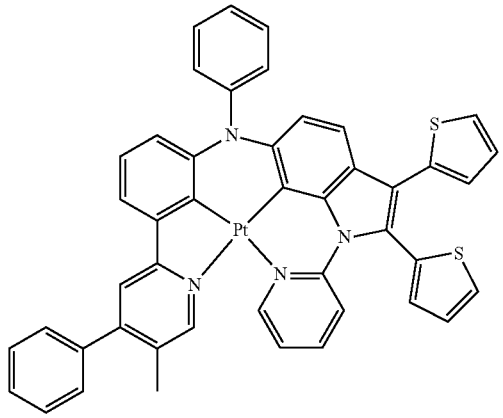
52
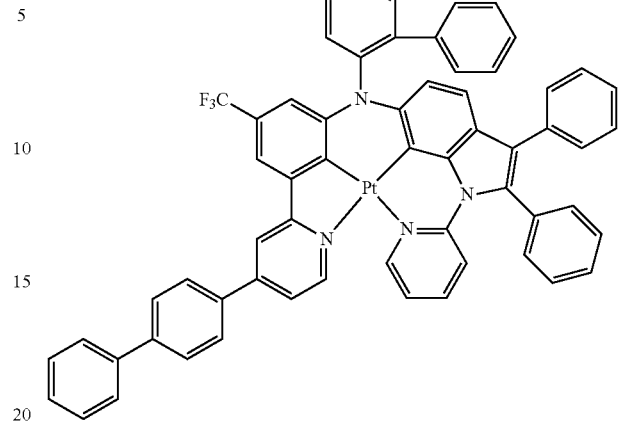
55
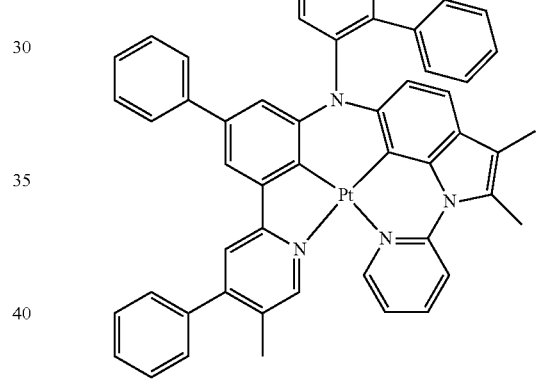
53
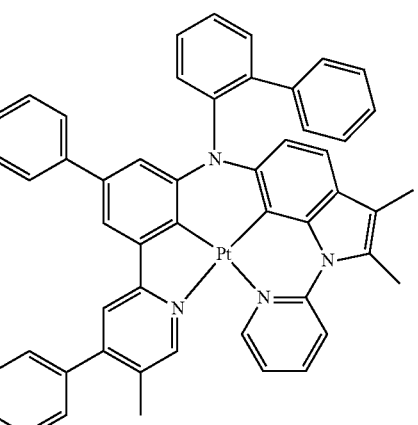
56
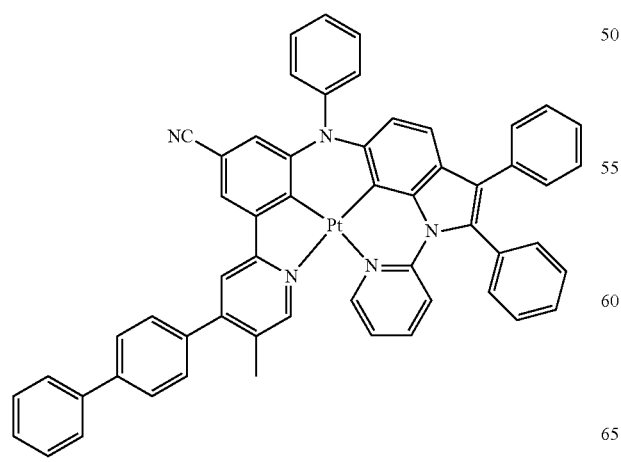
54
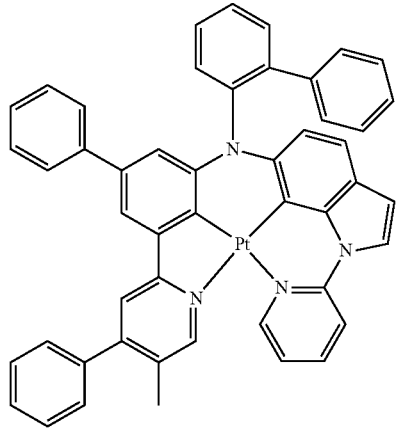
57

-continued
58
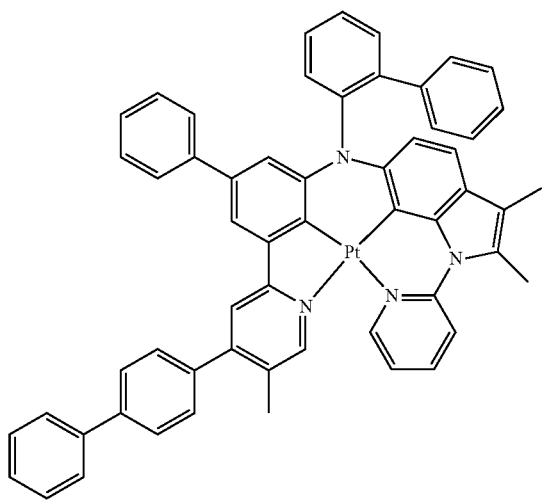
59
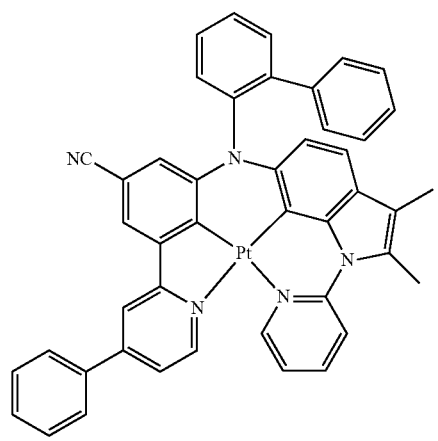
60
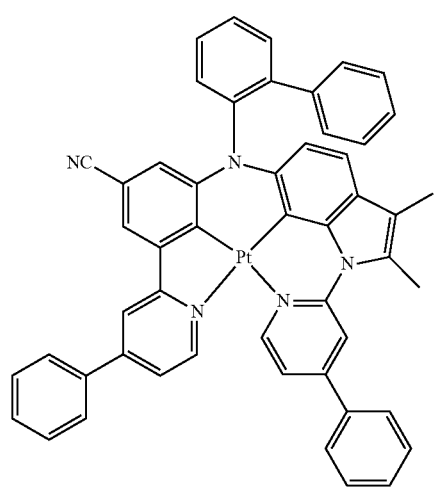
-continued
61
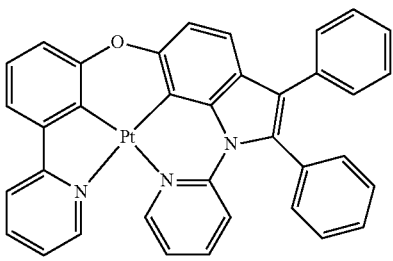
62
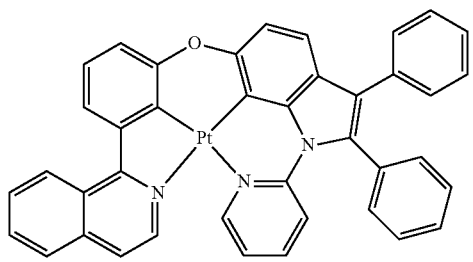
63
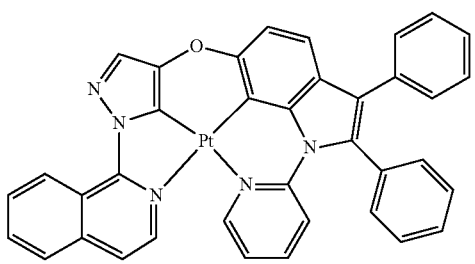
64
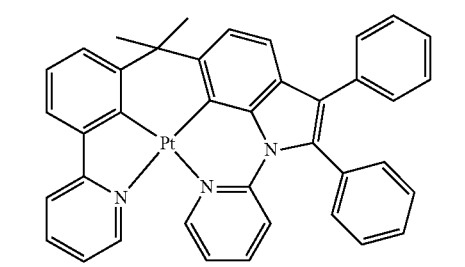
65
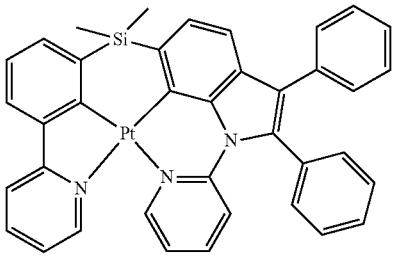
66
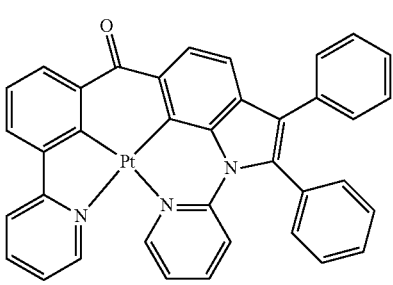

-continued
67
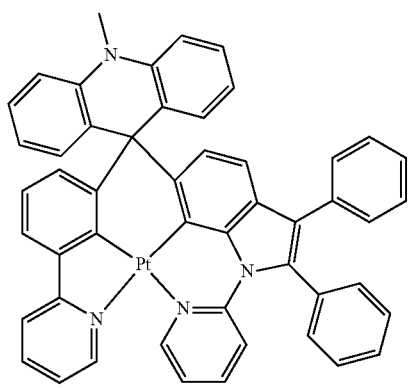
68
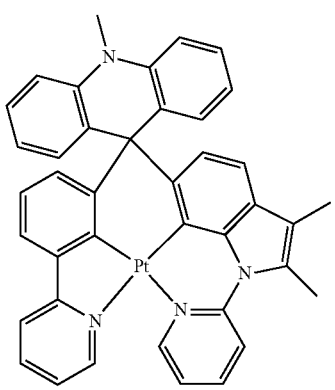
69
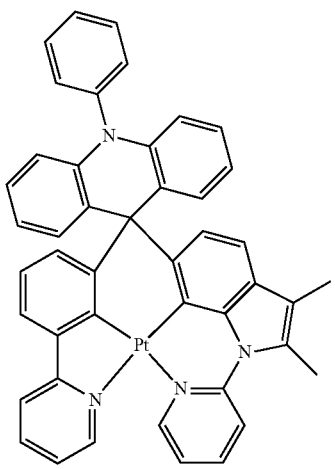
70
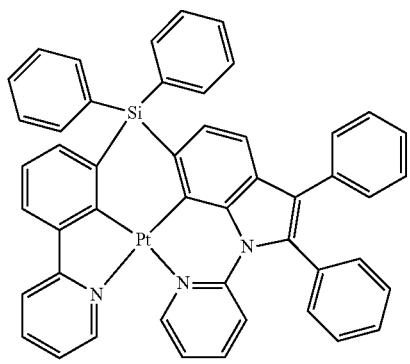
-continued
71
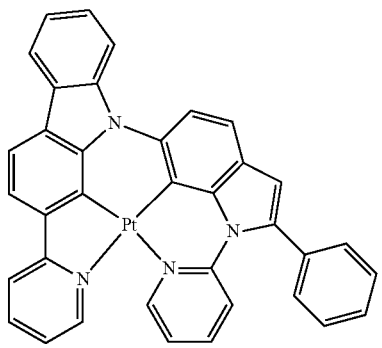
72
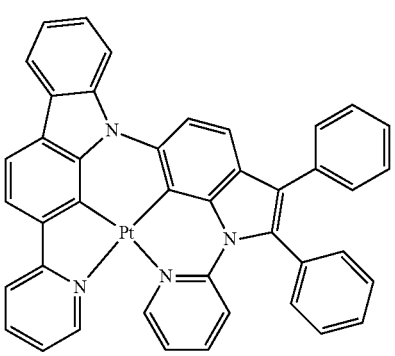
73
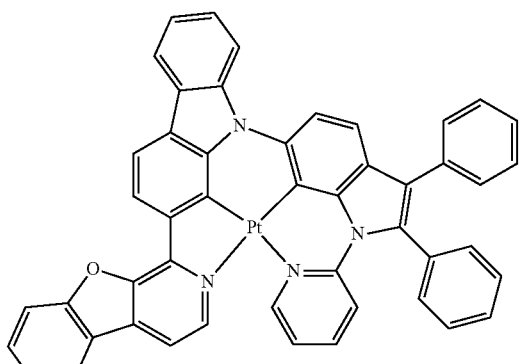
74
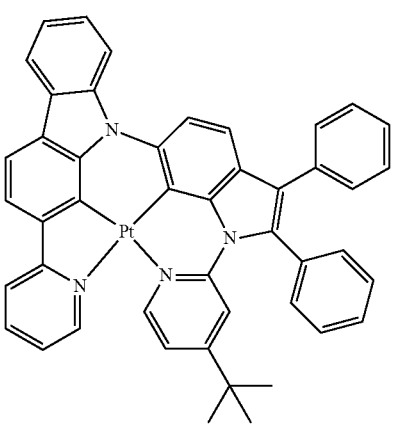

235 -continued
75
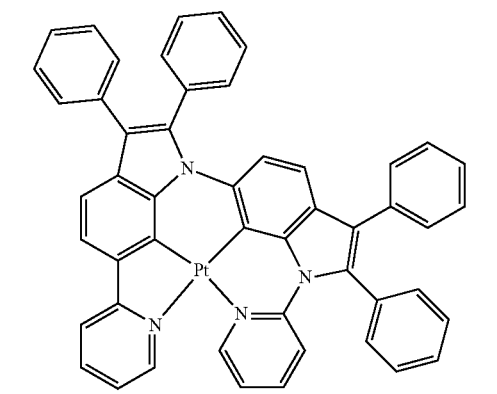
76
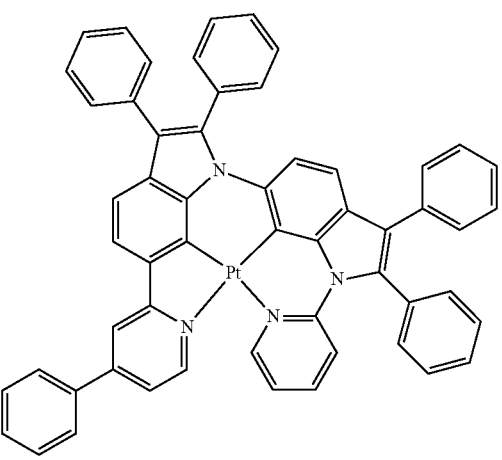
77
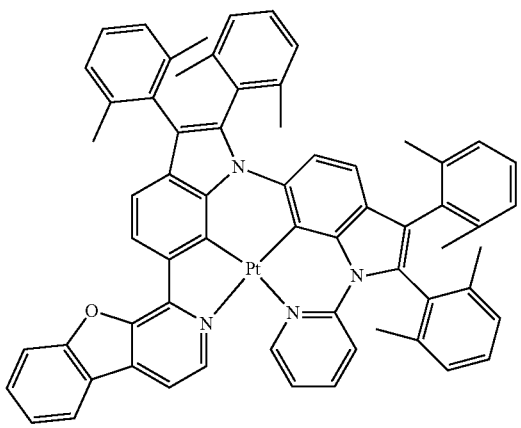
78
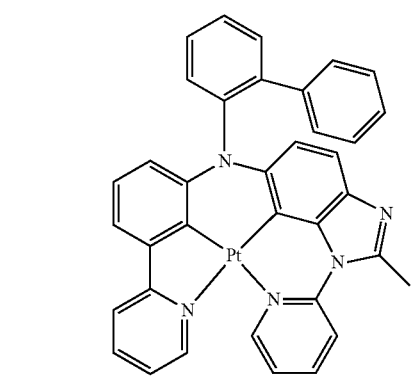
236 -continued
79
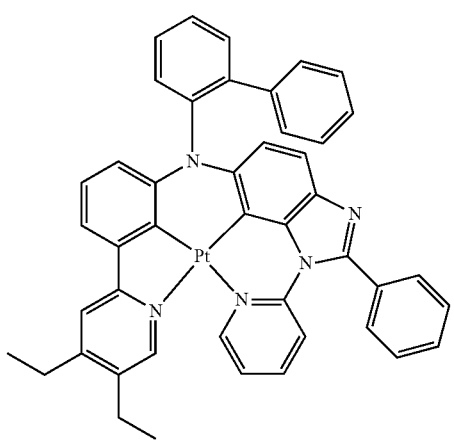
80
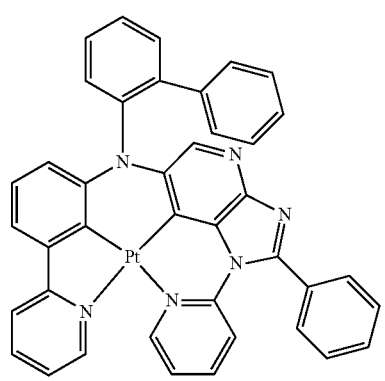
81
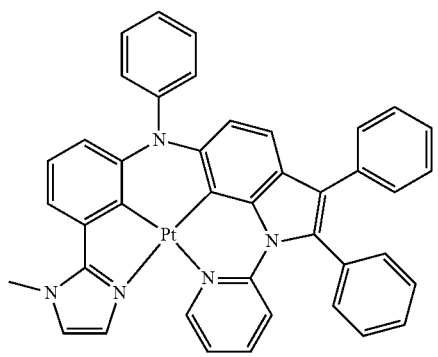
82
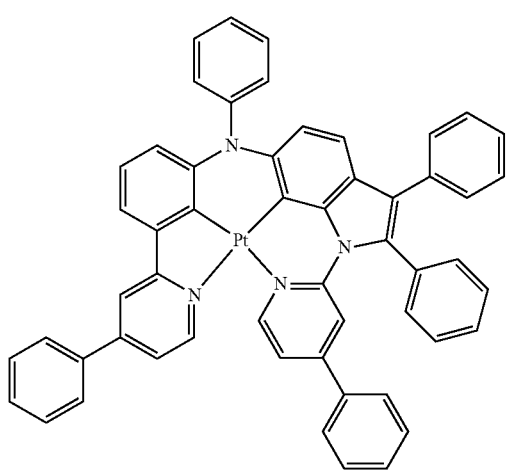

83
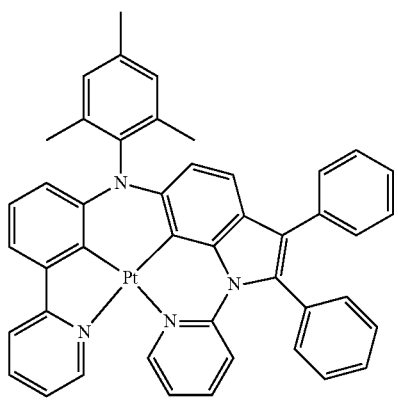
84
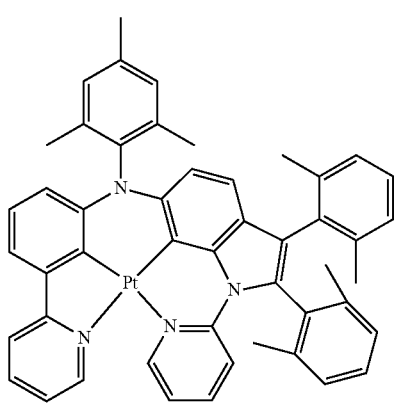
85
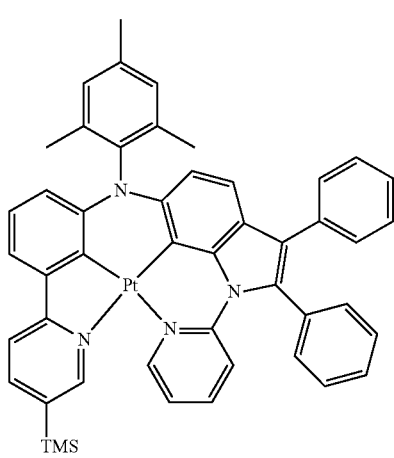
86
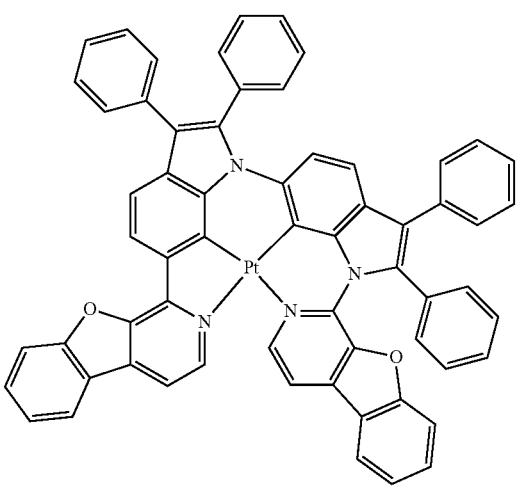
87
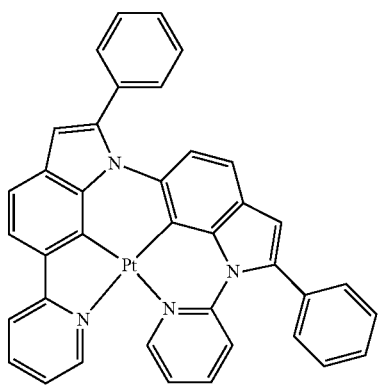
88
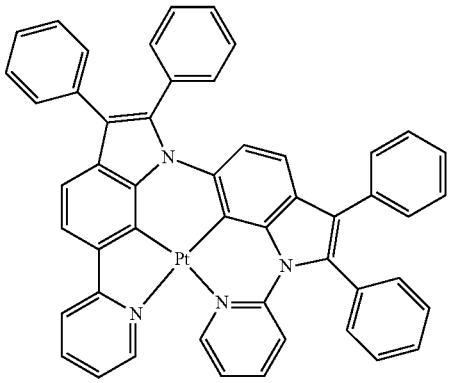

-continued
89
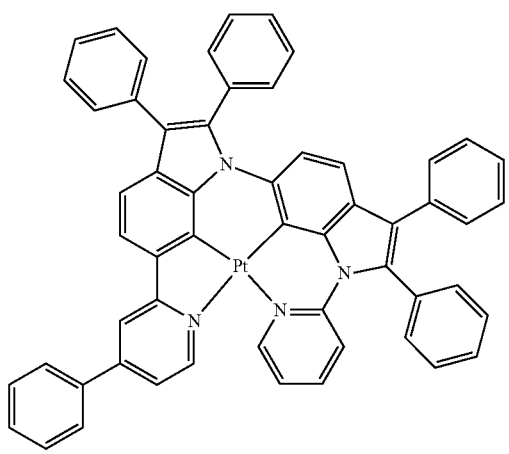
90
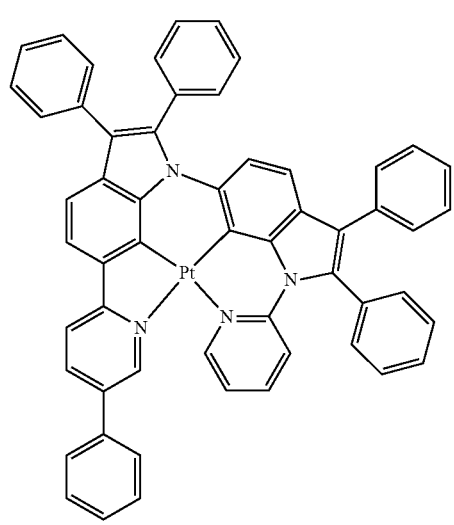
91
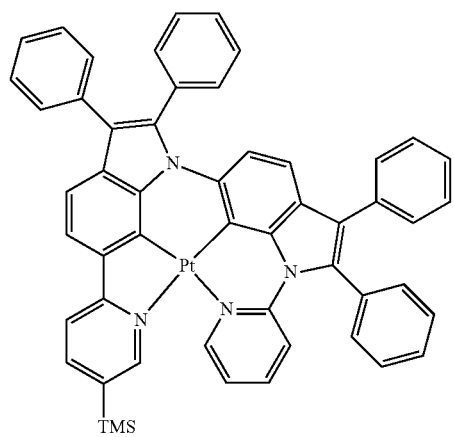
-continued
92
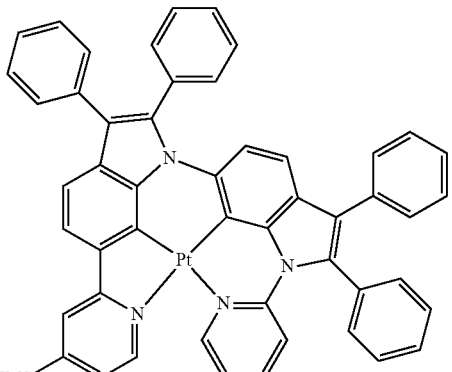
93
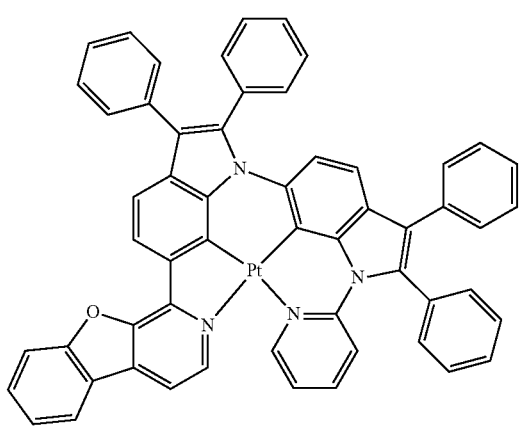
94
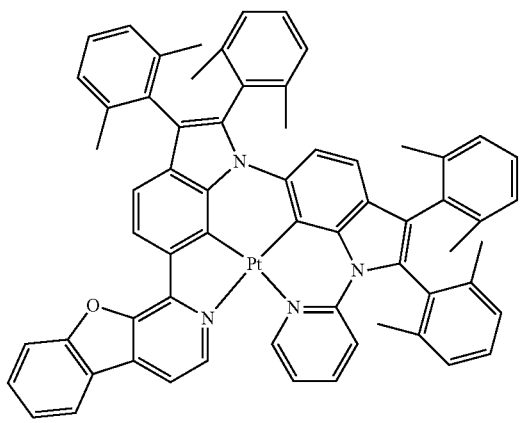
95
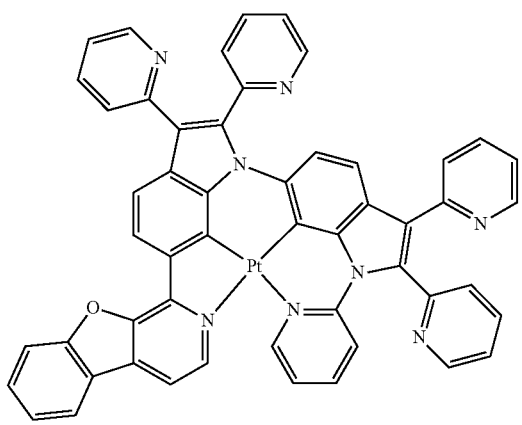

241
-continued
96
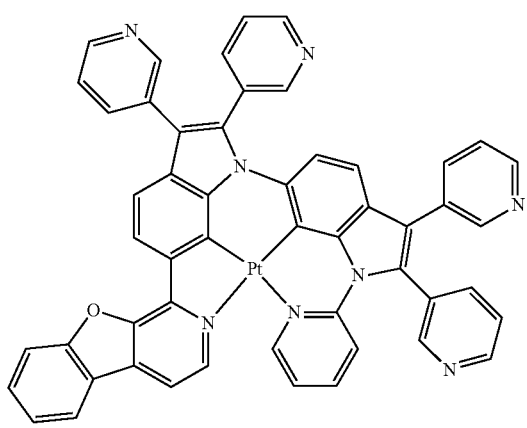
97
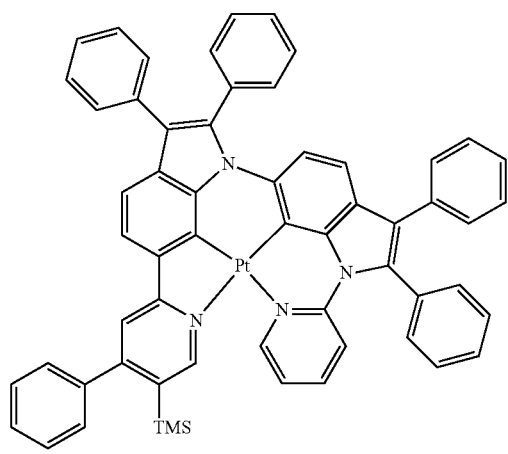
98
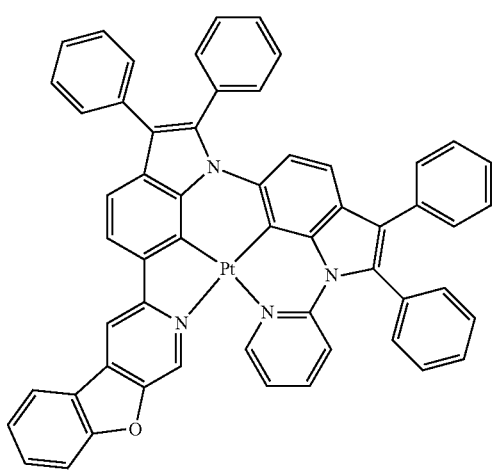
242
-continued
99
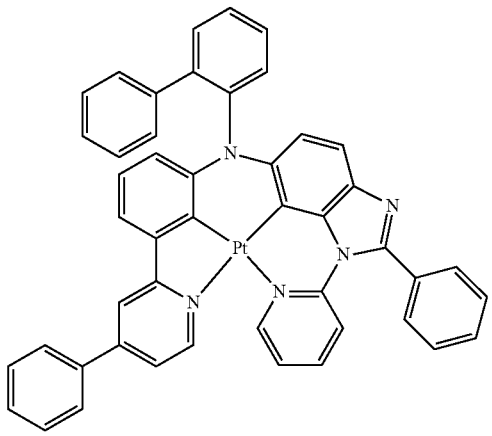
100
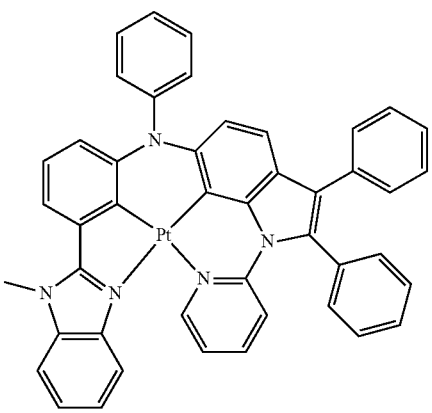
101
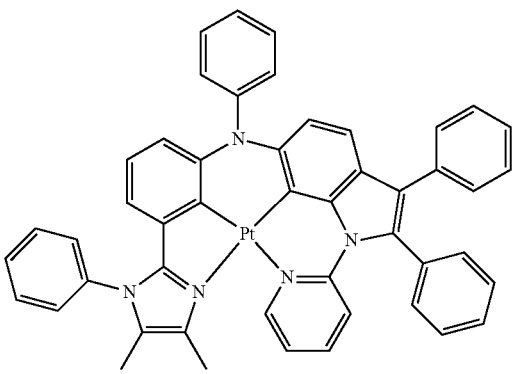

243
-continued

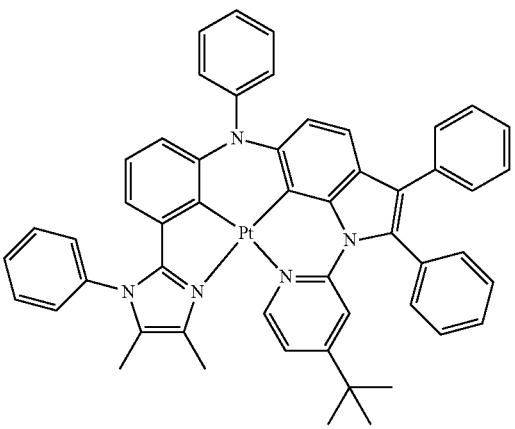
102

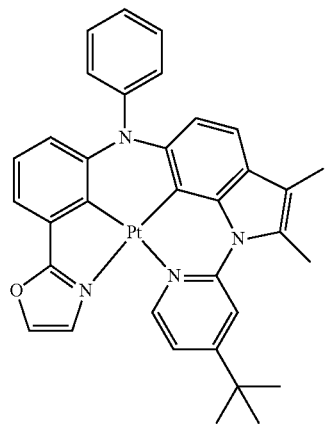
103

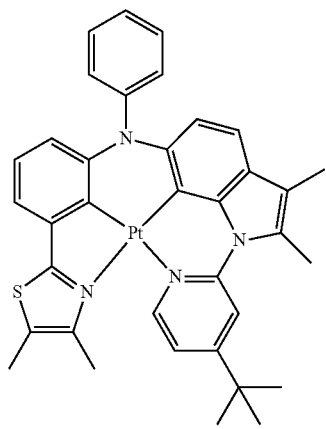
104

244
-continued

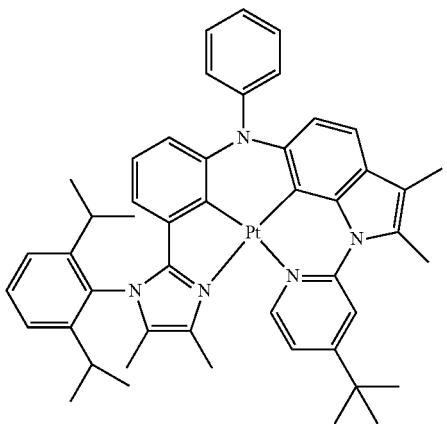
105

16. An organic light-emitting device comprising:
a first electrode;
a second electrode; and
an organic layer disposed between the first electrode and the second electrode,
wherein the organic layer comprises an emission layer and at least one of the organometallic compound of claim 1.

17. The organic light-emitting device of claim 16, wherein
the first electrode is an anode,
the second electrode is a cathode,
the organic layer further comprises a hole transport region disposed between the first electrode and the emission layer and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

18. The organic light-emitting device of claim 16, wherein the emission layer comprises the organometallic compound.

19. The organic light-emitting device of claim 18, wherein the emission layer further comprises a host, and an amount of the host is larger than an amount of the organometallic compound.

20. A diagnostic composition comprising at least one of the organometallic compound of claim 1.

* * * * *